(12) United States Patent
Deslattes Mays et al.

(10) Patent No.: US 10,961,545 B2
(45) Date of Patent: Mar. 30, 2021

(54) DROUGHT RESISTANCE IN PLANTS: UPL4

(71) Applicant: Keygene N.V., Wageningen (NL)

(72) Inventors: Anne Deslattes Mays, AE Wageningen (NL); Marieke Helena Adriana Van Hulten, AE Wageningen (NL); Shital Anilkumar Dixit, AE Wageningen (NL); Martin De Vos, AE Wageningen (NL); Jesse David Munkvold, Rockville, MD (US); Matthew Vitabile Dileo, Silver Spring, MD (US)

(73) Assignee: KEYGENE N.V., Wageningen (NL)

( * ) Notice: Subject to any disclaimer, the term of this patent is extended or adjusted under 35 U.S.C. 154(b) by 0 days.

(21) Appl. No.: 16/399,655

(22) Filed: Apr. 30, 2019

(65) Prior Publication Data
US 2019/0249186 A1    Aug. 15, 2019

Related U.S. Application Data

(62) Division of application No. 14/377,842, filed as application No. PCT/NL2013/050100 on Feb. 18, 2013, now Pat. No. 10,308,952.

(60) Provisional application No. 61/599,963, filed on Feb. 17, 2012.

(51) Int. Cl.
*C12N 15/82*    (2006.01)
(52) U.S. Cl.
CPC .............................. *C12N 15/8273* (2013.01)
(58) Field of Classification Search
None
See application file for complete search history.

(56) References Cited

U.S. PATENT DOCUMENTS

| | | | |
|---|---|---|---|
| 7,435,874 | B2 | 10/2008 | Gebhardt |
| 9,909,138 | B2 | 3/2018 | Deslattes Mays et al. |
| 2004/0031072 | A1 | 2/2004 | La Rosa et al. |
| 2004/0123343 | A1 | 6/2004 | La Rosa et al. |
| 2006/0123505 | A1 | 6/2006 | Kikuchi et al. |
| 2006/0150283 | A1 | 7/2006 | Alexandrov et al. |
| 2007/0266453 | A1 | 11/2007 | Anderson |
| 2009/0094717 | A1 | 4/2009 | Troukhan et al. |
| 2009/0144850 | A1 | 6/2009 | Van Winkle |
| 2010/0212050 | A1 | 8/2010 | Shoseyov et al. |
| 2011/0099668 | A1 | 4/2011 | Singh et al. |
| 2011/0162107 | A1 | 6/2011 | Inze et al. |
| 2011/0214205 | A1 | 9/2011 | Dietrich et al. |
| 2012/0260373 | A1 | 10/2012 | Apuya |
| 2016/0010108 | A1 | 1/2016 | Deslattes Mays et al. |

FOREIGN PATENT DOCUMENTS

| | | |
|---|---|---|
| EP | 1 685 242 B1 | 8/2006 |
| JP | 2015-508649 A | 3/2015 |
| JP | 2015-508650 A | 3/2015 |
| WO | WO-02/083911 A1 | 10/2002 |
| WO | WO-03/020015 A2 | 3/2003 |
| WO | WO-2004/035798 A2 | 4/2004 |
| WO | WO-2010/083178 | 7/2010 |
| WO | WO-2011/038389 A2 | 3/2011 |

OTHER PUBLICATIONS

Ning et al 2011 (Plant Physiology 157: p. 242-255) (Year: 2011).*
Till et al 2007 (BMC Plant Biology 7:19) (Year: 2007).*
"Predicted: probable pectinesterase 53-like [Glycine max]", GenBank Accession No. XP_003516527.2, Nov. 8, 2011 (Aug. 11, 2011).
Harriman et al. Molecular cloning of tomato pectin methylesterase gene and its expression in Ruters, Ripening Inhibitor, Nonripening, and Never Ripe tomato fruits. Plant Physiology.(1991) 97:80-87.
Huang et al. Pectin Methylesterase53 contributes to heat tolerance through its role in promoting stomatal movement. Plant Physiology. (2017) 174:748-763.
Paterson AH et al., Probable pectinesterase 53 isoform X2 [Sorghum bicolor], GenBank Accession No. XP_002440102.1, Jul. 13, 2009 (Jul. 13, 2009).
Swarbreck D et al., Pectin lyase-like superfamily protein [*Arabidopsis thaliana*], GenBank Accession No. NP_197474.1, May 28, 2011 (May 28, 2011).
Weber et al. A mutation in the *Arabidopsis thaliana* cell wall biosynthesis gene pectin methylesterase 3 as well as its aberrant expression cuse hypersensitivity specifically to Zn. The Plant Journal. (2013) 76: 151-164.
Yan et al. Pectin methylesterase31 positively regulates salt stress tolerance in *Arabidopsis*. Biochemical and Biophysical Research Communications. (2018) 496:497-501.
Cogoni et al., "Post-transcriptional gene silencing across kingdoms", Current Opinion in Genes & Development, 2000, vol. 10, pp. 628-643 (6 pages).
Matzke, et al. "How and why do plants inactivate homologous (Trans)genes?", Plant Physiology, dated 1995, vol. 107, pp. 679-685 (7 pages).
"*Arabidopsis thaliana* pectinesterase (AT5G19730)mRNA, complete cds", GenBank Database,Accession No. NM_121978.
ABRC. Germplasm SALK_ 136556.27.x. Published Mar. 3, 2003. pp. 1-2.
ABRC. Germplasm SALK_136556C. Published Apr. 12, 2007. pp. 1-2.
Aharoni, et al. "The SHINE Clade of AP2 Domain Transcription Factors Activates Wax Biosynthesis, Alters Cuticle Properties, and Confers Drought Tolerance when Overexpressed in *Arabidopsis*", The Plant Cell, Sep. 2004, vol. 16, pp. 2463-2480.

(Continued)

*Primary Examiner* — Matthew R Keogh

(74) *Attorney, Agent, or Firm* — Foley & Lardner LLP; Sunit Talapatra

(57) ABSTRACT

The present invention relates to a new method for increasing drought resistance of a plant. The method encompasses the impairment of the expression of a gene or genes in said plant. In comparison to a plant not manipulated to impair the expression of said gene(s), the plants display improved drought resistance. Also provided are plants and plant product that can be obtained by the method according to the invention.

13 Claims, 4 Drawing Sheets

Specification includes a Sequence Listing.

(56) References Cited

OTHER PUBLICATIONS

Alonso, et al. "Genome-Wide Insertional Mutagenesis of *Arabidopsis thaliana*", Science, Aug. 1, 2003, vol. 301, pp. 653-657.
An et al. Pepper pectin methylesterase inhibitor protein CaPMEI1 is required for antifungal activity, basal disease resistance and abiotic stress tolerance. Planta., 2008., vol. 228, pp. 61-78.
Barbagallo, et al. "Pectin methylesterase, polyphenol oxidase and physicochemical properties of typical long-storage cherry tomatoes cultivated under water stress regime", Journal of Science of food and Agriculture (2008) vol. 88, pp. 389-396.
Bray, "Plant responses to water deficit", Trends in Plant Science, Feb. 1997, vol. 2, No. 2, pp. 48-54.
Brenner, "Errors in genome annotation", TIG, 1999, vol. 15, No. 4, pp. 132-133.
Camacho-Cristobal, et al. "The expression of several cell wall-related genes in *Arabidopsis* roots is down-regulated under boron deficiency" Environmental and Experimental Botany (2008) vol. 63, pp. 351-358.
Chang et al. Papaya pectinesterase inhibition by sucrose. 24th Annual Meeting of the Institute of Food Technologies. May 24-28, 1964. pp. 218-222.
Cho, et al. "*Arabidopsis* PUB22 and PUB23 are Homologous U-Box E3 Ubiquitin Ligases That Play Combinatory Roles in Response to Drought Stress", The Plant Cell, Jul. 2008, vol. 20, pp. 1899-1914.
Cho, et al. "ROS-Mediated ABA Signaling", J. Plant Biol., 2009, vol. 52, pp. 102-113.
Coates et al., "Armadillo repeat proteins: versatile regulators of plant development and signaling", Plant Cell Monographs, 2007, vol. 10. pp. 299-314.
Denby, et al. "Engineering drought and salinity tolerance in plants: lessons from genome-wide expression profiling in *Arabidopsis*", Trends in Biotechnology, Nov. 2005, vol. 23, No. 11, pp. 547-552.
Devereux, J., et al., A comprehensive set of sequence analysis programs for the VAX, Nucleic Acids Research, 1984, vol. 12, Issue 1, pp. 387-395.
Downes, et al. "The HECT ubiquitin-protein ligase (UPL) family in *Arabidopsis*: UPL3 has a specific role in trichome development", The Plant Journal, 2003, vol. 35, pp. 729-742.
El Refy, et al. "The *Arabidopsis* KAKTUS gene encodes a HECT protein and controls the number of endoreduplication cycles", Mol Gen Genomics (2003), vol. 270, pp. 403-414.
ExplorEnz. EC 3.1.1.11. Pectinesterase. 2001. 1 pg.
Fagard, et al. "Cell wall mutants" Plant Physiology and Biochemistry (Jan. 2000) vol. 38,(1/2), pp. 15-25.
Final Office Action on U.S. Appl. No. 14/377,842 dated Aug. 13, 2018.
Final Office Action on U.S. Appl. No. 14/377,843 dated Aug. 3, 2018.
Genbank Accession NP_195908.1, first available online Aug. 21, 2001.
Gray et al. The use of transgenic and naturally occurring mutants to understand and manipulate tomato fruit ripening. Plant, Cell and Environment. 1994. 17:557-571.
Gul et al., "Metozoan evolution of the armadillo repeat superfamily", Cell. Mol. Life Sci., 2017, vol. 74, pp. 525-541.
Hall et al., "Antisense inhibition of pectin esterase gene expression in transgenic tomatoes", The Plant Journal, 1993, vol. 3, No. 1, pp. 121-129.
Harb, et al. "Molecular and Physiological Analysis of Drought Stress in *Arabidopsis* Reveals Early Responses Leading to Acclimation in Plant Growth", Plant Physiology, Nov. 2010, vol. 154, pp. 1254-1271.
Hong et al., "Functional characterization of pectin methylesterase inhibitor (PMEI) in wheat", Genes Genet. Syst, 2010, vol. 85, pp. 97-106.
Hyun An, et al. "Pepper pectin methylesterase inhibitor protein CaPMEI1 is required for antifungal activity, basal disease resistance and abiotic stress tolerance", Planta (2008) vol. 228, pp. 61-78.
International Search Report & Written Opinion in NL Appln No. 2006005 dated Aug. 17, 2011.
International Search Report & Written Opinion in NL Appln No. 2006007 dated Aug. 18, 2011.
International Search Report in PCT/NL2013/050100 dated Jun. 10, 2013.
International Search Report in PCT/NL2013/050101 dated Jun. 10, 2013.
International Search Report in PCT/NL2013/050102 dated Jun. 12, 2013.
Karaba, et al. "Improvement of water use efficiency in rice by expression of HARDY, an *Arabidopsis* drought and salt tolerance gene", PNAS, Sep. 2007, vol. 104, No. 39, pp. 15270-1575.
Kasuga et al., "Improving Plant Drought, Salt, and Freezing Tolerance by Gene Transfer of a Single Stress-inducible Transcription Factor," Nature Biotechnology, vol. 17, pp. 287-291 (1999).
Kilian, et al. "The AtGenExpress global stress expression data set: protocols, evaluation and model data analysis of UV-B light, drought and cold stress responses", The Plant Journal, 2007, vol. 50, pp. 347-363.
Kwak, et al. "NADPH oxidase AtrbonD and AtrbonF genes function in ROS-dependent ABA signaling in *Arabidopsis*", The EMBO Journal, 2003, vol. 22, No. 11, pp. 2623-2633.
Kwak, et al. "The Clickable Guard Cell, Version II: Interactive Model of Guard Cell Signal Transduction Mechanisms and Pathways", *Arabidopsis* Book, 2008, vol. 6, e0114, 16 pgs.
Kwak, et al. "The Role of Reactive Oxygen Species in Hormonal Responses", Plant Physiology, Jun. 2006, vol. 141, pp. 323-329.
Lee, et al. "Activation of Glucosidase via Stress-Induced Polymerization Rapidly Increases Active Pools of Abscisic Acid", Cell, Sep. 2006, vol. 126, pp. 1109-1120.
Lionetti et al., "Engineering the cell wall by reducing de-methyl-esterified homogalacturonan improves saccharification of plants tissues for bioconversion", PNAS, Jan. 12, 2010, vol. 107, No. 2, pp. 616-621.
Louvet, et al. "Comprehensive expression profiling of the pectin methylesterase gene family during silique development in *Arabidopsis thaliana*", PLANTA, 2006, vol. 226, pp. 782-791.
Mudgil et al., "A large complement of the predicted *Arabidopsis* ARM repeat proteins are members of the U-Box E3 ubiquitin ligase family", Plant Physiology, Jan. 2004, vol. 134, pp. 59-66.
Non-Final Office Action on U.S. Appl. No. 14/377,843 dated Jan. 24, 2019.
Non-Final Office Action on U.S. Appl. No. 15/880,825 dated Jan. 29, 2019.
Notice of Allowance on U.S. Appl. No. 14/377,842 dated Jan. 17, 2019.
Notice of Reasons for Rejection issued in co-pending Japanese Application No. 2014-557587, dated Jan. 31, 2017, with English translation.
Notice of Reasons for Rejection issued in co-pending Japanese Application No. 2014-557588, dated Jan. 31, 2017, with English translation.
Office Action issued in Chinese Application No. 201380009865.8 dated Sep. 9, 2015.
Paterson, et al. "The Sorghum bicolor genome and the diversification of grasses", Nature, Jan. 2009, vol. 457, pp. 551-556.
Pennisi, "The Blue Revolution, Drop by Drop, Gene by Gene", Science, Apr. 2008, vol. 320, pp. 171-173.
Perazza, et al. "Trichome Cell Growth in *Arabidopsis thaliana* Can be Depressed by Mutations in at Least Five Genes", Genetics (May 1999), vol. 152, pp. 461-476.
Qin, et al. "*Arabidopsis* DREB2A-Interacting Proteins Function as Ring E3 Ligases and Negatively Regulate Plant Drought Stress-Responsive Gene Expression", The Plant Cell, Jun. 2008, vol. 20, pp. 1693-1707.
Qu et al, "Brassinosteroids regulate pectin methylesterase activity and AtPME41 expression in *Arabidopsis* under chilling stress", Cryobiology, 2011, vol. 63, pp. 111-117.
Retrieved from EBI accession No. UNIPROT:C5Z1DO, Sep. 1, 2009, "RecName: Full=Pectinesterase; EC=3.1.1.11;".

(56) References Cited

OTHER PUBLICATIONS

Retrieved from EBI accession No. UNIPROT:Q8VYZ3, Mar. 1, 2002, "RecName: Full=Probable pectinesterase 53; Short=PE 53; EC=3.1.1.11; AltName: Full=Pectin methylesterase 53; short-AtPME53; Flags: Precursor,".
Rotin et al., "Physiological functions of the HECT family of ubiquitin ligases", Nature Reviews Molecular Cell Biology, 2009, vol. 10, pp. 398-409.
Search Report in NL Appln No. 2006006 dated Aug. 17, 2011.
Serrano, et al. "A glimpse of the mechanisms of ion homeostasis during salt stress", Journal of Experimental Botany, Jun. 1999, vol. 50, Special Issue, pp. 1023-1036.
Seymour, et al. "Down-regulation of two non-homologous endogenous tomato genes with a single chimaeric sense gene construct", Database Accession No. PREV199497005095 (1993).
Sinaki, et al. "The Effects of Water Deficit During Growth Stages of Canola (*Brassica napus* L.)", American-Eurasian J. Agric. & Environ. Sci, 2007, vol. 2, No. 4, pp. 417-422.
Snow, et al. "Evaluation of a System for the Imposition of Plant Water Stress", Plant Physiol, 1985, vol. 77, pp. 602-607.
Speulman, et al. "Target selected insertional mutagenesis on chromosome IV of *Arabidopsis* using the En-I transposon system", Journal of Biotechnology (2000), vol. 78, pbs 301-312.
Swindell, "The Association Among Gene Expression Responses to Nine Abiotic Stress Treatments in *Arabidopsis thaliana*", Genetics, Dec. 2006, vol. 1811-1824.
Szymanski, "Chapter 22: The role of actin during *Arabidopsis trichome* morphogenesis", Actin: A Dynamic Framework for Multiple Plant Cell Functions, Springer-Science Business Media, B.V., 2000, 20 pages.
Tian, et al. "Pollen-specific pectin methylesterase involved in pollen tube growth", Developmental Biology (2006) vol. 294, pp. 83-91.
U.S. Office Action on 085342-0333 dated Feb. 19, 2016.
U.S. Office Action on U.S. Appl. No. 14/377,842 dated Mar. 15, 2018.
U.S. Office Action on U.S. Appl. No. 14/377,842 dated Nov. 21, 2016.
U.S. Office Action on U.S. Appl. No. 14/377,843 dated Apr. 11, 2017.
U.S. Office Action on U.S. Appl. No. 14/377,843 dated Nov. 21, 2016.
U.S. Office Action on U.S. Appl. No. 14/377,844 dated Jun. 1, 2016.
U.S. Office Action on U.S. Appl. No. 14/377,844 dated Jul. 18, 2017.
U.S. Office Action on U.S. Appl. No. 14/377,844 dated Sep. 28, 2016.
Wang, et al. "Plant responses to drought, salinity and extreme temperatures: towards genetic engineering for stress tolerance", Planta, 2003, vol. 218, pp. 1-14.
Yamada, et al. "*Arabidopsis thaliana* putative pectin methylesterase (At5g19730) mRNA, complete cds", Database acession No. AY065431 (Dec. 13, 2001).
Zhi-Biao, et al. "Analysis of two antisense transgenes inhibiting expression of their endogenous genes in transgenic tomatoes", Database Accession No. PREV199699184897 (1996).
Phan et al., "Silencing of the Major Salt-Dependent Isoform of Pectinesterase in Tomato Alters Fruit Softening," Plant Physiology, Aug. 2007, pp. 1960-1967, vol. 144, American Society of Plant Biologists.

* cited by examiner

Wild-type    At5g02880 KO

SEQUENCE LISTING

<160> NUMBER OF SEQ ID NOS: 12

<210> SEQ ID NO 1
<211> LENGTH: 4509
<212> TYPE: DNA
<213> ORGANISM: Arabidopsis thaliana

<400> SEQUENCE: 1

| | | | | | | |
|---|---|---|---|---|---|---|
| atggagaaca | gaggccagaa | acgaatggag | gttgtggaag | agttacctgc | tgataagaga | 60 |
| gcttgtaact | ctcaggattt | tagaccaagc | acatccggat | catctgttca | agctcaagct | 120 |
| aatgatacga | atccaggaca | tgaaaacgtt | gacgctgata | tggatacttc | ttcatctgct | 180 |
| tcgccttcga | gtcgatcaga | tgaagaagaa | caggaagagc | aggataagga | ggattcggac | 240 |
| tatggatctt | gcgattctga | tgaggaagat | ccgaggcaga | gggtgcttca | ggattaccag | 300 |
| aggcagagat | catctggtga | tcatgggaaa | ttgaagtctc | ttttgttgaa | tttgactgga | 360 |
| gaaactgatc | cttctggaca | gttatccagg | ctcactgagt | tatgtgaagt | gttgtcattt | 420 |
| tctactgaag | aatcgctgtc | cagtgttatg | ccaacatgc | tatcaccggt | gcttgtaaag | 480 |
| ttagctaagc | atgagaacaa | tgcagatatt | atgctcctcg | caattagagc | tattacttat | 540 |
| ttgtgtgatg | tttatccgcc | gtcagtagaa | ttccttgtaa | gacatgatac | cattcctgct | 600 |
| ctctgccaaa | gacttttgac | tattgagtac | ttggacgttg | ctgagcagtg | tttgcaagca | 660 |
| cttgagaaaa | tatcccgaga | tgagccggta | gcctgcttga | atgctggagc | aattatggca | 720 |
| gtgctttcgt | ttattgattt | cttctcaaca | agcatacaga | gagtcgcaat | ttctactgtg | 780 |
| gtcaatatat | gtaagcagct | ttcttctgag | tctccctcgc | ctttcatgga | tgctgttcca | 840 |
| atattatgca | ctcttcttca | atatgaagat | cgacagctgg | tcgagaatgt | ggctatttgc | 900 |
| ttgacaaaaa | tagcagatca | agccagtgag | tcaccggcaa | tgttggatca | actgtgtagg | 960 |
| catggactaa | ttaatgaatc | aacacatctc | ttaaacttga | atagccgcac | taccctatct | 1020 |
| caacctgtct | acaatggtgt | gattggaatg | ctaagaaaac | tatcttctgg | ttcagctta | 1080 |
| gctttcagaa | cgttatatga | gcttaacatt | ggctacagtt | taaagaaat | catgtccacg | 1140 |
| tatgacattt | ctcattcagt | gtcttctaca | catcctatca | atgcatgttc | taatcaggtg | 1200 |
| catgaagtcc | tgaagttggt | gattgagctt | cttccagctt | cacccgtaga | ggataatcag | 1260 |
| ctggcatcgg | aaaaggaaag | ttttctcgtc | aatcagcctg | atcttttgca | acaatttgga | 1320 |
| agagacatgc | ttcctgtcat | gattcaggtg | ctaaactctg | gagctaacgt | atatgtttct | 1380 |
| tatggttgcc | tatcagcaat | tcacaagctg | acttgcttga | gtaagtccgg | tgatattgtc | 1440 |
| gagttactga | agaacaccaa | catgtcaagt | gttttggctg | gcattctgtc | aaggaaggat | 1500 |
| catcatgtaa | ttgtagtagc | actacaggtt | gcggaagtgc | ttcttgagaa | atacagagat | 1560 |
| acttttttga | attcttttat | aaaggaaggt | gttttttttcg | cgattgaagc | actcttaagt | 1620 |
| tctgatagag | ggcaacaaaa | tcagggatca | gctgacccttt | cacaaaagcc | tgttacaaaa | 1680 |
| gagattgtga | atgcttgtg | ccaatctttt | gaaagatcgc | tatcctcttc | ttcacaaact | 1740 |
| tgtaagattg | aaaaggattc | tgtctacgtt | cttgcaacac | gtatcaagga | gggtttcttt | 1800 |
| ggacctgagg | tattcaactc | tgagaaaggc | ttgacagatg | tcctccaaaa | cctcaagaac | 1860 |
| ttgtcggtag | cacttagcga | gttgatgact | gtacccattg | atgcgcatgt | cctgcatgat | 1920 |
| gagaaattct | tctcaatatg | gaaccaaatc | atggaaaggc | tgaatggaag | ggaatctgtg | 1980 |
| tccacttttg | aattcattga | gagcggagtt | gtaaagtcac | tggcaagtta | tctttctaat | 2040 |
| ggactctatc | aaaggaaact | tagcaaaggg | ggtcctgaat | gtgatagttt | accatttatt | 2100 |

```
ggtaagagat tgaggtgtt cacaagattg ctttggtctg atggagaggc aacttcatcc   2160
ttgttaatac agaagctcca aaattccctt tcttctttgg aaaacttccc aattgtccta   2220
agccaatttt tgaagcagaa gaactcattt gcggctattc caaatgggcg ttgcactagt   2280
tatccatgcc taaaagttcg ttttctgaaa gcagagggg agacttcttt gcgtgattac    2340
tcccaagact tgtcactgt tgacccactt tgctatttgg atgctgtcga tcaatacttg    2400
tggcctaaag ttaatataga acctatagat tctgtggaag caaagatca agctatagaa    2460
tgtcaatctt ctcaattgca gtcaacttcg atatcttgtc aagctgaaag ctcaagtcct   2520
atggagattg acagtgagtc ttctgatgcg tctcagttgc agggatctca agtggaagat   2580
cagacgcaac ttccaggaca acagaatgct tcctcctctg aaacctcctc tgaaaaagag   2640
gatgcggtac ctagactttt gtttcgtctc gaagggcttg aactagaccg ttctttgaca   2700
gtatatcagg cgattctctt gcacaaacta aaatcagaaa gtgaagcaac caacgattcg   2760
aagctgagtg gaccccacaa catcacttat gaaaggtctg cacaacttgg ggattctcgt   2820
gaaaatctgt ttccacctgg atctatggaa gatgatgagt atcgcccgtt cttgtcctat   2880
tgtttactc atagacttgc tttgcgcctg aaggggtcaa gtcatcctcc gtatgacata    2940
ttgtttcttc ttaagagtct ggagggcatg aacagatttc tctttcacct gatttctctt   3000
gaacggatta atgcttttgg tgaaggtagg ctagagaatt tggatgatct gagggtacaa   3060
gttcgtcctg tgccacattc tgaatttgtt agcagtaagc ttacagagaa gttagagcag   3120
cagcttcgtg attcttttgc tgtgtcaacc tgcggtctgc caccatggtt taatgatcta   3180
atggattcat gtccgtgttt atttagtttt gaagccaagt ctaaatactt ccgacttgca   3240
gcctttggtt cacagaaaat ccgtcatcat ccacagcacc ttagcagttc aaatgttcat   3300
ggcgaagcgc gcccagtgac tggtagttta cctcgtaaaa agttcttagc ttgccgtgaa   3360
aacattctag agtctgctgc caaaatgatg gagttatatg gaaaccagaa ggtggtcatt   3420
gaggttgaat acagtgaaga agtcgggact ggtcttgggc aacactgga gttctatacg    3480
cttgtcagta gggcatttca aaatcccgat cttggtatgt ggagaaatga ttgtagtttt   3540
attgttggaa agccagtcga acactcggga gttttggcat cttcttcagg actcttttca   3600
cgcccttggt caggtacatc aactacgtca gatgtgctgc agaaatttgt cctcttgggg   3660
acagtggtag caaaggcttt acaagatgga cgagtcttag accttccact ttccaaagcc   3720
ttctacaaat taattctcgg acaggagttg agttcatttg acatccactt cgttgaccct   3780
gaactttgta aaacactggt ggaattgcaa gctctggtac gtaggaaaaa gcttttcgct   3840
gaagcacatg gtgattccgg agcagccaag tgtgatttaa gtttccatgg aacaaagatt   3900
gaggaccttt gtcttgaatt tgcattgcct ggctacacgg attatgatct cgctccctat   3960
tctgcaaatg atatggtaaa tttggataac ctcgaggaat atatcaaggg tattgtcaat   4020
gccacagtat gtaatgggat ccaaaaacaa gtggaagcat tcggtctgg atttaatcag    4080
gttttctcta ttgaacatct tcggatattc aacgaagagg agctggaaac tatgctgtgt   4140
ggagaatgtg atctcttag tatgaatgaa gtcttggatc acatcaagtt tgatcatgga   4200
tatacttcta gcagcccacc agttgaatat ttattgcaga ttctgcatga gtttgatagg   4260
gagcaacaac gagcctttt gcaatttgta acaggatctc cccggttacc tcatggtggt    4320
ttggcgtctc tcagtcccaa actaacaatc gtccgcaagc atggtagcga ttcttcagat   4380
actgacctcc ctagtgtgat gacatgcgcc aattatctga agcttcctcc ttattcatcc   4440
```

```
aaagagaaga tgaaggagaa gctgatttat gccataacgg aaggtcaagg ttccttccat   4500
ctctcttaa                                                          4509
```

<210> SEQ ID NO 2
<211> LENGTH: 1502
<212> TYPE: PRT
<213> ORGANISM: Arabidopsis thaliana

<400> SEQUENCE: 2

```
Met Glu Asn Arg Gly Gln Lys Arg Met Glu Val Val Glu Glu Leu Pro
1               5                   10                  15

Ala Asp Lys Arg Ala Cys Asn Ser Gln Asp Phe Arg Pro Ser Thr Ser
            20                  25                  30

Gly Ser Ser Val Gln Ala Gln Ala Asn Asp Thr Asn Pro Gly His Glu
        35                  40                  45

Asn Val Asp Ala Asp Met Asp Thr Ser Ser Ser Ala Ser Pro Ser Ser
    50                  55                  60

Arg Ser Asp Glu Glu Gln Glu Gln Asp Lys Glu Asp Ser Asp
65                  70                  75                  80

Tyr Gly Ser Cys Asp Ser Asp Glu Glu Asp Pro Arg Gln Arg Val Leu
                85                  90                  95

Gln Asp Tyr Gln Arg Gln Arg Ser Ser Gly Asp His Gly Lys Leu Lys
            100                 105                 110

Ser Leu Leu Leu Asn Leu Thr Gly Glu Thr Asp Pro Ser Gly Gln Leu
        115                 120                 125

Ser Arg Leu Thr Glu Leu Cys Glu Val Leu Ser Phe Ser Thr Glu Glu
    130                 135                 140

Ser Leu Ser Ser Val Met Ala Asn Met Leu Ser Pro Val Leu Val Lys
145                 150                 155                 160

Leu Ala Lys His Glu Asn Asn Ala Asp Ile Met Leu Leu Ala Ile Arg
                165                 170                 175

Ala Ile Thr Tyr Leu Cys Asp Val Tyr Pro Pro Ser Val Glu Phe Leu
            180                 185                 190

Val Arg His Asp Thr Ile Pro Ala Leu Cys Gln Arg Leu Leu Thr Ile
        195                 200                 205

Glu Tyr Leu Asp Val Ala Glu Gln Cys Leu Gln Ala Leu Glu Lys Ile
    210                 215                 220

Ser Arg Asp Glu Pro Val Ala Cys Leu Asn Ala Gly Ala Ile Met Ala
225                 230                 235                 240

Val Leu Ser Phe Ile Asp Phe Ser Thr Ser Ile Gln Arg Val Ala
                245                 250                 255

Ile Ser Thr Val Val Asn Ile Cys Lys Gln Leu Ser Ser Glu Ser Pro
            260                 265                 270

Ser Pro Phe Met Asp Ala Val Pro Ile Leu Cys Thr Leu Leu Gln Tyr
        275                 280                 285

Glu Asp Arg Gln Leu Val Glu Asn Val Ala Ile Cys Leu Thr Lys Ile
    290                 295                 300

Ala Asp Gln Ala Ser Glu Ser Pro Ala Met Leu Asp Gln Leu Cys Arg
305                 310                 315                 320

His Gly Leu Ile Asn Glu Ser Thr His Leu Asn Leu Asn Ser Arg
                325                 330                 335

Thr Thr Leu Ser Gln Pro Val Tyr Asn Gly Val Ile Gly Met Leu Arg
            340                 345                 350

Lys Leu Ser Ser Gly Ser Ala Leu Ala Phe Arg Thr Leu Tyr Glu Leu
```

```
                355                 360                 365
Asn Ile Gly Tyr Ser Leu Lys Glu Ile Met Ser Thr Tyr Asp Ile Ser
    370                 375                 380
His Ser Val Ser Ser Thr His Pro Ile Asn Ala Cys Ser Asn Gln Val
385                 390                 395                 400
His Glu Val Leu Lys Leu Val Ile Glu Leu Pro Ala Ser Pro Val
                405                 410                 415
Glu Asp Asn Gln Leu Ala Ser Glu Lys Glu Ser Phe Leu Val Asn Gln
                420                 425                 430
Pro Asp Leu Leu Gln Gln Phe Gly Arg Asp Met Leu Pro Val Met Ile
                435                 440                 445
Gln Val Leu Asn Ser Gly Ala Asn Val Tyr Val Ser Tyr Gly Cys Leu
    450                 455                 460
Ser Ala Ile His Lys Leu Thr Cys Leu Ser Lys Ser Gly Asp Ile Val
465                 470                 475                 480
Glu Leu Leu Lys Asn Thr Asn Met Ser Ser Val Leu Ala Gly Ile Leu
                485                 490                 495
Ser Arg Lys Asp His His Val Ile Val Val Ala Leu Gln Val Ala Glu
                500                 505                 510
Val Leu Leu Glu Lys Tyr Arg Asp Thr Phe Leu Asn Ser Phe Ile Lys
    515                 520                 525
Glu Gly Val Phe Phe Ala Ile Glu Ala Leu Leu Ser Ser Asp Arg Gly
    530                 535                 540
Gln Gln Asn Gln Gly Ser Ala Asp Leu Ser Gln Lys Pro Val Thr Lys
545                 550                 555                 560
Glu Ile Val Lys Cys Leu Cys Gln Ser Phe Glu Arg Ser Leu Ser Ser
                565                 570                 575
Ser Ser Gln Thr Cys Lys Ile Glu Lys Asp Ser Val Tyr Val Leu Ala
                580                 585                 590
Thr Arg Ile Lys Glu Gly Phe Phe Gly Pro Glu Val Phe Asn Ser Glu
    595                 600                 605
Lys Gly Leu Thr Asp Val Leu Gln Asn Leu Lys Asn Leu Ser Val Ala
    610                 615                 620
Leu Ser Glu Leu Met Thr Val Pro Ile Asp Ala His Val Leu His Asp
625                 630                 635                 640
Glu Lys Phe Phe Ser Ile Trp Asn Gln Ile Met Glu Arg Leu Asn Gly
                645                 650                 655
Arg Glu Ser Val Ser Thr Phe Glu Phe Ile Glu Ser Gly Val Val Lys
                660                 665                 670
Ser Leu Ala Ser Tyr Leu Ser Asn Gly Leu Tyr Gln Arg Lys Leu Ser
    675                 680                 685
Lys Gly Gly Pro Glu Cys Asp Ser Leu Pro Phe Ile Gly Lys Arg Phe
    690                 695                 700
Glu Val Phe Thr Arg Leu Leu Trp Ser Asp Gly Glu Ala Thr Ser Ser
705                 710                 715                 720
Leu Leu Ile Gln Lys Leu Gln Asn Ser Leu Ser Ser Leu Glu Asn Phe
                725                 730                 735
Pro Ile Val Leu Ser Gln Phe Leu Lys Gln Lys Asn Ser Phe Ala Ala
                740                 745                 750
Ile Pro Asn Gly Arg Cys Thr Ser Tyr Pro Cys Leu Lys Val Arg Phe
    755                 760                 765
Leu Lys Ala Glu Gly Glu Thr Ser Leu Arg Asp Tyr Ser Gln Asp Phe
    770                 775                 780
```

```
Val Thr Val Asp Pro Leu Cys Tyr Leu Asp Ala Val Asp Gln Tyr Leu
785                 790                 795                 800

Trp Pro Lys Val Asn Ile Glu Pro Ile Asp Ser Val Glu Ala Lys Asp
            805                 810                 815

Gln Ala Ile Glu Cys Gln Ser Ser Gln Leu Gln Ser Thr Ser Ile Ser
            820                 825                 830

Cys Gln Ala Glu Ser Ser Ser Pro Met Glu Ile Asp Ser Glu Ser Ser
            835                 840                 845

Asp Ala Ser Gln Leu Gln Gly Ser Gln Val Glu Asp Gln Thr Gln Leu
850                 855                 860

Pro Gly Gln Gln Asn Ala Ser Ser Ser Glu Thr Ser Ser Glu Lys Glu
865                 870                 875                 880

Asp Ala Val Pro Arg Leu Leu Phe Arg Leu Glu Gly Leu Glu Leu Asp
                885                 890                 895

Arg Ser Leu Thr Val Tyr Gln Ala Ile Leu Leu His Lys Leu Lys Ser
                900                 905                 910

Glu Ser Glu Ala Thr Asn Asp Ser Lys Leu Ser Gly Pro His Asn Ile
        915                 920                 925

Thr Tyr Glu Arg Ser Ala Gln Leu Gly Asp Ser Arg Glu Asn Leu Phe
        930                 935                 940

Pro Pro Gly Ser Met Glu Asp Glu Tyr Arg Pro Phe Leu Ser Tyr
945                 950                 955                 960

Leu Phe Thr His Arg Leu Ala Leu Arg Leu Lys Gly Ser Ser His Pro
                965                 970                 975

Pro Tyr Asp Ile Leu Phe Leu Leu Lys Ser Leu Glu Gly Met Asn Arg
            980                 985                 990

Phe Leu Phe His Leu Ile Ser Leu  Glu Arg Ile Asn Ala  Phe Gly Glu
            995                 1000                1005

Gly Arg  Leu Glu Asn Leu Asp  Asp Leu Arg Val Gln  Val Arg Pro
    1010                1015                1020

Val Pro  His Ser Glu Phe Val  Ser Ser Lys Leu Thr  Glu Lys Leu
    1025                1030                1035

Glu Gln  Gln Leu Arg Asp Ser  Phe Ala Val Ser Thr  Cys Gly Leu
    1040                1045                1050

Pro Pro  Trp Phe Asn Asp Leu  Met Asp Ser Cys Pro  Cys Leu Phe
    1055                1060                1065

Ser Phe  Glu Ala Lys Ser Lys  Tyr Phe Arg Leu Ala  Ala Phe Gly
    1070                1075                1080

Ser Gln  Lys Ile Arg His His  Pro Gln His Leu Ser  Ser Ser Asn
    1085                1090                1095

Val His  Gly Glu Ala Arg Pro  Val Thr Gly Ser Leu  Pro Arg Lys
    1100                1105                1110

Lys Phe  Leu Ala Cys Arg Glu  Asn Ile Leu Glu Ser  Ala Ala Lys
    1115                1120                1125

Met Met  Glu Leu Tyr Gly Asn  Gln Lys Val Val Ile  Glu Val Glu
    1130                1135                1140

Tyr Ser  Glu Glu Val Gly Thr  Gly Leu Gly Pro Thr  Leu Glu Phe
    1145                1150                1155

Tyr Thr  Leu Val Ser Arg Ala  Phe Gln Asn Pro Asp  Leu Gly Met
    1160                1165                1170

Trp Arg  Asn Asp Cys Ser Phe  Ile Val Gly Lys Pro  Val Glu His
    1175                1180                1185
```

| | | | | | | | | | | | |
|---|---|---|---|---|---|---|---|---|---|---|---|
| Ser | Gly | Val | Leu | Ala | Ser | Ser | Gly | Leu | Phe | Pro | Arg | Pro | Trp |
| 1190 | | | | | 1195 | | | | | 1200 | | | |
| Ser | Gly | Thr | Ser | Thr | Thr | Ser | Asp | Val | Leu | Gln | Lys | Phe | Val | Leu |
| 1205 | | | | | 1210 | | | | | 1215 | | | |
| Leu | Gly | Thr | Val | Val | Ala | Lys | Ala | Leu | Gln | Asp | Gly | Arg | Val | Leu |
| 1220 | | | | | 1225 | | | | | 1230 | | | |
| Asp | Leu | Pro | Leu | Ser | Lys | Ala | Phe | Tyr | Lys | Leu | Ile | Leu | Gly | Gln |
| 1235 | | | | | 1240 | | | | | 1245 | | | |
| Glu | Leu | Ser | Ser | Phe | Asp | Ile | His | Phe | Val | Asp | Pro | Glu | Leu | Cys |
| 1250 | | | | | 1255 | | | | | 1260 | | | |
| Lys | Thr | Leu | Val | Glu | Leu | Gln | Ala | Leu | Val | Arg | Arg | Lys | Lys | Leu |
| 1265 | | | | | 1270 | | | | | 1275 | | | |
| Phe | Ala | Glu | Ala | His | Gly | Asp | Ser | Gly | Ala | Ala | Lys | Cys | Asp | Leu |
| 1280 | | | | | 1285 | | | | | 1290 | | | |
| Ser | Phe | His | Gly | Thr | Lys | Ile | Glu | Asp | Leu | Cys | Leu | Glu | Phe | Ala |
| 1295 | | | | | 1300 | | | | | 1305 | | | |
| Leu | Pro | Gly | Tyr | Thr | Asp | Tyr | Asp | Leu | Ala | Pro | Tyr | Ser | Ala | Asn |
| 1310 | | | | | 1315 | | | | | 1320 | | | |
| Asp | Met | Val | Asn | Leu | Asp | Asn | Leu | Glu | Glu | Tyr | Ile | Lys | Gly | Ile |
| 1325 | | | | | 1330 | | | | | 1335 | | | |
| Val | Asn | Ala | Thr | Val | Cys | Asn | Gly | Ile | Gln | Lys | Gln | Val | Glu | Ala |
| 1340 | | | | | 1345 | | | | | 1350 | | | |
| Phe | Arg | Ser | Gly | Phe | Asn | Gln | Val | Phe | Ser | Ile | Glu | His | Leu | Arg |
| 1355 | | | | | 1360 | | | | | 1365 | | | |
| Ile | Phe | Asn | Glu | Glu | Glu | Leu | Glu | Thr | Met | Leu | Cys | Gly | Glu | Cys |
| 1370 | | | | | 1375 | | | | | 1380 | | | |
| Asp | Leu | Phe | Ser | Met | Asn | Glu | Val | Leu | Asp | His | Ile | Lys | Phe | Asp |
| 1385 | | | | | 1390 | | | | | 1395 | | | |
| His | Gly | Tyr | Thr | Ser | Ser | Pro | Pro | Val | Glu | Tyr | Leu | Leu | Gln |
| 1400 | | | | | 1405 | | | | | 1410 | | | |
| Ile | Leu | His | Glu | Phe | Asp | Arg | Glu | Gln | Gln | Arg | Ala | Phe | Leu | Gln |
| 1415 | | | | | 1420 | | | | | 1425 | | | |
| Phe | Val | Thr | Gly | Ser | Pro | Arg | Leu | Pro | His | Gly | Gly | Leu | Ala | Ser |
| 1430 | | | | | 1435 | | | | | 1440 | | | |
| Leu | Ser | Pro | Lys | Leu | Thr | Ile | Val | Arg | Lys | His | Gly | Ser | Asp | Ser |
| 1445 | | | | | 1450 | | | | | 1455 | | | |
| Ser | Asp | Thr | Asp | Leu | Pro | Ser | Val | Met | Thr | Cys | Ala | Asn | Tyr | Leu |
| 1460 | | | | | 1465 | | | | | 1470 | | | |
| Lys | Leu | Pro | Pro | Tyr | Ser | Ser | Lys | Glu | Lys | Met | Lys | Glu | Lys | Leu |
| 1475 | | | | | 1480 | | | | | 1485 | | | |
| Ile | Tyr | Ala | Ile | Thr | Glu | Gly | Gln | Gly | Ser | Phe | His | Leu | Ser |
| 1490 | | | | | 1495 | | | | | 1500 | | | |

<210> SEQ ID NO 3
<211> LENGTH: 5667
<212> TYPE: DNA
<213> ORGANISM: Arabidopsis thaliana

<400> SEQUENCE: 3

| | |
|---|---|
| atggaaactc ggagccgcaa gcgggcggag gcgacctcag ctgccccatc ttcttcttct | 60 |
| tcttctcctc ctcctcctcc ctctgcctct ggtcccacca cccgcagcaa acgcgctcgt | 120 |
| ctttcttctt cttcttcttc ctcacttgcc cccactcctc cttcttcctc caccaccacc | 180 |
| cgctctcgtt cttctcgctc tgccgccgcc gctgctccca tggacacctc caccgactct | 240 |

```
tctggatttc gccgaggcgg acgtggtaac aggggaaaca acaacgataa ttctgacaaa      300
ggtaaggaga aggaacatga cgttaggatt agggagcgtg aaagagaaag agaccgagcc      360
agagaacaac tcaacatgga tgctgccgcc gccgctgcta ggagcgctga cgaggatgac      420
gacaatgaca gtgaggatgg caacggcggt ttcatgcatc ctaacatgag ctctgcgagc      480
agtgctttac aaggcttgct caggaagctc ggtgctggat tggatgactt gcttccttct      540
tccggtatcg gctctgcttc ttcctcccac ttgaatggaa ggatgaagaa gattctctct      600
ggcttgcgcg ctgaaggaga agagggaaaa caggtcgagg ctttaaccca gctttgtgag      660
atgttatcca ttgggaccga agactcgctt agcaccttct ctgttgattc cttcgtccca      720
gttcttgtcg gtctacttaa ccatgaaagc aatcccgaca ttatgcttct tgctgccagg      780
gctcttaccc atctatgtga tgtcttgccg tcttcttgtg ctgctgttgt acattacggg      840
gcagtttcat gcttggtggc cagattgcta accatagaat acatggactt ggcggaacag      900
tctctgcaag ctctcaaaaa gatatctcag gagcacccaa ctgcctgttt gcgagctggt      960
gctcttatgg ctgtgctctc gtatctggat ttcttctcca ctggtgttca gcgcgtagca     1020
ctatctactg ctgccaacat gtgcaagaaa ctaccttctg atgcatctga ttatgttatg     1080
gaagctgtac ctttgctgac aaacctactt cagtatcatg attcgaaggt tttggaatat     1140
gcttctatct gtctgactcg aattgctgaa gcatttgcac cgtatcccga gaaattagat     1200
gaattatgta accatggcct ggtgacgcaa gctgcgtctc ttatttccac gagcaattca     1260
ggaggtgggc aagcatctct tagtgtgtca acatacacgg ggttaatccg attactttct     1320
acctgtgcga gcgggtcacc tcttggattc aggacattac ttcttcttgg tattagtagc     1380
attcttaagg atattctgtt gggttctggg gtctctgcta atgcatctgt atccccagca     1440
ctgagccggc ctgcagatca gatttatgag atagtcaacc tagcgaatga gctcctccct     1500
ccattgccag aaggagttat ctctcttcct actagcacaa cgctcttgt gaaaggttca      1560 tgccaaaaga aatctagtcc aagtacttca ggaaaacaag aagatattct aaaaatttca     1620
ccaagagaaa aattacttgg tgatcaacct gaacttctgc agcagtttgg attggatctt     1680
cttccagttt tagtgcagat ctatggttct agtgtcaatg gtacgattcg ccataaatgt     1740
ctctcagtca ttggaaaagtt gatgtatttc agcagttcag aaatgattca atctctaatt     1800
ggtgacacaa atatttcgag cttcttggct ggtgtcttgg catggaaaga cccacaggtc     1860
ttggttcctg ctctacaagt tgcagagatt ttgatggaaa agcttcctga acattctcg      1920 aaagtgtttg tgagggaagg ggtagtccat gctgtagatc aacttgtctt ggttggtaaa     1980
ccatcccatg cctcacctac tgataaggac aatgactgtg tacccggatc tgcacgatct     2040
aggcgttata gacggcgcag tagtaatgcc aattccgatg gaaaccagtc ggaagagcct     2100
aagaatcctg cgtcccttac catagggca  aaccataatt cccttgatac tcctacagct     2160
agcttcatgc taagggaaac agttagttcc tgcgccaaag cattcaaaga caagtacttc     2220
ccgtctgatg tgggatgt  tgatgttgga gttacagatg atcttttaca tctgaagaat     2280
ctttgcacga agctaactgc tggtatagat gatcataaag tgaaggaa  gggaaaatct      2340 aaagcctctg gccattcct tggcgatttc tctgctagca aggaagagta cttgattggt     2400
gtcatttctg agatacttgg cgagataagt aaaggggatg gtgtctcaac ttttgagttt     2460
attggcagtg gtgtggttgc agcattgctt aactatttt cttgtggata cttttccaaa      2520
gagaagatct ccgaacttaa tttgcccaaa cttcgccagg agggactcag aagggtttaaa    2580 gcttttctag aagtcgctct tccttttgat ggtaatgagg gaaaggtccc tcctatgaca     2640
```

```
gttttgattc agaaacttca aaatgctttta tcgtcactgg agcgctttcc tgttgtcctt   2700
agccatccct caaggtcact aagtggaagt gctcggctct cctcgggttt gagtgctttg   2760
gcacatcctt taaagttgcg attatgccga gcatctggag agaaaacact acgtgattac   2820
tcctccaata ttgtacttat agatccattg caagcttag cagcagtgga ggaatttctg   2880
tggccccgag ttcaacggag tgaatctgct ctgaagccgg cagcgcctat tggcaataca   2940
gagccaggca cgttacctag cggtgctggt gtttcatcac catcttcgtc aactccagct   3000
tcaaccactc gtcgtcattc ttctagatct cgatcggcaa ttaacatcgg tgatacttca   3060
aagaaagatc ctgtgcatga aaaggtacc agctcatcga aggaaaagg taaggcgtt    3120 atgaaaccgg ctcaggcgga taggggcct caaacaagga gcaatgctca aagagagct    3180 gttcttgaca aagatactca aatgaaacca gctagcggag actccagttc tgaggatgag   3240
gaattggaaa tatccccagt cgacattgat gatgccttgg tgattgaaga ggatgacatt   3300
tctgatgatg aagatgatga taatgaagat gttttggatg acagtcttcc catgtgcacg   3360
cctgataaag tccatgatgt gaaattggcg gactcagtgg atgatgatgg tctagcaacc   3420
agcggccgac aaatgaatcc agcttctgga ggcactagtg gagccgcagc agcaagggca   3480
tctgattcta ttgatactgg cattgggaat tcctatggtt ctagaggtgc actctccttt   3540
gctgctgcag cgatggctgg gcttggagct gccagtggta gaggtatcag gggaagtagg   3600
gacttgcatg gacgtaccct aaatcgaagt tcagatgagc cctctaagtt gatatttact   3660
gcggcaggaa acaacttag taggcatttg acgatttatc aggctgtaca gcgacaactt    3720
atgctagatg aagatgatga tgacaggttt ggtggcagtg atctagtctc aagtgatgga   3780
agcagattca atgatattta caccatcatg taccagaggc cagacagcca agtgaatagg   3840
ttgtctgttg gtggagcaag ttctaccaca ccgtcaaaat ccacgaaatc tgctactacc   3900
aattccagtg tagaatctca gtcacatagg gcatctcttt tggatagtat cttacaaggg   3960
gagcttccat gcgaccttga gaagtcgaat tctacatata atgttctggc actgttacgt   4020
gtattagagg gtttaaatca gctttgccct cgtttaagag cccaaactct ttccgatcgt   4080
tttgcagagg gtaaaattac aagtctagat gatctgagta caactgctgc taaggttcct   4140
cttgatgaat tgtcaatag caaacttaca cccaaattgg ctcgacaaat ccaggatgcg    4200
cttgctttgt gcagtggaag tcttccctct tggtgctacc agttgactag agcatgccca   4260
tttttgtttc cgtttcaaac ccggagacag tatttctact cgactgcttt tgggttgtct   4320
cgtgcattga atcgtttgca gcagcagcaa ggtgctgacg gcagtgggtc tacaaatgaa   4380
cgagagatga gaatagggag attgcagcgc cagaaagtcc gtgtatcccg aaataggata   4440
ttagattctg ctgcaaaagt tatggagatg tattctagcc agaaagctgt gcttgaagta   4500
gaatattttg gtgaagttgg tactggtcta ggccctaccc ttgagtttta cacacttcta   4560
agccatgatc tgcaaaaggc ttccctaggg atgtggagat caagttctgg tgacaaggta   4620
tctatgcaaa ttggtagaga tgagattgaa gacggaaaac catctgcagc taacagagat   4680
atagttctgg caccacttgg attgttttcct cggccttggc cctcaacagc tgacatatct   4740
gaaggtggtc agtttcataa agtcattgaa tatttccgcc ttttagggcg tgtgatggcc   4800
aaagcacttc aagatggacg gctattggac gtcccattga gtacagcgtt ttataaactt   4860
attcttggtc aagagcttga tttgcatgat attgtattat ttgacgctga acttggcaag   4920
accttgcaag agctgcgtgt tgttgttgcc cgcaagcact atctggaggg agtaggtggt   4980
```

-continued

```
gacaatagca gcacgatttc tgatttatgt ttacgtggat gccgaataga agatctctcc    5040
ttggaattca cgctacctgg ctatcctgag tacatcctga gatcaggaga tgaaattgtt    5100
gatattacta atcttgagga gtatatatcc cttgtcgttg atgctactgt caagagagga    5160
gtcactcggc agatcgaagc cttcagatct ggattcaatc aggtgtttga cataacatct    5220
ctacaaatat tcaccccttc tgagctggac tatttgctgt gtggtcgtag agagttgtgg    5280
gaggtggaga ctcttgctga acatatcaaa tttgatcatg ggtataatgc caaaagtccg    5340
gcaatcatta acttactgga gatcatggga gaacttacag cagatcagca gagggctttc    5400
tgccaatttg taactggagc tcctaggctt cctcctggtg gcttagctgt tctgaaccca    5460
aagcttacga ttgtgagaaa gcactcatcg acctcaagtg cagcagccaa cggagcaggg    5520
gcttcggaga cagcagatga tgatttgccc agtgtcatga cttgcgcaaa ctaccttaaa    5580
ctccctcctt attctacaaa ggaaatcatg tacaagaaac tgctctacgc catcaacgaa    5640
gggcaaggat cgttcgacct ctcataa                                        5667
```

<210> SEQ ID NO 4
<211> LENGTH: 1888
<212> TYPE: PRT
<213> ORGANISM: Arabidopsis thaliana

<400> SEQUENCE: 4

```
Met Glu Thr Arg Ser Arg Lys Arg Ala Glu Ala Thr Ser Ala Ala Pro
1               5                   10                  15

Ser Ser Ser Ser Ser Ser Pro Pro Pro Pro Ser Ala Ser Gly Pro
            20                  25                  30

Thr Thr Arg Ser Lys Arg Ala Arg Leu Ser Ser Ser Ser Ser Ser
        35                  40                  45

Leu Ala Pro Thr Pro Pro Ser Ser Ser Thr Thr Thr Arg Ser Arg Ser
    50                  55                  60

Ser Arg Ser Ala Ala Ala Ala Pro Met Asp Thr Ser Thr Asp Ser
65                  70                  75                  80

Ser Gly Phe Arg Arg Gly Gly Arg Gly Asn Arg Gly Asn Asn Asn Asp
                85                  90                  95

Asn Ser Asp Lys Gly Lys Glu Lys Glu His Asp Val Arg Ile Arg Glu
            100                 105                 110

Arg Glu Arg Glu Arg Asp Arg Ala Arg Glu Gln Leu Asn Met Asp Ala
        115                 120                 125

Ala Ala Ala Ala Ala Arg Ser Ala Asp Glu Asp Asp Asn Asp Ser
    130                 135                 140

Glu Asp Gly Asn Gly Gly Phe Met His Pro Asn Met Ser Ser Ala Ser
145                 150                 155                 160

Ser Ala Leu Gln Gly Leu Leu Arg Lys Leu Gly Ala Gly Leu Asp Asp
                165                 170                 175

Leu Leu Pro Ser Ser Gly Ile Gly Ser Ala Ser Ser His Leu Asn
            180                 185                 190

Gly Arg Met Lys Lys Ile Leu Ser Gly Leu Arg Ala Glu Gly Glu Glu
        195                 200                 205

Gly Lys Gln Val Glu Ala Leu Thr Gln Leu Cys Glu Met Leu Ser Ile
    210                 215                 220

Gly Thr Glu Asp Ser Leu Ser Thr Phe Ser Val Asp Ser Phe Val Pro
225                 230                 235                 240

Val Leu Val Gly Leu Leu Asn His Glu Ser Asn Pro Asp Ile Met Leu
                245                 250                 255
```

```
Leu Ala Ala Arg Ala Leu Thr His Leu Cys Asp Val Leu Pro Ser Ser
            260                 265                 270
Cys Ala Ala Val Val His Tyr Gly Ala Val Ser Cys Leu Val Ala Arg
            275                 280                 285
Leu Leu Thr Ile Glu Tyr Met Asp Leu Ala Glu Gln Ser Leu Gln Ala
290                 295                 300
Leu Lys Lys Ile Ser Gln Glu His Pro Thr Ala Cys Leu Arg Ala Gly
305                 310                 315                 320
Ala Leu Met Ala Val Leu Ser Tyr Leu Asp Phe Phe Ser Thr Gly Val
                325                 330                 335
Gln Arg Val Ala Leu Ser Thr Ala Ala Asn Met Cys Lys Lys Leu Pro
            340                 345                 350
Ser Asp Ala Ser Asp Tyr Val Met Glu Ala Val Pro Leu Leu Thr Asn
            355                 360                 365
Leu Leu Gln Tyr His Asp Ser Lys Val Leu Glu Tyr Ala Ser Ile Cys
370                 375                 380
Leu Thr Arg Ile Ala Glu Ala Phe Ala Pro Tyr Pro Glu Lys Leu Asp
385                 390                 395                 400
Glu Leu Cys Asn His Gly Leu Val Thr Gln Ala Ala Ser Leu Ile Ser
                405                 410                 415
Thr Ser Asn Ser Gly Gly Gly Gln Ala Ser Leu Ser Val Ser Thr Tyr
            420                 425                 430
Thr Gly Leu Ile Arg Leu Leu Ser Thr Cys Ala Ser Gly Ser Pro Leu
            435                 440                 445
Gly Phe Arg Thr Leu Leu Leu Gly Ile Ser Ser Ile Leu Lys Asp
            450                 455                 460
Ile Leu Leu Gly Ser Gly Val Ser Ala Asn Ala Ser Val Ser Pro Ala
465                 470                 475                 480
Leu Ser Arg Pro Ala Asp Gln Ile Tyr Glu Ile Val Asn Leu Ala Asn
            485                 490                 495
Glu Leu Leu Pro Pro Leu Pro Glu Gly Val Ile Ser Leu Pro Thr Ser
            500                 505                 510
Thr Asn Ala Leu Val Lys Gly Ser Cys Gln Lys Ser Ser Pro Ser
            515                 520                 525
Thr Ser Gly Lys Gln Glu Asp Ile Leu Lys Ile Ser Pro Arg Glu Lys
530                 535                 540
Leu Leu Gly Asp Gln Pro Glu Leu Leu Gln Gln Phe Gly Leu Asp Leu
545                 550                 555                 560
Leu Pro Val Leu Val Gln Ile Tyr Gly Ser Ser Val Asn Gly Thr Ile
                565                 570                 575
Arg His Lys Cys Leu Ser Val Ile Gly Lys Leu Met Tyr Phe Ser Ser
            580                 585                 590
Ser Glu Met Ile Gln Ser Leu Ile Gly Asp Thr Asn Ile Ser Ser Phe
            595                 600                 605
Leu Ala Gly Val Leu Ala Trp Lys Asp Pro Gln Val Leu Val Pro Ala
            610                 615                 620
Leu Gln Val Ala Glu Ile Leu Met Glu Lys Leu Pro Glu Thr Phe Ser
625                 630                 635                 640
Lys Val Phe Val Arg Glu Gly Val Val His Ala Val Asp Gln Leu Val
                645                 650                 655
Leu Val Gly Lys Pro Ser His Ala Ser Pro Thr Asp Lys Asp Asn Asp
            660                 665                 670
```

```
Cys Val Pro Gly Ser Ala Arg Ser Arg Tyr Arg Arg Ser Ser
            675                 680                 685

Asn Ala Asn Ser Asp Gly Asn Gln Ser Glu Glu Pro Lys Asn Pro Ala
        690                 695                 700

Ser Leu Thr Ile Gly Ala Asn His Asn Ser Leu Asp Thr Pro Thr Ala
705                 710                 715                 720

Ser Phe Met Leu Arg Glu Thr Val Ser Ser Cys Ala Lys Ala Phe Lys
                725                 730                 735

Asp Lys Tyr Phe Pro Ser Asp Gly Asp Val Asp Val Gly Val Thr
            740                 745                 750

Asp Asp Leu Leu His Leu Lys Asn Leu Cys Thr Lys Leu Thr Ala Gly
        755                 760                 765

Ile Asp Asp His Lys Val Lys Gly Lys Gly Lys Ser Lys Ala Ser Gly
770                 775                 780

Pro Phe Leu Gly Asp Phe Ser Ala Ser Lys Glu Glu Tyr Leu Ile Gly
785                 790                 795                 800

Val Ile Ser Glu Ile Leu Gly Glu Ile Ser Lys Gly Asp Gly Val Ser
            805                 810                 815

Thr Phe Glu Phe Ile Gly Ser Gly Val Val Ala Ala Leu Leu Asn Tyr
        820                 825                 830

Phe Ser Cys Gly Tyr Phe Ser Lys Glu Lys Ile Ser Glu Leu Asn Leu
    835                 840                 845

Pro Lys Leu Arg Gln Glu Gly Leu Arg Arg Phe Lys Ala Phe Leu Glu
        850                 855                 860

Val Ala Leu Pro Phe Asp Gly Asn Glu Gly Lys Val Pro Pro Met Thr
865                 870                 875                 880

Val Leu Ile Gln Lys Leu Gln Asn Ala Leu Ser Ser Leu Glu Arg Phe
            885                 890                 895

Pro Val Val Leu Ser His Pro Ser Arg Ser Leu Ser Gly Ser Ala Arg
                900                 905                 910

Leu Ser Ser Gly Leu Ser Ala Leu Ala His Pro Leu Lys Leu Arg Leu
        915                 920                 925

Cys Arg Ala Ser Gly Glu Lys Thr Leu Arg Asp Tyr Ser Ser Asn Ile
    930                 935                 940

Val Leu Ile Asp Pro Leu Ala Ser Leu Ala Ala Val Glu Glu Phe Leu
945                 950                 955                 960

Trp Pro Arg Val Gln Arg Ser Glu Ser Ala Leu Lys Pro Ala Ala Pro
                965                 970                 975

Ile Gly Asn Thr Glu Pro Gly Thr Leu Pro Ser Gly Ala Gly Val Ser
        980                 985                 990

Ser Pro Ser Ser Ser Thr Pro Ala Ser Thr Thr Arg Arg His Ser Ser
    995                 1000                1005

Arg Ser Arg Ser Ala Ile Asn Ile Gly Asp Thr Ser Lys Lys Asp
    1010                1015                1020

Pro Val His Glu Lys Gly Thr Ser Ser Lys Gly Lys Gly Lys
    1025                1030                1035

Gly Val Met Lys Pro Ala Gln Ala Asp Lys Gly Pro Gln Thr Arg
    1040                1045                1050

Ser Asn Ala Gln Lys Arg Ala Val Leu Asp Lys Asp Thr Gln Met
    1055                1060                1065

Lys Pro Ala Ser Gly Asp Ser Ser Glu Asp Glu Glu Leu Glu
    1070                1075                1080

Ile Ser Pro Val Asp Ile Asp Asp Ala Leu Val Ile Glu Glu Asp
```

```
            1085                1090                1095
Asp Ile Ser Asp Asp Glu Asp Asp Asn Glu Asp Val Leu Asp
            1100                1105                1110

Asp Ser Leu Pro Met Cys Thr Pro Asp Lys Val His Asp Val Lys
            1115                1120                1125

Leu Ala Asp Ser Val Asp Asp Gly Leu Ala Thr Ser Gly Arg
            1130                1135                1140

Gln Met Asn Pro Ala Ser Gly Gly Thr Ser Gly Ala Ala Ala
            1145                1150                1155

Arg Ala Ser Asp Ser Ile Asp Thr Gly Ile Gly Asn Ser Tyr Gly
            1160                1165                1170

Ser Arg Gly Ala Leu Ser Phe Ala Ala Ala Met Ala Gly Leu
            1175                1180                1185

Gly Ala Ala Ser Gly Arg Gly Ile Arg Gly Ser Arg Asp Leu His
            1190                1195                1200

Gly Arg Thr Leu Asn Arg Ser Ser Asp Glu Pro Ser Lys Leu Ile
            1205                1210                1215

Phe Thr Ala Ala Gly Lys Gln Leu Ser Arg His Leu Thr Ile Tyr
            1220                1225                1230

Gln Ala Val Gln Arg Gln Leu Met Leu Asp Glu Asp Asp Asp Asp
            1235                1240                1245

Arg Phe Gly Gly Ser Asp Leu Val Ser Ser Asp Gly Ser Arg Phe
            1250                1255                1260

Asn Asp Ile Tyr Thr Ile Met Tyr Gln Arg Pro Asp Ser Gln Val
            1265                1270                1275

Asn Arg Leu Ser Val Gly Gly Ala Ser Ser Thr Thr Pro Ser Lys
            1280                1285                1290

Ser Thr Lys Ser Ala Thr Thr Asn Ser Ser Val Glu Ser Gln Ser
            1295                1300                1305

His Arg Ala Ser Leu Leu Asp Ser Ile Leu Gln Gly Glu Leu Pro
            1310                1315                1320

Cys Asp Leu Glu Lys Ser Asn Ser Thr Tyr Asn Val Leu Ala Leu
            1325                1330                1335

Leu Arg Val Leu Glu Gly Leu Asn Gln Leu Cys Pro Arg Leu Arg
            1340                1345                1350

Ala Gln Thr Leu Ser Asp Arg Phe Ala Glu Gly Lys Ile Thr Ser
            1355                1360                1365

Leu Asp Asp Leu Ser Thr Thr Ala Ala Lys Val Pro Leu Asp Glu
            1370                1375                1380

Phe Val Asn Ser Lys Leu Thr Pro Lys Leu Ala Arg Gln Ile Gln
            1385                1390                1395

Asp Ala Leu Ala Leu Cys Ser Gly Ser Leu Pro Ser Trp Cys Tyr
            1400                1405                1410

Gln Leu Thr Arg Ala Cys Pro Phe Leu Phe Pro Phe Gln Thr Arg
            1415                1420                1425

Arg Gln Tyr Phe Tyr Ser Thr Ala Phe Gly Leu Ser Arg Ala Leu
            1430                1435                1440

Asn Arg Leu Gln Gln Gln Gln Gly Ala Asp Gly Ser Gly Ser Thr
            1445                1450                1455

Asn Glu Arg Glu Met Arg Ile Gly Arg Leu Gln Arg Gln Lys Val
            1460                1465                1470

Arg Val Ser Arg Asn Arg Ile Leu Asp Ser Ala Ala Lys Val Met
            1475                1480                1485
```

-continued

```
Glu Met Tyr Ser Ser Gln Lys Ala Val Leu Glu Val Glu Tyr Phe
    1490                1495                1500

Gly Glu Val Gly Thr Gly Leu Gly Pro Thr Leu Glu Phe Tyr Thr
    1505                1510                1515

Leu Leu Ser His Asp Leu Gln Lys Ala Ser Leu Gly Met Trp Arg
    1520                1525                1530

Ser Ser Ser Gly Asp Lys Val Ser Met Gln Ile Gly Arg Asp Glu
    1535                1540                1545

Ile Glu Asp Gly Lys Pro Ser Ala Ala Asn Arg Asp Ile Val Leu
    1550                1555                1560

Ala Pro Leu Gly Leu Phe Pro Arg Pro Trp Pro Ser Thr Ala Asp
    1565                1570                1575

Ile Ser Glu Gly Gly Gln Phe His Lys Val Ile Glu Tyr Phe Arg
    1580                1585                1590

Leu Leu Gly Arg Val Met Ala Lys Ala Leu Gln Asp Gly Arg Leu
    1595                1600                1605

Leu Asp Val Pro Leu Ser Thr Ala Phe Tyr Lys Leu Ile Leu Gly
    1610                1615                1620

Gln Glu Leu Asp Leu His Asp Ile Val Leu Phe Asp Ala Glu Leu
    1625                1630                1635

Gly Lys Thr Leu Gln Glu Leu Arg Val Val Val Ala Arg Lys His
    1640                1645                1650

Tyr Leu Glu Gly Val Gly Gly Asp Asn Ser Ser Thr Ile Ser Asp
    1655                1660                1665

Leu Cys Leu Arg Gly Cys Arg Ile Glu Asp Leu Ser Leu Glu Phe
    1670                1675                1680

Thr Leu Pro Gly Tyr Pro Glu Tyr Ile Leu Arg Ser Gly Asp Glu
    1685                1690                1695

Ile Val Asp Ile Thr Asn Leu Glu Glu Tyr Ile Ser Leu Val Val
    1700                1705                1710

Asp Ala Thr Val Lys Arg Gly Val Thr Arg Gln Ile Glu Ala Phe
    1715                1720                1725

Arg Ser Gly Phe Asn Gln Val Phe Asp Ile Thr Ser Leu Gln Ile
    1730                1735                1740

Phe Thr Pro Ser Glu Leu Asp Tyr Leu Leu Cys Gly Arg Arg Glu
    1745                1750                1755

Leu Trp Glu Val Glu Thr Leu Ala Glu His Ile Lys Phe Asp His
    1760                1765                1770

Gly Tyr Asn Ala Lys Ser Pro Ala Ile Ile Asn Leu Leu Glu Ile
    1775                1780                1785

Met Gly Glu Leu Thr Ala Asp Gln Gln Arg Ala Phe Cys Gln Phe
    1790                1795                1800

Val Thr Gly Ala Pro Arg Leu Pro Pro Gly Gly Leu Ala Val Leu
    1805                1810                1815

Asn Pro Lys Leu Thr Ile Val Arg Lys His Ser Ser Thr Ser Ser
    1820                1825                1830

Ala Ala Ala Asn Gly Ala Gly Ala Ser Glu Thr Ala Asp Asp Asp
    1835                1840                1845

Leu Pro Ser Val Met Thr Cys Ala Asn Tyr Leu Lys Leu Pro Pro
    1850                1855                1860

Tyr Ser Thr Lys Glu Ile Met Tyr Lys Lys Leu Leu Tyr Ala Ile
    1865                1870                1875
```

Asn Glu Gly Gln Gly Ser Phe Asp Leu Ser
    1880             1885

<210> SEQ ID NO 5
<211> LENGTH: 4524
<212> TYPE: DNA
<213> ORGANISM: Brassica rapa

<400> SEQUENCE: 5

| | | | | | |
|---|---|---|---|---|---|
| atggagaaca | gggggcagaa | acgaatggag | gatgtggagg | agctacctgc | tgataagaga | 60 |
| gcttgtaact | cacaggactc | taggtcaagc | tcatctggtg | gctcgtctgt | tcagagccag | 120 |
| tctcaagaag | cagccaatgg | agcgagctcg | ggacacgaaa | ccactgacgc | tgatatggac | 180 |
| acttcttcat | cagattctcc | ttctagtcat | tcagatggag | agccagacaa | ggaggaggag | 240 |
| gaggaggagg | actacggatc | ttgcgattct | gatgatgatg | atgaagaagg | tgaagatccg | 300 |
| aggcacaagg | cgcttcagga | tgttcagtgg | gggagatcgt | ctgaggatca | gcagaagttg | 360 |
| agttctcttg | tgacgagatt | gagtgaagaa | gtcgatcctt | ctttgcagtt | gactggtctt | 420 |
| acggagctgt | gtgaggtctt | gtctttctgt | actgaagatt | cgctgtccac | cgttatggcc | 480 |
| gatacgcttt | cccgggtgct | tgttaagttg | gctaatcatg | agagcaatgc | agatattatg | 540 |
| ctgcttgcta | tcagagcggt | tacttacttg | tctgatgttt | atccgcggtc | tgtagcattc | 600 |
| cttgtgaaac | atgagactct | ccctgctctt | tgccagagac | tacaggcaat | tgagtacttg | 660 |
| gacgttgctg | agcagtgttt | gcaagcactt | gagaaaatat | ccaaagatga | gccagtggcg | 720 |
| tgcttgaatg | ctggagcaat | taaggcagtg | ctttcgtata | ttgatttctt | ctcaactagc | 780 |
| ttacagagag | tcgcagtttc | tactgtggtg | aatatatgta | ggaagctttc | atctgagtct | 840 |
| ccctccccctt | ttatggatgc | tgttccaatt | ttatgcaatc | ttcttcagta | tgaagatcga | 900 |
| cagttggtgg | aaaatgtggc | tatttgctta | acaaaaatag | cagatcaagt | tagcgagtca | 960 |
| cctgaaatgt | tggatcaact | atctagccat | ggtctgattc | atcaatccat | acatctttta | 1020 |
| aacttgaatg | gccgcaccac | cctatctcaa | cctgtttaca | atggtgtgat | tggattgcta | 1080 |
| agaaaactat | cttctggttc | aattttagcc | ttcagaacgt | tatatgaact | taacattggc | 1140 |
| tacagactaa | aagaaattat | atccacgtat | gacatttccc | attcagtgtc | ttctacacat | 1200 |
| cccaacaata | catgttccaa | ccaggtgcat | gaagtcctga | agttggtgat | tgagcttctt | 1260 |
| ccatcttcgc | ctgtagagga | taatcagctg | gcattggaaa | aggaaagttt | tcttgttaat | 1320 |
| cagcccgatc | tcttgcaaca | atttggagca | gacatacttc | ctgttatgat | tcaggtgcta | 1380 |
| aaatctggag | cgaacgtata | tgttttttat | ggttgcctat | cagcaatcca | caagctgact | 1440 |
| tgcttgagta | agtcagtcga | ttttgtcgat | ttactgaaga | atgcaaacat | tttaagtgtt | 1500 |
| ttggcgggca | ttttgtcaag | gaaagttcat | catgtggttg | ttgtagcact | acagattgct | 1560 |
| gaagcgcttc | ttgggaaata | cagtgatgat | tttttgaatt | cgtttataaa | ggagggtgtt | 1620 |
| tatttcgcaa | ttgaagcgct | tttaaactcg | gggcaacaga | tcaaggatc | agctgacggt | 1680 |
| tcagaagagc | atgttccgaa | agagactgtg | aaatgcttgt | gccagtcttt | tgaaagatcg | 1740 |
| agttcctctt | cttcacaaac | ttgtaagatc | gagaaggatt | ctgtctacat | tctcgcaaca | 1800 |
| cgtatcaagg | agagtttctt | tggacctgag | gtattcgact | ctcagaaagg | cttgacagat | 1860 |
| gttctccaga | acctcaagca | cttgtctgca | gcacttgacg | atttgatgac | tgaacctatt | 1920 |
| gatgcacatg | ccctgcacga | tgagaagttc | ttctcagtat | ggagccaaat | catggaaagg | 1980 |
| ctgaatggaa | gggaatctgt | gtccacattt | gaatttacag | agagtggagt | tgtgaaggca | 2040 |

```
ctgacaaatt acctgtctaa tagactccac caaaggaaat ttagcaaagg cgattcagaa    2100
tgtgatagtt tgccatttgt tggtaacaga tttgaagtgt tcacaagatc actttggtct    2160
gatggcgagg caacttcatc cgtattaata aagaatctcc aaaattcctt atcttcatta    2220
gagaactacc caattgtcct aagccagttt ttgaagcaaa ggaactcatt cgcgactgtt    2280
cccaatggac gtagcataag ctatccaatc ctaagagttc gttttgtcaa agcagagggg    2340
gagacttgct tgcgtgatta ctcccaagac ttggtcaccg ttgacccact ttgcttcttg    2400
gatgctgtcg atcaatacat gtggcctaaa gtgcagttag aacctttata ttccgttgaa    2460
gaaaaagatc aagctatgga atgtccatct tctcagctgg agtcaacttc tatatcttgt    2520
caaggtgaaa gctcaaccca tatggagatt gacagtccta acgcatctca gttgcaggga    2580
tctcaagagg aagaccaaga gcagcttcca gattcagggg aagataatac ttcctcatct    2640
gaagaggagg atgcgttacc tgaggaggat gcgttaccta gacttttgtt tcgtctagaa    2700
gggcttgaac tagaccgctc tttgactgta taccaggcta ttctcttgca caaactaaaa    2760
tcaggaagtg aaactaccaa cgattccaag ctgagtggat cccacaccat cacgtatgaa    2820
agggccccac aacttgcaga gtctgatgaa aatctgtttc ctctcggatt tatggacaat    2880
gacgagtatc acccgttttt atccttcttg tttgctcaaa gacttgattt gcgccacaaa    2940
gcaacaaatc ctcctgcgta cgacatgttg tttctgctca agagtctgga gggcatgaac    3000
agatttctct ttcacctgat tgtcatgaaa cggataaatg cttttgggga aggtaggctg    3060
gagaatttgg atgatctgag ggtgcagctt cgtcctgtgc catatgctga atttgttagt    3120
agtaagctaa cagagaagct ggagcagcag ctgcgtgatt cctttgctgt gtcaacctgc    3180
ggtctaccac cgtggtttaa tgatctaatg ggttcatgcc cttttctgtt tagttttgaa    3240
gtcaaaacca aatacttccg gctagcagca ttcggttcgc agaaagtcca tcatcatcca    3300
caacacctta gcagtgaagg gcgcccagta actggtagtt tacctcgcaa aaagttctta    3360
gcttgccgtg aaaccattct agagtctgct tcaaaaatga tggagttgca cggcaaccag    3420
aaggtggtaa ttgaggttga gtacagtgaa gaagtgggaa ctggtcttgg gccaacgctg    3480
gagttctaca cacttgtcag tagagcgttt caaaatccag accttggcat gtggaggtgt    3540
gatcgtagtt cctttgctgg aaaaccaaag gaagactcag gatttttggt ggctccttcg    3600
ggactctttc cacgaccttg gtcagataca tcagctgctt tcccagatgt gctacagaaa    3660
tttgtgctct tagggacagt ggtagcaaag gctctacatg atggacgagt tttggacatt    3720
cctttctcca aagccttcta taaactgatt atcggacagg agttgagttc atttgacatc    3780
cacttcattg accctgaact ttgtaaaaca ctggtggaat tgcaagctct gacacgtagg    3840
aaaaaggttt tctcagaatc acaaactgat gcccgagcag ccaagtgtga tttgagtttc    3900
cgtggaacaa atattgagga tctttgtctt gaatttgtgc tgcctggcta cacagactat    3960
gttctcgctc ttcattctgc taatgatatg gtaaatttgg ataacctcga ggagtatatc    4020
aaggctattg tcaatgcaac aatatgtaac gggatccaaa acaagtggaa agcatttcgg    4080
tctggattta caaagttttt ccctattgaa catcttggga tattcaatga agaagaactg    4140
gaaactctct tgtgtggaga acgagatctc tttaatatga atgaagtctt ggatcacatc    4200
aagtttgatc atggatatac ttctagcagc ccaccagttg aaaatttgtt ggagattctg    4260
catgagtttg acaaggatca acaacgagcc tttctgcagt ttgtaacagg atgtcctcgt    4320
ctacctcctg ggggcttggc gtctctcaat cccaaactaa caattgtccg caagcgtggt    4380
agcgattctt cagaaactga cttgccgagt gtgatgacat gcgctaatta tctaaagctt    4440
```
ccaccttact cttccaaaga aaagatgaag gagaagctaa tttatgctat aactgaaggc    4500
caaggttcct tccatctctc ttaa                                           4524

<210> SEQ ID NO 6
<211> LENGTH: 1507
<212> TYPE: PRT
<213> ORGANISM: Brassica rapa

<400> SEQUENCE: 6

Met Glu Asn Arg Gly Gln Lys Arg Met Glu Asp Val Glu Glu Leu Pro
1               5                   10                  15

Ala Asp Lys Arg Ala Cys Asn Ser Gln Asp Ser Arg Ser Ser Ser Ser
            20                  25                  30

Gly Gly Ser Ser Val Gln Ser Gln Ser Gln Glu Ala Ala Asn Gly Ala
        35                  40                  45

Ser Ser Gly His Glu Thr Thr Asp Ala Asp Met Asp Thr Ser Ser Ser
    50                  55                  60

Asp Ser Pro Ser Ser His Ser Asp Gly Glu Pro Asp Lys Glu Glu Glu
65                  70                  75                  80

Glu Glu Glu Asp Tyr Gly Ser Cys Asp Ser Asp Asp Asp Glu Glu
                85                  90                  95

Gly Glu Asp Pro Arg His Lys Ala Leu Gln Asp Val Gln Trp Gly Arg
            100                 105                 110

Ser Ser Glu Asp Gln Gln Lys Leu Ser Ser Leu Val Thr Arg Leu Ser
        115                 120                 125

Glu Glu Val Asp Pro Ser Leu Gln Leu Thr Gly Leu Thr Glu Leu Cys
    130                 135                 140

Glu Val Leu Ser Phe Cys Thr Glu Asp Ser Leu Ser Thr Val Met Ala
145                 150                 155                 160

Asp Thr Leu Ser Arg Val Leu Val Lys Leu Ala Asn His Glu Ser Asn
                165                 170                 175

Ala Asp Ile Met Leu Leu Ala Ile Arg Ala Val Thr Tyr Leu Ser Asp
            180                 185                 190

Val Tyr Pro Arg Ser Val Ala Phe Leu Val Lys His Glu Thr Leu Pro
        195                 200                 205

Ala Leu Cys Gln Arg Leu Gln Ala Ile Glu Tyr Leu Asp Val Ala Glu
    210                 215                 220

Gln Cys Leu Gln Ala Leu Glu Lys Ile Ser Lys Asp Glu Pro Val Ala
225                 230                 235                 240

Cys Leu Asn Ala Gly Ala Ile Lys Ala Val Leu Ser Tyr Ile Asp Phe
                245                 250                 255

Phe Ser Thr Ser Leu Gln Arg Val Ala Val Ser Thr Val Val Asn Ile
            260                 265                 270

Cys Arg Lys Leu Ser Ser Glu Ser Pro Ser Phe Met Asp Ala Val
        275                 280                 285

Pro Ile Leu Cys Asn Leu Leu Gln Tyr Glu Asp Arg Gln Leu Val Glu
    290                 295                 300

Asn Val Ala Ile Cys Leu Thr Lys Ile Ala Asp Gln Val Ser Glu Ser
305                 310                 315                 320

Pro Glu Met Leu Asp Gln Leu Ser Ser His Gly Leu Ile His Gln Ser
                325                 330                 335

Ile His Leu Leu Asn Leu Asn Gly Arg Thr Thr Leu Ser Gln Pro Val
            340                 345                 350

```
Tyr Asn Gly Val Ile Gly Leu Leu Arg Lys Leu Ser Ser Gly Ser Ile
            355                 360                 365

Leu Ala Phe Arg Thr Leu Tyr Glu Leu Asn Ile Gly Tyr Arg Leu Lys
    370                 375                 380

Glu Ile Ile Ser Thr Tyr Asp Ile Ser His Ser Val Ser Ser Thr His
385                 390                 395                 400

Pro Asn Asn Thr Cys Ser Asn Gln Val His Glu Val Leu Lys Leu Val
                405                 410                 415

Ile Glu Leu Leu Pro Ser Ser Pro Val Glu Asp Asn Gln Leu Ala Leu
            420                 425                 430

Glu Lys Glu Ser Phe Leu Val Asn Gln Pro Asp Leu Leu Gln Gln Phe
        435                 440                 445

Gly Ala Asp Ile Leu Pro Val Met Ile Gln Val Leu Lys Ser Gly Ala
    450                 455                 460

Asn Val Tyr Val Phe Tyr Gly Cys Leu Ser Ala Ile His Lys Leu Thr
465                 470                 475                 480

Cys Leu Ser Lys Ser Val Asp Phe Val Asp Leu Leu Lys Asn Ala Asn
                485                 490                 495

Ile Leu Ser Val Leu Ala Gly Ile Leu Ser Arg Lys Val His His Val
            500                 505                 510

Val Val Val Ala Leu Gln Ile Ala Glu Ala Leu Leu Gly Lys Tyr Ser
        515                 520                 525

Asp Asp Phe Leu Asn Ser Phe Ile Lys Glu Gly Val Tyr Phe Ala Ile
    530                 535                 540

Glu Ala Leu Leu Asn Ser Gly Gln Gln Asn Gln Gly Ser Ala Asp Gly
545                 550                 555                 560

Ser Glu Glu His Val Pro Lys Glu Thr Val Lys Cys Leu Cys Gln Ser
                565                 570                 575

Phe Glu Arg Ser Ser Ser Ser Ser Gln Thr Cys Lys Ile Glu Lys
            580                 585                 590

Asp Ser Val Tyr Ile Leu Ala Thr Arg Ile Lys Glu Ser Phe Phe Gly
        595                 600                 605

Pro Glu Val Phe Asp Ser Gln Lys Gly Leu Thr Asp Val Leu Gln Asn
    610                 615                 620

Leu Lys His Leu Ser Ala Ala Leu Asp Asp Leu Met Thr Glu Pro Ile
625                 630                 635                 640

Asp Ala His Ala Leu His Asp Glu Lys Phe Phe Ser Val Trp Ser Gln
                645                 650                 655

Ile Met Glu Arg Leu Asn Gly Arg Glu Ser Val Ser Thr Phe Glu Phe
            660                 665                 670

Thr Glu Ser Gly Val Val Lys Ala Leu Thr Asn Tyr Leu Ser Asn Arg
        675                 680                 685

Leu His Gln Arg Lys Phe Ser Lys Gly Asp Ser Glu Cys Asp Ser Leu
    690                 695                 700

Pro Phe Val Gly Asn Arg Phe Glu Val Phe Thr Arg Ser Leu Trp Ser
705                 710                 715                 720

Asp Gly Glu Ala Thr Ser Ser Val Leu Ile Lys Asn Leu Gln Asn Ser
                725                 730                 735

Leu Ser Ser Leu Glu Asn Tyr Pro Ile Val Leu Ser Gln Phe Leu Lys
            740                 745                 750

Gln Arg Asn Ser Phe Ala Thr Val Pro Asn Gly Arg Ser Ile Ser Tyr
        755                 760                 765

Pro Ile Leu Arg Val Arg Phe Val Lys Ala Glu Gly Glu Thr Cys Leu
```

```
                770             775             780
Arg Asp Tyr Ser Gln Asp Leu Thr Val Asp Pro Leu Cys Phe Leu
785             790             795             800

Asp Ala Val Asp Gln Tyr Met Trp Pro Lys Val Gln Leu Glu Pro Leu
            805             810             815

Tyr Ser Val Glu Glu Lys Asp Gln Ala Met Glu Cys Pro Ser Ser Gln
            820             825             830

Leu Glu Ser Thr Ser Ile Ser Cys Gln Gly Glu Ser Ser Thr His Met
            835             840             845

Glu Ile Asp Ser Pro Asn Ala Ser Gln Leu Gln Gly Ser Gln Glu Glu
            850             855             860

Asp Gln Glu Gln Leu Pro Asp Ser Gly Glu Asp Asn Thr Ser Ser Ser
865             870             875             880

Glu Glu Glu Asp Ala Leu Pro Glu Glu Asp Ala Leu Pro Arg Leu Leu
            885             890             895

Phe Arg Leu Glu Gly Leu Glu Leu Asp Arg Ser Leu Thr Val Tyr Gln
            900             905             910

Ala Ile Leu Leu His Lys Leu Lys Ser Gly Ser Glu Thr Thr Asn Asp
            915             920             925

Ser Lys Leu Ser Gly Ser His Thr Ile Thr Tyr Glu Arg Ala Pro Gln
930             935             940

Leu Ala Glu Ser Asp Glu Asn Leu Phe Pro Leu Gly Phe Met Asp Asn
945             950             955             960

Asp Glu Tyr His Pro Phe Leu Ser Phe Leu Ala Gln Arg Leu Asp
            965             970             975

Leu Arg His Lys Ala Thr Asn Pro Pro Ala Tyr Asp Met Leu Phe Leu
            980             985             990

Leu Lys Ser Leu Glu Gly Met Asn Arg Phe Leu Phe His Leu Ile Cys
            995             1000            1005

His Glu Arg Ile Asn Ala Phe Gly Glu Gly Arg Leu Glu Asn Leu
    1010            1015            1020

Asp Asp Leu Arg Val Gln Leu Arg Pro Val Pro Tyr Ala Glu Phe
    1025            1030            1035

Val Ser Ser Lys Leu Thr Glu Lys Leu Glu Gln Gln Leu Arg Asp
    1040            1045            1050

Ser Phe Ala Val Ser Thr Cys Gly Leu Pro Pro Trp Phe Asn Asp
    1055            1060            1065

Leu Met Gly Ser Cys Pro Phe Leu Phe Ser Phe Glu Val Lys Thr
    1070            1075            1080

Lys Tyr Phe Arg Leu Ala Ala Phe Gly Ser Gln Lys Val His His
    1085            1090            1095

His Pro Gln His Leu Ser Ser Glu Gly Arg Pro Val Thr Gly Ser
    1100            1105            1110

Leu Pro Arg Lys Lys Phe Leu Ala Cys Arg Glu Thr Ile Leu Glu
    1115            1120            1125

Ser Ala Ser Lys Met Met Glu Leu His Gly Asn Gln Lys Val Val
    1130            1135            1140

Ile Glu Val Glu Tyr Ser Glu Val Gly Thr Gly Leu Gly Pro
    1145            1150            1155

Thr Leu Glu Phe Tyr Thr Leu Val Ser Arg Ala Phe Gln Asn Pro
    1160            1165            1170

Asp Leu Gly Met Trp Arg Cys Asp Arg Ser Ser Phe Ala Gly Lys
    1175            1180            1185
```

| Pro | Lys<br>1190 | Glu | Asp | Ser | Gly<br>1195 | Phe | Leu | Val | Ala | Pro<br>1200 | Ser | Gly | Leu | Phe |

| Pro | Arg<br>1205 | Pro | Trp | Ser | Asp<br>1210 | Thr | Ser | Ala | Ala | Phe<br>1215 | Pro | Asp | Val | Leu |

| Gln | Lys<br>1220 | Phe | Val | Leu | Leu<br>1225 | Gly | Thr | Val | Val | Ala<br>1230 | Lys | Ala | Leu | His |

| Asp | Gly<br>1235 | Arg | Val | Leu | Asp<br>1240 | Ile | Pro | Phe | Ser | Lys<br>1245 | Ala | Phe | Tyr | Lys |

| Leu | Ile<br>1250 | Ile | Gly | Gln | Glu<br>1255 | Leu | Ser | Ser | Phe | Asp<br>1260 | Ile | His | Phe | Ile |

| Asp | Pro<br>1265 | Glu | Leu | Cys | Lys<br>1270 | Thr | Leu | Val | Glu | Leu<br>1275 | Gln | Ala | Leu | Thr |

| Arg | Arg<br>1280 | Lys | Lys | Val | Phe<br>1285 | Ser | Glu | Ser | Gln | Thr<br>1290 | Asp | Ala | Arg | Ala |

| Ala | Lys<br>1295 | Cys | Asp | Leu | Ser<br>1300 | Phe | Arg | Gly | Thr | Asn<br>1305 | Ile | Glu | Asp | Leu |

| Cys | Leu<br>1310 | Glu | Phe | Val | Leu<br>1315 | Pro | Gly | Tyr | Thr | Asp<br>1320 | Tyr | Val | Leu | Ala |

| Leu | His<br>1325 | Ser | Ala | Asn | Asp<br>1330 | Met | Val | Asn | Leu | Asp<br>1335 | Asn | Leu | Glu | Glu |

| Tyr | Ile<br>1340 | Lys | Ala | Ile | Val<br>1345 | Asn | Ala | Thr | Ile | Cys<br>1350 | Asn | Gly | Ile | Gln |

| Lys | Gln<br>1355 | Val | Glu | Ala | Phe<br>1360 | Arg | Ser | Gly | Phe | Asn<br>1365 | Lys | Val | Phe | Pro |

| Ile | Glu<br>1370 | His | Leu | Gly | Ile<br>1375 | Phe | Asn | Glu | Glu | Glu<br>1380 | Leu | Glu | Thr | Leu |

| Leu | Cys<br>1385 | Gly | Glu | Arg | Asp<br>1390 | Leu | Phe | Asn | Met | Asn<br>1395 | Glu | Val | Leu | Asp |

| His | Ile<br>1400 | Lys | Phe | Asp | His<br>1405 | Gly | Tyr | Thr | Ser | Ser<br>1410 | Ser | Pro | Pro | Val |

| Glu | Asn<br>1415 | Leu | Leu | Glu | Ile<br>1420 | Leu | His | Glu | Phe | Asp<br>1425 | Lys | Asp | Gln | Gln |

| Arg | Ala<br>1430 | Phe | Leu | Gln | Phe<br>1435 | Val | Thr | Gly | Cys | Pro<br>1440 | Arg | Leu | Pro | Pro |

| Gly | Gly<br>1445 | Leu | Ala | Ser | Leu<br>1450 | Asn | Pro | Lys | Leu | Thr<br>1455 | Ile | Val | Arg | Lys |

| Arg | Gly<br>1460 | Ser | Asp | Ser | Ser<br>1465 | Glu | Thr | Asp | Leu | Pro<br>1470 | Ser | Val | Met | Thr |

| Cys | Ala<br>1475 | Asn | Tyr | Leu | Lys<br>1480 | Leu | Pro | Pro | Tyr | Ser<br>1485 | Ser | Lys | Glu | Lys |

| Met | Lys<br>1490 | Glu | Lys | Leu | Ile<br>1495 | Tyr | Ala | Ile | Thr | Glu<br>1500 | Gly | Gln | Gly | Ser |

| Phe | His<br>1505 | Leu | Ser | | | | | | | | | | | |

<210> SEQ ID NO 7
<211> LENGTH: 4446
<212> TYPE: DNA
<213> ORGANISM: Brassica rapa

<400> SEQUENCE: 7

```
atggagaaca gaggacagaa acgaatggag gttgtggggg agccacctgc tgataagaga    60
gcttgcaact cacaagactt cacatctggc gcctcctctg ctcaggctca acaagccaat   120
```

```
ggtaacactg atgctgacat ggacacttct tcctctgcct ctccttcgag tcgttcagat    180
ggagaacaag acagggagga ggaggaggag gaggaatccg actacggatc atgcgattcc    240
gatgatgagg atccgaggag gagggtgctt cagcggtatc agaggggag  atcaacagga    300 gatcagctga aactgaagtc tctcgcgtcg aggttgagtg aagaaaacga tccttctctg    360
cagttgactg gtcttacgga gctctgtgaa gtgttgtctt tctgtactga ggactctctg    420
tccattgtga tggctgactt gctctcgcgt gtgcttgtta agttggctaa gcatgagagc    480
aatgcagata tcatgctgct cgcaatcaga gcggttactt acttgtctga tgtttatccg    540
cggtcggtag cgttccttgt taaacatgag accattcctg ctctctgcca aagactactg    600
acgattgagt acttggatgt tgctgagcag tgtttgcaag cacttgagaa gatatccaga    660
gatcagccgg tagcatgctt gaacgctgga gcaattatgg cagtgctttc gtatatcgat    720
ttcttttcaa caagcataca gagagtcgca gtttctactg tggtgaatat atgtaggaag    780
cttccacctg agcctccctc gcctgtcatg gatgctgttc cagtattatg caatcttctt    840
caatatgaag accgacagtt ggtggagagt gtcgctattt gcttgacaaa aatagcagat    900
caagttagcc agtcgcctgc tatgttggat caactatgta gccatggact tatccatcaa    960
tcaacacatc ttttaaactt gaacagccgc acaaccctat ctcaacctgt ttacaacggc   1020
gtgattggat tgctaagaaa actatcttct ggttcaactt tagctttcag aacattgtat   1080
gagcttaaca ttggctacag actaaaagaa atcatatcca cctatgacat ttctcattca   1140
gtttcttcta cacagcccat ccatccatgc tccaaccagg tgcatgaagt cttgaagttg   1200
gtgattgagc ttcttccagc ttcacctgtt ggggataatc agctggcatt agaaaaggaa   1260
agttttcttg tcgatcagcc taatctcttg caacaatttg gagcagacat gcttcctgtt   1320
atgactcagg tgctaaagtc tggagctagc gtttatgttt cttatggttg cctatcagca   1380
attcacaagc tgacttgctt aagtaagtca gacgatcttg tcgagttact gaacaatgct   1440
aacatttcaa gtgttttggc gggcattttt tcaaggaaag atcatcatgt ggtcgttgtt   1500
gcactacaga ttgctgaagt gcttcttgag aaatacagag atgctttttt gaattccttt   1560
ataaaagagg gtgttttttt cgcaatcgca gcactcctaa cttctgatag gggacaacag   1620
atcaatccag tatccggttt cattcaagga tctgttccga aagagattgt gaaatgcttg   1680
tgccagtctt ttgaaggatc agtttcctct tcttcacaaa cttgcaaggt tggaaatgat   1740
tctgtctaca tcctcgcaac acgtatcaag gagagtttct ttggacctga ggtattcgac   1800
tctcagaaag gcttgacgga tgtcctccag aacctcaaga atctgtcggc agaactcaac   1860
gatttggtga ctgtacctgt cgatgcgcat gtcctgcatg gtgagaggtt cttctcaata   1920
tggaatcaaa tcatgcaag  gctgaaagag agggaatctg tgtccacttt tgaatttact   1980
gagagtggag ttgtgaaggc tctggcaaat tatctgtcta atggactcta cgaaaggaaa   2040
cttaacaaag gcgatcctga atgtgatagt ttaccacttg ttggtaacag atttgaagtg   2100
ttcacaagac tactttggtc tgatggcgag gcaactccgt ccgctttaat acagaagctc   2160
caaaattcct tatcttcttt agaaaactac ccaattgtcc tgagccagtt tttgaagcaa   2220
aggaactgtt tcgctgctat tccaaatgga cgttgcataa gttatccagt cctaagagtt   2280
cgttttgcta aagcagaggg ggagacttgt ctgcgtgatt actctccaaa ctttgtcacc   2340
gttgacccac tttgctactt ggacgctgtt agtcagtgcc tgtggcccca agtgaatttg   2400
gaacctttaa attctgtcga agcgaaagat caggctatag aatgtcaatc ttcacagctg   2460
cagtcaactt cgatatcttg tcaaggtgaa agctcaagcc atatggaaat tgactgtcct   2520
```

-continued

```
aatgcatctc agctgcaggg atctcaagag gaggaagacc aatatcacct tatagattca    2580
ggagaagaga attcttcctc atctaaagaa gaggatgtgc gacctcgact tttgtttcgt    2640
ctggaagggc ttgagctaga cccctctttg actgtttacc aggcaattct ctcgcacaaa    2700
ctaaaatcag aaaatgagac taccaacgat tcaaagctta gtggacacca caccatcact    2760
tacgaaagag ctccacagct tgcagtgtct catgaaaatc tgtttcccct cagatctatg    2820
gacaacgacg agcatcaccc gttttatcc tacttgtttg ctcatagact tggtttgcgc     2880
cacaaaggga caagtcctcc tgagtatgcc atattgtttc tgctcaagag tctggagggc    2940
atgaacagat ttctctttca gctgatttgt catgaaagga ttaatgcttt tggggaaggt    3000
aggctggaga gtttggatga tctaactgtg caggtgcgtc cggtgccata tgctgaattt    3060
gttagctcta agcttacaga gaagttagag cagcagctgc gtgattcttt tgctgtgtca    3120
ccgtgcggtc taccaccgtg gtttaatgat ctaatggctt catgcccgtt tctgtttagt    3180
tttgaagtca aatctaaata cttccgactt gcagcgttcg gtccacagca agtccataat    3240
cagccacagc accttggtag ttcaaatgtt catggtagtt acctcgtaa aaagttttta    3300 gcttgccgtg aaaagattct agagtctgct gcgaaaatga tggagttaca cggcacccag    3360
aaggtggccg ttgaggttgc gtacagtgaa gaagtcggaa ctggccttgg gccaacgctg    3420
gagttctaca cacttgtcag tagagcattt caaaatccgg atcttggtat gtggaggagt    3480
gatcctagct ccttggctgg aaagccaatg gtacctcctt caggactctt ccacgccct    3540 tggtcggcta catcagctgc ttttccaggt gtgctgcaga gtttgttct cttggggaca    3600 gtggtagcca aggctctaca agatggacga gtcttggaca ttcctttctc taaaaccttc    3660
tataaactaa ttctcggaca gggagttgag tcatttgaca tccatttcgt tgaccctgaa    3720 cttgtaaaa cactggtgga attgcaagct ctggcacgta ggagaaaggt tatctcagaa    3780
tcacaaagtg atgtccgagc agctaagtgt gacttgagtt ccgtggaac aaagattgag    3840 gacctttgtc ttgatttttc cctgcctggc tacacggact atgttctctc tcctcggttt    3900
gctaatgata tggtaaattt gggtaaccctc gaggagtatg taaaggctat tgtcaatgcc    3960
acagtatgta atgggatcaa aaaacaagtg gaagcgtttc ggtctggatt taacaaagtt    4020
ttccctattg aacatcttaa gatatttaat gaagaagaac tggaaacttt gttgtgtgga    4080
gaacgagatc tctttaatat gaatgaagtc ttggaccaca tcaagtttga tcatggttat    4140
acttctagca gcccaccagt tcaaaatttg ttggagattc tgcatgagtt tcacaaggag    4200
caacagcgag cttttctgca atttgtaaca ggatgtcctc ggctaccccc tggcggtttg    4260
gcgtctctca gtcccaaact taccattgtc cgcaagcacg gtagtgattc atcagaaaca    4320
gacctgccta gtgtgatgac ctgcgccaat tatctgaaac ttccaccttta ctcttccaaa    4380 gaaaagatga aggagaagct gatctatgcc ataactgaag ggcaaggttc cttccatctc    4440
tcttaa                                                              4446
```

<210> SEQ ID NO 8
<211> LENGTH: 1481
<212> TYPE: PRT
<213> ORGANISM: Brassica rapa

<400> SEQUENCE: 8

Met Glu Asn Arg Gly Gln Lys Arg Met Glu Val Val Gly Glu Pro Pro
1               5                   10                  15

Ala Asp Lys Arg Ala Cys Asn Ser Gln Asp Phe Thr Ser Gly Ala Ser

```
                   20                  25                  30
Ser Ala Gln Ala Gln Gln Ala Asn Gly Asn Thr Asp Ala Asp Met Asp
                35                  40                  45
Thr Ser Ser Ser Ala Ser Pro Ser Ser Arg Ser Asp Gly Glu Gln Asp
        50                  55                  60
Arg Glu Glu Glu Glu Glu Glu Ser Asp Tyr Gly Ser Cys Asp Ser
65                  70                  75                  80
Asp Asp Glu Asp Pro Arg Arg Val Leu Gln Arg Tyr Gln Arg Gly
                85                  90                  95
Arg Ser Thr Gly Asp Gln Leu Lys Leu Lys Ser Leu Ala Ser Arg Leu
                100                 105                 110
Ser Glu Glu Asn Asp Pro Ser Leu Gln Leu Thr Gly Leu Thr Glu Leu
                115                 120                 125
Cys Glu Val Leu Ser Phe Cys Thr Glu Asp Ser Leu Ser Ile Val Met
                130                 135                 140
Ala Asp Leu Leu Ser Arg Val Leu Val Lys Leu Ala Lys His Glu Ser
145                 150                 155                 160
Asn Ala Asp Ile Met Leu Leu Ala Ile Arg Ala Val Thr Tyr Leu Ser
                165                 170                 175
Asp Val Tyr Pro Arg Ser Val Ala Phe Leu Val Lys His Glu Thr Ile
                180                 185                 190
Pro Ala Leu Cys Gln Arg Leu Leu Thr Ile Glu Tyr Leu Asp Val Ala
                195                 200                 205
Glu Gln Cys Leu Gln Ala Leu Glu Lys Ile Ser Arg Asp Gln Pro Val
                210                 215                 220
Ala Cys Leu Asn Ala Gly Ala Ile Met Ala Val Leu Ser Tyr Ile Asp
225                 230                 235                 240
Phe Phe Ser Thr Ser Ile Gln Arg Val Ala Val Ser Thr Val Val Asn
                245                 250                 255
Ile Cys Arg Lys Leu Pro Pro Glu Pro Pro Ser Pro Val Met Asp Ala
                260                 265                 270
Val Pro Val Leu Cys Asn Leu Leu Gln Tyr Glu Asp Arg Gln Leu Val
                275                 280                 285
Glu Ser Val Ala Ile Cys Leu Thr Lys Ile Ala Asp Gln Val Ser Gln
                290                 295                 300
Ser Pro Ala Met Leu Asp Gln Leu Cys Ser His Gly Leu Ile His Gln
305                 310                 315                 320
Ser Thr His Leu Leu Asn Leu Asn Ser Arg Thr Thr Leu Ser Gln Pro
                325                 330                 335
Val Tyr Asn Gly Val Ile Gly Leu Leu Arg Lys Leu Ser Ser Gly Ser
                340                 345                 350
Thr Leu Ala Phe Arg Thr Leu Tyr Glu Leu Asn Ile Gly Tyr Arg Leu
                355                 360                 365
Lys Glu Ile Ile Ser Thr Tyr Asp Ile Ser His Ser Val Ser Ser Thr
                370                 375                 380
Gln Pro Ile His Pro Cys Ser Asn Gln Val His Glu Val Leu Lys Leu
385                 390                 395                 400
Val Ile Glu Leu Leu Pro Ala Ser Pro Val Gly Asp Asn Gln Leu Ala
                405                 410                 415
Leu Glu Lys Glu Ser Phe Leu Val Asp Gln Pro Asn Leu Leu Gln Gln
                420                 425                 430
Phe Gly Ala Asp Met Leu Pro Val Met Thr Gln Val Leu Lys Ser Gly
                435                 440                 445
```

```
Ala Ser Val Tyr Val Ser Tyr Gly Cys Leu Ser Ala Ile His Lys Leu
    450                 455                 460

Thr Cys Leu Ser Lys Ser Asp Asp Leu Val Glu Leu Leu Asn Asn Ala
465                 470                 475                 480

Asn Ile Ser Ser Val Leu Ala Gly Ile Phe Ser Arg Lys Asp His His
                485                 490                 495

Val Val Val Val Ala Leu Gln Ile Ala Glu Val Leu Leu Glu Lys Tyr
                500                 505                 510

Arg Asp Ala Phe Leu Asn Ser Phe Ile Lys Glu Gly Val Phe Phe Ala
                515                 520                 525

Ile Ala Ala Leu Leu Thr Ser Asp Arg Gly Gln Gln Ile Asn Pro Val
530                 535                 540

Ser Gly Phe Ile Gln Gly Ser Val Pro Lys Glu Ile Val Lys Cys Leu
545                 550                 555                 560

Cys Gln Ser Phe Glu Gly Ser Val Ser Ser Ser Gln Thr Cys Lys
                565                 570                 575

Val Gly Asn Asp Ser Val Tyr Ile Leu Ala Thr Arg Ile Lys Glu Ser
                580                 585                 590

Phe Phe Gly Pro Glu Val Phe Asp Ser Gln Lys Gly Leu Thr Asp Val
                595                 600                 605

Leu Gln Asn Leu Lys Asn Leu Ser Ala Glu Leu Asn Asp Leu Val Thr
        610                 615                 620

Val Pro Val Asp Ala His Val Leu His Gly Glu Arg Phe Phe Ser Ile
625                 630                 635                 640

Trp Asn Gln Ile Met Ala Arg Leu Lys Glu Arg Glu Ser Val Ser Thr
                645                 650                 655

Phe Glu Phe Thr Glu Ser Gly Val Val Lys Ala Leu Ala Asn Tyr Leu
                660                 665                 670

Ser Asn Gly Leu Tyr Glu Arg Lys Leu Asn Lys Gly Asp Pro Glu Cys
        675                 680                 685

Asp Ser Leu Pro Leu Val Gly Asn Arg Phe Glu Val Phe Thr Arg Leu
    690                 695                 700

Leu Trp Ser Asp Gly Glu Ala Thr Pro Ser Ala Leu Ile Gln Lys Leu
705                 710                 715                 720

Gln Asn Ser Leu Ser Ser Leu Glu Asn Tyr Pro Ile Val Leu Ser Gln
                725                 730                 735

Phe Leu Lys Gln Arg Asn Cys Phe Ala Ala Ile Pro Asn Gly Arg Cys
                740                 745                 750

Ile Ser Tyr Pro Val Leu Arg Val Arg Phe Ala Lys Ala Glu Gly Glu
        755                 760                 765

Thr Cys Leu Arg Asp Tyr Ser Pro Asn Phe Val Thr Val Asp Pro Leu
    770                 775                 780

Cys Tyr Leu Asp Ala Val Ser Gln Cys Leu Trp Pro Gln Val Asn Leu
785                 790                 795                 800

Glu Pro Leu Asn Ser Val Glu Ala Lys Asp Gln Ala Ile Glu Cys Gln
                805                 810                 815

Ser Ser Gln Leu Gln Ser Thr Ser Ile Ser Cys Gln Gly Glu Ser Ser
                820                 825                 830

Ser His Met Glu Ile Asp Cys Pro Asn Ala Ser Gln Leu Gln Gly Ser
        835                 840                 845

Gln Glu Glu Glu Asp Gln Tyr His Leu Ile Asp Ser Gly Glu Glu Asn
    850                 855                 860
```

-continued

Ser Ser Ser Ser Lys Glu Glu Asp Val Arg Pro Arg Leu Leu Phe Arg
865                 870                 875                 880

Leu Glu Gly Leu Glu Leu Asp Pro Ser Leu Thr Val Tyr Gln Ala Ile
            885                 890                 895

Leu Ser His Lys Leu Lys Ser Glu Asn Glu Thr Thr Asn Asp Ser Lys
            900                 905                 910

Leu Ser Gly His His Thr Ile Thr Tyr Glu Arg Ala Pro Gln Leu Ala
            915                 920                 925

Val Ser His Glu Asn Leu Phe Pro Leu Arg Ser Met Asp Asn Asp Glu
            930                 935                 940

His His Pro Phe Leu Ser Tyr Leu Phe Ala His Arg Leu Gly Leu Arg
945                 950                 955                 960

His Lys Gly Thr Ser Pro Pro Glu Tyr Ala Ile Leu Phe Leu Leu Lys
            965                 970                 975

Ser Leu Glu Gly Met Asn Arg Phe Leu Phe Gln Leu Ile Cys His Glu
            980                 985                 990

Arg Ile Asn Ala Phe Gly Glu Gly Arg Leu Glu Ser Leu Asp Asp Leu
            995                 1000                1005

Thr Val Gln Val Arg Pro Val Pro Tyr Ala Glu Phe Val Ser Ser
1010                1015                1020

Lys Leu Thr Glu Lys Leu Glu Gln Gln Leu Arg Asp Ser Phe Ala
1025                1030                1035

Val Ser Pro Cys Gly Leu Pro Pro Trp Phe Asn Asp Leu Met Ala
1040                1045                1050

Ser Cys Pro Phe Leu Phe Ser Phe Glu Val Lys Ser Lys Tyr Phe
1055                1060                1065

Arg Leu Ala Ala Phe Gly Pro Gln Gln Val His Asn Gln Pro Gln
1070                1075                1080

His Leu Gly Ser Ser Asn Val His Gly Ser Leu Pro Arg Lys Lys
1085                1090                1095

Phe Leu Ala Cys Arg Glu Lys Ile Leu Glu Ser Ala Ala Lys Met
1100                1105                1110

Met Glu Leu His Gly Thr Gln Lys Val Ala Val Glu Val Ala Tyr
1115                1120                1125

Ser Glu Glu Val Gly Thr Gly Leu Gly Pro Thr Leu Glu Phe Tyr
1130                1135                1140

Thr Leu Val Ser Arg Ala Phe Gln Asn Pro Asp Leu Gly Met Trp
1145                1150                1155

Arg Ser Asp Pro Ser Ser Leu Ala Gly Lys Pro Met Val Pro Pro
1160                1165                1170

Ser Gly Leu Phe Pro Arg Pro Trp Ser Ala Thr Ser Ala Ala Phe
1175                1180                1185

Pro Gly Val Leu Gln Lys Phe Val Leu Leu Gly Thr Val Val Ala
1190                1195                1200

Lys Ala Leu Gln Asp Gly Arg Val Leu Asp Ile Pro Phe Ser Lys
1205                1210                1215

Thr Phe Tyr Lys Leu Ile Leu Gly Gln Glu Leu Ser Ser Phe Asp
1220                1225                1230

Ile His Phe Val Asp Pro Glu Leu Cys Lys Thr Leu Val Glu Leu
1235                1240                1245

Gln Ala Leu Ala Arg Arg Arg Lys Val Ile Ser Glu Ser Gln Ser
1250                1255                1260

Asp Val Arg Ala Ala Lys Cys Asp Leu Ser Phe Arg Gly Thr Lys

```
                1265                1270                1275
Ile Glu Asp Leu Cys Leu Asp Phe Ser Leu Pro Gly Tyr Thr Asp
            1280                1285                1290

Tyr Val Leu Ser Pro Arg Phe Ala Asn Asp Met Val Asn Leu Gly
        1295                1300                1305

Asn Leu Glu Glu Tyr Val Lys Ala Ile Val Asn Ala Thr Val Cys
    1310                1315                1320

Asn Gly Ile Lys Lys Gln Val Glu Ala Phe Arg Ser Gly Phe Asn
1325                1330                1335

Lys Val Phe Pro Ile Glu His Leu Lys Ile Phe Asn Glu Glu Glu
    1340                1345                1350

Leu Glu Thr Leu Leu Cys Gly Glu Arg Asp Leu Phe Asn Met Asn
        1355                1360                1365

Glu Val Leu Asp His Ile Lys Phe Asp His Gly Tyr Thr Ser Ser
            1370                1375                1380

Ser Pro Pro Val Gln Asn Leu Leu Glu Ile Leu His Glu Phe His
        1385                1390                1395

Lys Glu Gln Gln Arg Ala Phe Leu Gln Phe Val Thr Gly Cys Pro
    1400                1405                1410

Arg Leu Pro Pro Gly Gly Leu Ala Ser Leu Ser Pro Lys Leu Thr
        1415                1420                1425

Ile Val Arg Lys His Gly Ser Asp Ser Ser Glu Thr Asp Leu Pro
            1430                1435                1440

Ser Val Met Thr Cys Ala Asn Tyr Leu Lys Leu Pro Pro Tyr Ser
        1445                1450                1455

Ser Lys Glu Lys Met Lys Glu Lys Leu Ile Tyr Ala Ile Thr Glu
    1460                1465                1470

Gly Gln Gly Ser Phe His Leu Ser
1475                1480
```

```
<210> SEQ ID NO 9
<211> LENGTH: 5553
<212> TYPE: DNA
<213> ORGANISM: Solanum lycopersicum

<400> SEQUENCE: 9
atggaaactc ggagccggaa acgaacggag gccacgtcat cagcgccttc tgcttcttct      60
ccttcatcag gtcccaccac acgcgctgtt aagaaagctc gttttaccac acgcgccgcc     120
tcaaactcga tctcaactcg ttcccgactc acaaatcgtt cccaagacct acaatcgatg     180
gactccacga atgaatcatc cgggtctggc agccgaacca ggcggggaaa gaatcacggg     240
ttagatagaa ataatccgga gaagggtaag gagaaagagc acgaaattag ggatagagac     300
agagatatgg gattgaacat ggatactgat ggggtgatg aagatgataa tgaaagtgaa      360
ggtggtgctg gattttgca acataatttg acttcagcaa gtagtgcact tcaaggactg      420
ttgagaaaat tgggtgctgg tttggatgat ttactgccga gttcagcaat ggtgtccgct     480
tcctcgtcgc aacagaatgg gcgtctgaag aagatattat cgggcttgag agctgacggg     540
gaagaaggga gcaaatagga ggcattgacg cagctttgtg tgatgctttc cattgggaca     600
gaagactctt tgagcacttt ttcagtggac tcttttgtac ctgtcctggt ggggctgctt     660
aatcatatga gtaatcctga tattatgctt ctcgcagcta gggcgttaac ccatttggtt     720
gatgttctgc catcttcttg tgctgctgtt gtgcattatg gagcggtttc atgttttgta     780
gctcgcttac tcacaattga atacatggac ttagctgagc agtctctaca agctttaaag     840
```

```
aagatatctc aagaagatcc aactgcttgt ttgcaagcag gtgcactcat ggctgtgctg    900
tcgtatctcg atttctttc cactggtgtt cagagagtag cactagcaac tgctgctaat    960
atgtgcaaga agctgccttc ggatgctgct gactttgtga tggaagctgt tccattgttg   1020
acgaatctcc ttcagtatca tgatgcaaag gtattagagc atgcttctat ctgcttgacc   1080
cggatagctg aagcatttgc atcatctcca gaaaagctag atgaactctg taatcacgga   1140
cttgtcacac aggctgcctc cctcatctca accagtaatt ctggaggtgg tcaggcttca   1200
ctcagcacgg aaacttacac aggcttgatc cggcttcttt gtacttgtgc cagtggctca   1260
ccattagggg ctaaaacctt gatgatgctt ggtatcagtg ggatcctcaa ggacatttta   1320
tcagcctctg tctctatttc acctgccatg agcagacctg cggagcagat ttttgagatt   1380
gtgaatcttg caaatgaact acttcctccg ctgcctcaag aattatctc tcttcctgtt    1440
agcacaaatt tgttcattag aggtcctttt acgcggaaat cctctgctag tggttctagc   1500
aaacaggagg atcttaatgc atcttctcag gaggtatcag ctcatgagaa actattgaat   1560
gatcaacctg aacttctgca acaatttgga atggatctcc ttcctgttct gatacagaca   1620
tatggatcca gtgtaaatac agcagcacgc cacaaatgcc tctcagttat ggaaaactt    1680
atgtatttca gtaatgcaga tatgattcaa tctttaacta atgacactaa cttgtcaagt   1740
ttcttggctg gggttttggc gtggaaggat ccccaagtat tggtcccgc tcttcaaata    1800
gcagagattc taatggagaa gctccctgga gttttggca agatgtttgt ccgggaaggt    1860
gttgttcatg ctgtagatgc cttgatgttg tctgggtctc atgtttctgc tcctcccat    1920
ccaacacgtg ctgagaaaga gaaacataat agacgccgta gcactaattc aatacagat    1980
gcaatttctg ttgaagatct tacaagtcca gttccaagta ctggatctct gccaaattca   2040
atggaaattc ggaccgttaa ttctagcctc cggatgtcag tcagtacatg tgcaaaagct   2100
ttcaaggata aatacttccc atcagattct gaggctgctg aagctggtgt cacgatgat    2160
cttatacgat tgaagaatct ctgcatgaag ttgaatgctg gtattgatga gcagatagct   2220
aaacctaaag gaaaatccaa acatttggt cctcagcttg gggatagcta tgttggaaaa    2280
gaagaaaact tggctgaagt gatagctgcc atgatggggg aactcagcaa aggggatggt   2340
gtttcaactt ttgagttcag tggaagtgga gttgttgctt cttttgctgaa atattttacg   2400
tttgcgtact tttctaagga aagaatctct gatactagta tgtctaagct tcgacaacaa   2460
gcaatcagaa gatacaagtc ttttattgca gttgcccttc ctgctggtgt tgatggtgga   2520
aatatggttc ccatgactgt tctggtccaa aagcttcaaa atgctctatg ttcattggag   2580
cgttttcctg ttgtattgag tcatagttcc agatcatcga caggaaatgc acgtctttct   2640
tcaggtttaa gtgttttgtc tcagccttt aagctgcgcc tttgcagagc tcaaggagag    2700
aaaaccctcc gtgactactc ttcaaatgtt ttgctgattg atccttgc aagtttagta     2760
gctattgaag aattcctttg ggcccgagtt gggagacctg aggctgaaca gaaggcatct   2820
gctactggtg gaaactctgg gtctgggact atacctgctg gaggcagtgc gtcatctcca   2880
tctatgtcca ctcctgcctc tgcatctcgt cgtcattctg ctcgatcaag gtcagcagtt   2940
aatattaatg aaagtgatgg aagctcttca aagggcaaag gtaaagcggt ttgaagcct    3000
gctcaaaaag atcgcagggg aattcgatca agagatcctg ttaaaataag agctgccttg   3060
gagaaggcct taagagagga gcctgttgat ggggagacta gttcagagga tgacgagctg   3120
catccttctc tcattgaact tgatgatgct ttggtgattg aggatgatat gttcgatgaa   3180
```

```
gatgaagatg accatgatga tgtgctgagg gatgatcctt ttcctgtctg catggcagat    3240
gaagtgcatg atgttaaatt gggagactct tcggaggata gcccttttgc acagacacca    3300
actggcagca atacaaatgc tggtggtggt tctgggagca gaattgcttc tgctcgggga    3360
tctgattccg ttgagttcag aagtaggaac tcgtatggtt caaggggggc aatgtcattt    3420
gctgctgctg ccatggctgg tctttcatct gctagtgtta gaggtgtgag ggcgctaga    3480
gatcgacatg ggcatcctct actcagctct ggtgatccac caaaactaat attttctgtt    3540
ggtgggaagc cgcttaatag gcagttgact atctaccagg ctatccagcg gcagcttgtt    3600
ctagacgagg atgatgatga gagatatggt ggcaatgatt ttgtatctgg tgacggcagt    3660
agggtttgga gtgatattta cacgatcaca taccagaggg cagacaacca agctgagagg    3720
tcaagtgggt ctgggagttc aatttccaag tctatgaaaa ccagttcttc aacaagttcc    3780
ggtgctgatc cttcattggt tcaagcatca ttgttagata gtatattgca gggagaactt    3840
ccttgtgatc tggagaaaag taaccctact tacagtattt tgtacctctt acgtgtattg    3900
gaggcgctga atcagcttgc cccccgtttg agagtcctgt ccatgattga tgatttctct    3960
gaaggaaaaa tttctagtct agatgagctc ggtactacgg gtatcaaaat cccttctgag    4020
gaatttgtca atagtaagct cactccgaaa ttggcacgac agatccagga tgctcttgca    4080
ctttgtagtg gatctcttcc atcttggtgt taccagttga ccaaggcctg cccatttctt    4140
tttccatttg agactcggcg ccagtacttc tattcaactg cttttgggtt gtcacgtgct    4200
ttatataggc tgcagcaaca gcaaggtgct gatggtaatg ggtctactca tgagagagca    4260
gttagggttg gcagattaca gcgccagaaa gttcgtgtct caaggaaccg cattctggat    4320
tctgctgcaa aagtaatgga gatgtactct agccaaaaag ctgttcttga agttgaatat    4380
tttggtgaag ttggtactgg cctgggtcct acacttgagt tttataccct tataagtcac    4440
gatctacaga aacttggact tggaatgtgg agatctggtt tatcattaac ttcaaatgaa    4500
cattctgtgg aagttcatat cgataataaa ttaagtagaa gtgacggaga tcttgtccaa    4560
gcacctcttg gattattccc acgtccctgg tcaccacata ctggtactgt tgatggaggt    4620
caattctata aagcaattga atatttccgc ttgcttggac gtgttatggc gaaagctctt    4680
caagatggac ggcttttgga ccttccactg tccatggcct tctataagct cgttcttggt    4740
caagaacttg atttgtatga tattctttct tttgacaccg aattggggaa gactttgcaa    4800
gagttgcaag ccctcgtcag tcgaaagcaa tatatagaat caataaaaga tcagaacctg    4860
gacgagtctt atgacatgca ttttcgtggg actccagttg aggatctttg tttagatttc    4920
acacttcctg gctatcctga atatattctt aaagcaggcg acgagaatgt gagtcgcgat    4980
atcgtggatt taacttgga ggagtatatt tctttggtag ttgatgctac tgtgaaaact    5040
ggaatcaggc agcaaatgga ggcttttaga tctggcttca atcaggtttt cgacttttca    5100
gctctgcaaa tattctctcc ttcagagtta gactatctat tatgtggccg tagagagctg    5160
tggaagcctg agacgctagt agatcacata aaattcgatc atggattcac atccaagagt    5220
cctcctatta ttcatttact agagattatg ggagagttca cacctgagca gcaacgagca    5280
ttctgccagt tgttactgg tgctcctcgg ctccccgcag gtggtcttgc ttctctgaat    5340
cctaagttga caattgtgag gaagcattca tctagtgctg gcaatgcagc acagaacagt    5400
aatgccccat cagaatctgc agatgaagac ctacccagtg tgatgacatg tgctaattac    5460
ttgaaactcc ctcctattc tactaaggag atcatgtcca agaaattact ctatgccatt    5520
aatgaaggtc aaggatcgtt tgatttgtca taa                                 5553
```

<210> SEQ ID NO 10
<211> LENGTH: 1850
<212> TYPE: PRT
<213> ORGANISM: Solanum lycopersicum

<400> SEQUENCE: 10

```
Met Glu Thr Arg Ser Arg Lys Arg Thr Glu Ala Thr Ser Ser Ala Pro
1               5                   10                  15

Ser Ala Ser Ser Pro Ser Ser Gly Pro Thr Thr Arg Ala Val Lys Lys
                20                  25                  30

Ala Arg Phe Thr Thr Arg Ala Ala Ser Asn Ser Ile Ser Thr Arg Ser
            35                  40                  45

Arg Leu Thr Asn Arg Ser Gln Asp Leu Gln Ser Met Asp Ser Thr Asn
        50                  55                  60

Glu Ser Ser Gly Ser Gly Ser Arg Thr Arg Arg Gly Lys Asn His Gly
65                  70                  75                  80

Leu Asp Arg Asn Asn Pro Glu Lys Gly Lys Glu Lys Glu His Glu Ile
                85                  90                  95

Arg Asp Arg Asp Arg Asp Met Gly Leu Asn Met Asp Thr Asp Gly Gly
            100                 105                 110

Asp Glu Asp Asp Asn Glu Ser Glu Gly Gly Ala Gly Ile Leu Gln His
        115                 120                 125

Asn Leu Thr Ser Ala Ser Ser Ala Leu Gln Gly Leu Leu Arg Lys Leu
    130                 135                 140

Gly Ala Gly Leu Asp Asp Leu Leu Pro Ser Ser Ala Met Val Ser Ala
145                 150                 155                 160

Ser Ser Ser Gln Gln Asn Gly Arg Leu Lys Lys Ile Leu Ser Gly Leu
                165                 170                 175

Arg Ala Asp Gly Glu Glu Gly Lys Gln Ile Glu Ala Leu Thr Gln Leu
            180                 185                 190

Cys Val Met Leu Ser Ile Gly Thr Glu Asp Ser Leu Ser Thr Phe Ser
        195                 200                 205

Val Asp Ser Phe Val Pro Val Leu Val Gly Leu Leu Asn His Met Ser
    210                 215                 220

Asn Pro Asp Ile Met Leu Leu Ala Ala Arg Ala Leu Thr His Leu Val
225                 230                 235                 240

Asp Val Leu Pro Ser Ser Cys Ala Ala Val Val His Tyr Gly Ala Val
                245                 250                 255

Ser Cys Phe Val Ala Arg Leu Leu Thr Ile Glu Tyr Met Asp Leu Ala
            260                 265                 270

Glu Gln Ser Leu Gln Ala Leu Lys Lys Ile Ser Gln Glu Asp Pro Thr
        275                 280                 285

Ala Cys Leu Gln Ala Gly Ala Leu Met Ala Val Leu Ser Tyr Leu Asp
    290                 295                 300

Phe Phe Ser Thr Gly Val Gln Arg Val Ala Leu Ala Thr Ala Ala Asn
305                 310                 315                 320

Met Cys Lys Lys Leu Pro Ser Asp Ala Ala Asp Phe Val Met Glu Ala
                325                 330                 335

Val Pro Leu Leu Thr Asn Leu Leu Gln Tyr His Asp Ala Lys Val Leu
            340                 345                 350

Glu His Ala Ser Ile Cys Leu Thr Arg Ile Ala Glu Ala Phe Ala Ser
        355                 360                 365

Ser Pro Glu Lys Leu Asp Glu Leu Cys Asn His Gly Leu Val Thr Gln
```

-continued

```
              370                 375                 380
Ala Ala Ser Leu Ile Ser Thr Ser Asn Ser Gly Gly Gln Ala Ser
385                 390                 395                 400

Leu Ser Thr Glu Thr Tyr Thr Gly Leu Ile Arg Leu Leu Cys Thr Cys
                405                 410                 415

Ala Ser Gly Ser Pro Leu Gly Ala Lys Thr Leu Met Met Leu Gly Ile
                420                 425                 430

Ser Gly Ile Leu Lys Asp Ile Leu Ser Ala Ser Val Ser Ile Ser Pro
                435                 440                 445

Ala Met Ser Arg Pro Ala Glu Gln Ile Phe Glu Ile Val Asn Leu Ala
450                 455                 460

Asn Glu Leu Leu Pro Pro Leu Pro Gln Gly Ile Ile Ser Leu Pro Val
465                 470                 475                 480

Ser Thr Asn Leu Phe Ile Arg Gly Pro Phe Thr Arg Lys Ser Ser Ala
                485                 490                 495

Ser Gly Ser Ser Lys Gln Glu Asp Leu Asn Ala Ser Ser Gln Glu Val
                500                 505                 510

Ser Ala His Glu Lys Leu Leu Asn Asp Gln Pro Glu Leu Leu Gln Gln
                515                 520                 525

Phe Gly Met Asp Leu Leu Pro Val Leu Ile Gln Thr Tyr Gly Ser Ser
        530                 535                 540

Val Asn Thr Ala Ala Arg His Lys Cys Leu Ser Val Ile Gly Lys Leu
545                 550                 555                 560

Met Tyr Phe Ser Asn Ala Asp Met Ile Gln Ser Leu Thr Asn Asp Thr
                565                 570                 575

Asn Leu Ser Ser Phe Leu Ala Gly Val Leu Ala Trp Lys Asp Pro Gln
                580                 585                 590

Val Leu Val Pro Ala Leu Gln Ile Ala Glu Ile Leu Met Glu Lys Leu
                595                 600                 605

Pro Gly Val Phe Gly Lys Met Phe Val Arg Glu Gly Val Val His Ala
        610                 615                 620

Val Asp Ala Leu Met Leu Ser Gly Ser His Val Ser Ala Pro Pro His
625                 630                 635                 640

Pro Thr Arg Ala Glu Lys Glu Lys His Asn Arg Arg Ser Thr Asn
                645                 650                 655

Ser Asn Thr Asp Ala Ile Ser Val Glu Asp Leu Thr Ser Pro Val Pro
                660                 665                 670

Ser Thr Gly Ser Leu Pro Asn Ser Met Glu Ile Arg Thr Val Asn Ser
                675                 680                 685

Ser Leu Arg Met Ser Val Ser Thr Cys Ala Lys Ala Phe Lys Asp Lys
        690                 695                 700

Tyr Phe Pro Ser Asp Ser Glu Ala Ala Glu Gly Val Thr Asp Asp
705                 710                 715                 720

Leu Ile Arg Leu Lys Asn Leu Cys Met Lys Leu Asn Ala Gly Ile Asp
                725                 730                 735

Glu Gln Ile Ala Lys Pro Lys Gly Lys Ser Lys Thr Phe Gly Pro Gln
                740                 745                 750

Leu Gly Asp Ser Tyr Val Gly Lys Glu Asn Leu Ala Glu Val Ile
                755                 760                 765

Ala Ala Met Met Gly Glu Leu Ser Lys Gly Asp Gly Val Ser Thr Phe
        770                 775                 780

Glu Phe Ser Gly Ser Gly Val Val Ala Ser Leu Leu Lys Tyr Phe Thr
785                 790                 795                 800
```

-continued

Phe Ala Tyr Phe Ser Lys Glu Arg Ile Ser Asp Thr Ser Met Ser Lys
            805                 810                 815

Leu Arg Gln Gln Ala Ile Arg Arg Tyr Lys Ser Phe Ile Ala Val Ala
            820                 825                 830

Leu Pro Ala Gly Val Asp Gly Gly Asn Met Val Pro Met Thr Val Leu
            835                 840                 845

Val Gln Lys Leu Gln Asn Ala Leu Cys Ser Leu Glu Arg Phe Pro Val
            850                 855                 860

Val Leu Ser His Ser Ser Arg Ser Ser Thr Gly Asn Ala Arg Leu Ser
865                 870                 875                 880

Ser Gly Leu Ser Val Leu Ser Gln Pro Phe Lys Leu Arg Leu Cys Arg
            885                 890                 895

Ala Gln Gly Glu Lys Thr Leu Arg Asp Tyr Ser Ser Asn Val Leu Leu
            900                 905                 910

Ile Asp Pro Leu Ala Ser Leu Val Ala Ile Glu Glu Phe Leu Trp Ala
            915                 920                 925

Arg Val Gly Arg Pro Glu Ala Glu Gln Lys Ala Ser Ala Thr Gly Gly
            930                 935                 940

Asn Ser Gly Ser Gly Thr Ile Pro Ala Gly Gly Ser Ala Ser Ser Pro
945                 950                 955                 960

Ser Met Ser Thr Pro Ala Ser Ala Ser Arg Arg His Ser Ala Arg Ser
            965                 970                 975

Arg Ser Ala Val Asn Ile Asn Glu Ser Asp Gly Ser Ser Ser Lys Gly
            980                 985                 990

Lys Gly Lys Ala Val Leu Lys Pro Ala Gln Lys Asp Arg Arg Gly Ile
            995                 1000                1005

Arg Ser Arg Asp Pro Val Lys Ile Arg Ala Ala Leu Glu Lys Ala
            1010                1015                1020

Leu Arg Glu Glu Pro Val Asp Gly Glu Thr Ser Ser Glu Asp Asp
            1025                1030                1035

Glu Leu His Pro Ser Leu Ile Glu Leu Asp Asp Ala Leu Val Ile
            1040                1045                1050

Glu Asp Asp Met Phe Asp Glu Asp Glu Asp His Asp Asp Val
            1055                1060                1065

Leu Arg Asp Asp Pro Phe Pro Val Cys Met Ala Asp Glu Val His
            1070                1075                1080

Asp Val Lys Leu Gly Asp Ser Ser Glu Asp Ser Pro Phe Ala Gln
            1085                1090                1095

Thr Pro Thr Gly Ser Asn Thr Asn Ala Gly Gly Gly Ser Gly Ser
            1100                1105                1110

Arg Ile Ala Ser Ala Arg Gly Ser Asp Ser Val Glu Phe Arg Ser
            1115                1120                1125

Arg Asn Ser Tyr Gly Ser Arg Gly Ala Met Ser Phe Ala Ala Ala
            1130                1135                1140

Ala Met Ala Gly Leu Ser Ser Ala Ser Val Arg Gly Val Arg Gly
            1145                1150                1155

Ala Arg Asp Arg His Gly His Pro Leu Leu Ser Ser Gly Asp Pro
            1160                1165                1170

Pro Lys Leu Ile Phe Ser Val Gly Gly Lys Pro Leu Asn Arg Gln
            1175                1180                1185

Leu Thr Ile Tyr Gln Ala Ile Gln Arg Gln Leu Val Leu Asp Glu
            1190                1195                1200

-continued

```
Asp Asp Asp Glu Arg Tyr Gly Gly Asn Asp Phe Val Ser Gly Asp
    1205                1210                1215

Gly Ser Arg Val Trp Ser Asp Ile Tyr Thr Ile Thr Tyr Gln Arg
    1220                1225                1230

Ala Asp Asn Gln Ala Glu Arg Ser Ser Gly Ser Gly Ser Ser Ile
    1235                1240                1245

Ser Lys Ser Met Lys Thr Ser Ser Ser Thr Ser Ser Gly Ala Asp
    1250                1255                1260

Pro Ser Leu Val Gln Ala Ser Leu Leu Asp Ser Ile Leu Gln Gly
    1265                1270                1275

Glu Leu Pro Cys Asp Leu Glu Lys Ser Asn Pro Thr Tyr Ser Ile
    1280                1285                1290

Leu Tyr Leu Leu Arg Val Leu Glu Ala Leu Asn Gln Leu Ala Pro
    1295                1300                1305

Arg Leu Arg Val Leu Ser Met Ile Asp Asp Phe Ser Glu Gly Lys
    1310                1315                1320

Ile Ser Ser Leu Asp Glu Leu Gly Thr Thr Gly Ile Lys Ile Pro
    1325                1330                1335

Ser Glu Glu Phe Val Asn Ser Lys Leu Thr Pro Lys Leu Ala Arg
    1340                1345                1350

Gln Ile Gln Asp Ala Leu Ala Leu Cys Ser Gly Ser Leu Pro Ser
    1355                1360                1365

Trp Cys Tyr Gln Leu Thr Lys Ala Cys Pro Phe Leu Phe Pro Phe
    1370                1375                1380

Glu Thr Arg Arg Gln Tyr Phe Tyr Ser Thr Ala Phe Gly Leu Ser
    1385                1390                1395

Arg Ala Leu Tyr Arg Leu Gln Gln Gln Gly Ala Asp Gly Asn
    1400                1405                1410

Gly Ser Thr His Glu Arg Ala Val Arg Val Gly Arg Leu Gln Arg
    1415                1420                1425

Gln Lys Val Arg Val Ser Arg Asn Arg Ile Leu Asp Ser Ala Ala
    1430                1435                1440

Lys Val Met Glu Met Tyr Ser Ser Gln Lys Ala Val Leu Glu Val
    1445                1450                1455

Glu Tyr Phe Gly Glu Val Gly Thr Gly Leu Gly Pro Thr Leu Glu
    1460                1465                1470

Phe Tyr Thr Leu Ile Ser His Asp Leu Gln Lys Leu Gly Leu Gly
    1475                1480                1485

Met Trp Arg Ser Gly Leu Ser Leu Thr Ser Asn Glu His Ser Val
    1490                1495                1500

Glu Val His Ile Asp Asn Lys Leu Ser Arg Ser Asp Gly Asp Leu
    1505                1510                1515

Val Gln Ala Pro Leu Gly Leu Phe Pro Arg Pro Trp Ser Pro His
    1520                1525                1530

Thr Gly Thr Val Asp Gly Gly Gln Phe Tyr Lys Ala Ile Glu Tyr
    1535                1540                1545

Phe Arg Leu Leu Gly Arg Val Met Ala Lys Ala Leu Gln Asp Gly
    1550                1555                1560

Arg Leu Leu Asp Leu Pro Leu Ser Met Ala Phe Tyr Lys Leu Val
    1565                1570                1575

Leu Gly Gln Glu Leu Asp Leu Tyr Asp Ile Leu Ser Phe Asp Thr
    1580                1585                1590

Glu Leu Gly Lys Thr Leu Gln Glu Leu Gln Ala Leu Val Ser Arg
```

| | | | | | | | | | |
|---|---|---|---|---|---|---|---|---|---|
| | | 1595 | | | 1600 | | | 1605 | |
| Lys | Gln | Tyr | Ile | Glu | Ser | Ile | Lys | Asp | Gln | Asn | Leu | Asp | Glu | Ser |

Lys Gln Tyr Ile Glu Ser Ile Lys Asp Gln Asn Leu Asp Glu Ser
1610                1615                1620

Tyr Asp Met His Phe Arg Gly Thr Pro Val Glu Asp Leu Cys Leu
1625                1630                1635

Asp Phe Thr Leu Pro Gly Tyr Pro Glu Tyr Ile Leu Lys Ala Gly
1640                1645                1650

Asp Glu Asn Val Ser Arg Asp Ile Val Asp Phe Asn Leu Glu Glu
1655                1660                1665

Tyr Ile Ser Leu Val Val Asp Ala Thr Val Lys Thr Gly Ile Arg
1670                1675                1680

Gln Gln Met Glu Ala Phe Arg Ser Gly Phe Asn Gln Val Phe Asp
1685                1690                1695

Phe Ser Ala Leu Gln Ile Phe Ser Pro Ser Glu Leu Asp Tyr Leu
1700                1705                1710

Leu Cys Gly Arg Arg Glu Leu Trp Lys Pro Glu Thr Leu Val Asp
1715                1720                1725

His Ile Lys Phe Asp His Gly Phe Thr Ser Lys Ser Pro Pro Ile
1730                1735                1740

Ile His Leu Leu Glu Ile Met Gly Glu Phe Thr Pro Glu Gln Gln
1745                1750                1755

Arg Ala Phe Cys Gln Phe Val Thr Gly Ala Pro Arg Leu Pro Ala
1760                1765                1770

Gly Gly Leu Ala Ser Leu Asn Pro Lys Leu Thr Ile Val Arg Lys
1775                1780                1785

His Ser Ser Ser Ala Gly Asn Ala Ala Gln Asn Ser Asn Ala Pro
1790                1795                1800

Ser Glu Ser Ala Asp Glu Asp Leu Pro Ser Val Met Thr Cys Ala
1805                1810                1815

Asn Tyr Leu Lys Leu Pro Pro Tyr Ser Thr Lys Glu Ile Met Ser
1820                1825                1830

Lys Lys Leu Leu Tyr Ala Ile Asn Glu Gly Gln Gly Ser Phe Asp
1835                1840                1845

Leu Ser
1850

```
<210> SEQ ID NO 11
<211> LENGTH: 3612
<212> TYPE: DNA
<213> ORGANISM: Oryza sativa

<400> SEQUENCE: 11
atggagtgcc caaggagtg cctcagccac ggcgtgccag ccgccgtgct gcagttcttc      60
gacttcttct cgatgcacaa gcagaagctg gtgctcaaga tcgtcgccaa cgtcttgggc     120
gacttcagcg cgaaggatgc ggccaaggcc atggaggccg cgcccgttct gtgcaacctc     180
ctgcaatcca ctgacaagac gatactcgac tccgccgttt cttgcttggt tttggtctct     240
gatggtgctt gcgacagtgc ccaacacatg gaaaagcttt acgagcttaa tgcagtccaa     300
gcgacgatga ggttgatgga gaacgacggg tggaagagcc tcagcgatga acttttatct     360
ggcatccttg gtcttctcaa agacctagct tctctctcag caagggctgt aaagtctctt     420
tttgagttaa acatttgtga tttgctcaag cagatgataa catactacac ctcgtcgcac     480
agtgatcaca ataaggtgca gacgcttgta gagctcattt attatcttat gccacctctt     540
```

```
gaaatgtgtg accatcgtac cgaactaatc attgcaaaga agaatgtcat cacagaacaa      600
agtggataca tccaacagct tgctagcatc cttacttta taatacaggt tgcgaaatct       660
gctgcactat catcaatttg ctacagttgt gttgttgtca tcagaaacat tgttgaatta     720
agcacacctt cttccttggt ggaggtacag aagacagtaa acctgtcaag cttacttgct     780
ggctggttgg cccggaagaa ccgccatatc atattccaaa cgctcaacgt ttcgaagacc     840
cttctgagaa aagaccagaa attcttcttt gagaccttca tcaggaggg tctaaagcat      900 gcaattgatg caatactaac acaggaaaaa ggaaagagcc gcttgccaga agttgcctt      960 tgttttgatt tagacttgga gacctcgaca atgatgcat gcaggattaa taatggtgct      1020
atcctgaaac tagcggagga gataaagaaa aacttcttgg taaaggttgc caagtctcct    1080
cacaagtttg ggtgtgcttt taaaagcata aaggaatttt tttctcgttt gaattgtcat    1140
gccacggcac ccccagctaa agatcaggat ctctgcaagc agttgtctga ttttcaagg     1200 caattattat cggatgaact gccaagtact tctacttttg agtttgtgca gagtggatct    1260
atcaaacatt tggcaggtta tctttccaat gggacatact ttaattcaaa tctcaggaat    1320
tgccaggact tgataggga gcttaaggag gtgaaaatcc ggctgcagaa gttcacgcac     1380
ttggctctca gcgtggacaa tgaaagctcg gtgaagccac ttgagatttt ggtggagaaa    1440
ctgatagatg cgttgcatgt gtggtatgac agtttccctg taatcctggc tgatgaacag    1500
tgcacacgtg agagcaccat gattcctctg agggattcag gaactgagga accaatgtca    1560
ctatatataa aattttcgag atcagccagg gaggaggagt tggaggatta tggtggagtt    1620
ctccctgttg atctttcttc gacacctgaa tccattgaag aggtcctgtt gcctgagatc    1680
tgtaaaagaa ctggcaatga aacttcatac aaggaaaaca ctcaagaagc aaatgggagc    1740
agaaaatctg ttgggctcag aaatggtgac gggcacaagt tctcaagatt gaaattctct    1800
tacaaaggaa cacaactcca gtcatctaca ccacttttg agtcaatcct ccgctcaatg     1860
catgaaggag aaaccgatct ccagattgac ccatcttttt gggataaaga acacaagata    1920
gtatacagaa gaagaaacaa aagcaagaaa atatcttccc atagttccta caatattcag    1980
ttgtgccgtg tgcatgaaaa acttgaaatg tcattgctta aggacccctt tttctccacc    2040
atactcactg gcaagcttcc tggtgatctg gatgaatctg atccatcata taacttcctg    2100
ttcatgctga aagtcctcga agggctcaac cgttttttcat atcatctatc aatggatgat    2160
aagttatgca aatttgctga aggctgcctc caagagtttg atgaccttaa ggtggcaatt    2220
tgtccaattc cacgggatca gttcgtgagc agtctactga caaataagtt agagcagcaa    2280
atgcaagata gcttgtttgg ggatggcttg ataccctcgt ggtgtatcta tttggttgaa    2340
acttgcccgt tcttgttgtc attcgaagct cgatggaagt atttctgcct gacggcacat    2400
cactcattca tgacagatga ggctagcagt tcaacagaaa ctaagaagta cagcgtaaca    2460
cggagcaaaa tccttgaaga tgcttcatcg atgttgaaca acatggatc agacaccaaa     2520 ttcattgagg tggaattga tggagaggtt gggaccggtc gaggcccaac cttcgaattc     2580
tataccacag ttagtcatga actacagaga gtgggtcttg gaatgtggag aggagacgac    2640
accagccaag aatgcgaagc tggttttgtc catgcccctt ttggtctctt tccacagcca    2700
tggtcctcag caaacacttc atctcaaggg atcagtttgt ccaatgtggt acaaaaattc    2760
aagcttcttg ggcatcttgt agcaagagca gttttggatg aagggttct ggatattcct     2820 ctctcgaaag cattttacaa gatcatgctt gagcaggacc ttgatattta tgacattcca    2880
tcatttgatc ccaagttggg caagactgtt atggagtttc aagcacttgt taaaaggaag    2940
```

-continued

```
aagttcctgg aggaaagggc atccaatcca gcagctgatt tgtcctataa aaacgtgcga    3000
ttggaggatt tatgtcttga ctttacccct cctggaaatc cggaatatga acttgtccct    3060
ggaggttcag agaagatggt gacacttgac aatttggagg agtatgtgtc ttcaattgtt    3120
gatgcaacct tgaaaagtgg gatatccaat caaatagaag ctttcaaggc tggaattaac    3180 aaggttttg ctcttaagac tcttcggttg ttcagtgagg atgagatgga gcgtatacta    3240
tgtggcgaac aagattcttg ggcttcgaac aaacttgagg atcacatcaa ttttgattat    3300
ggatatgatg cgaacagtgc atcagtaatt agtttcctgg atcttgcg ggagtttgga    3360 agagaggacc agcgggcgtt cttgcatttt acgactggag ctcctcagct cccacttggt    3420
ggcctagctt cgctcgatcc taagctcacc gtagtgcgaa agcaatgtga tggcaaagta    3480
gacaacgaat taccgagtgt caatacttgc cggcatttct tcaagcttcc accgtactcc    3540
tctaaggaga ttatgagaca gaagctcaaa tatgctatca aggagggttt aggctccttc    3600
caattatcat ga                                                        3612
```

<210> SEQ ID NO 12
<211> LENGTH: 1203
<212> TYPE: PRT
<213> ORGANISM: Oryza sativa

<400> SEQUENCE: 12

```
Met Glu Cys Pro Lys Glu Cys Leu Ser His Gly Val Pro Ala Ala Val
1               5                   10                  15

Leu Gln Phe Phe Asp Phe Phe Ser Met His Lys Gln Lys Leu Val Leu
            20                  25                  30

Lys Ile Val Ala Asn Val Leu Gly Asp Phe Ser Ala Lys Asp Ala Ala
        35                  40                  45

Lys Ala Met Glu Ala Ala Pro Val Leu Cys Asn Leu Leu Gln Ser Thr
    50                  55                  60

Asp Lys Thr Ile Leu Asp Ser Ala Val Ser Cys Leu Val Leu Val Ser
65                  70                  75                  80

Asp Gly Ala Cys Asp Ser Ala Gln His Met Glu Lys Leu Tyr Glu Leu
                85                  90                  95

Asn Ala Val Gln Ala Thr Met Arg Leu Met Glu Asn Asp Gly Trp Lys
            100                 105                 110

Ser Leu Ser Asp Glu Thr Leu Ser Gly Ile Leu Gly Leu Leu Lys Asp
        115                 120                 125

Leu Ala Ser Leu Ser Ala Arg Ala Val Lys Ser Leu Phe Glu Leu Asn
    130                 135                 140

Ile Cys Asp Leu Leu Lys Gln Met Ile Thr Tyr Tyr Thr Ser Ser His
145                 150                 155                 160

Ser Asp His Asn Lys Val Gln Thr Leu Val Glu Leu Ile Tyr Tyr Leu
                165                 170                 175

Met Pro Pro Leu Glu Met Cys Asp His Arg Thr Glu Leu Ile Ile Ala
            180                 185                 190

Lys Lys Asn Val Ile Thr Glu Gln Ser Gly Tyr Ile Gln Gln Leu Ala
        195                 200                 205

Ser Ile Leu Thr Phe Ile Ile Gln Val Ala Lys Ser Ala Ala Leu Ser
    210                 215                 220

Ser Ile Cys Tyr Ser Cys Val Val Ile Arg Asn Ile Val Glu Leu
225                 230                 235                 240

Ser Thr Pro Ser Ser Leu Val Glu Val Gln Lys Thr Val Asn Leu Ser
```

```
                245                 250                 255
Ser Leu Leu Ala Gly Trp Leu Ala Arg Lys Asn Arg His Ile Ile Phe
            260                 265                 270
Gln Thr Leu Asn Val Ser Lys Thr Leu Leu Arg Lys Asp Gln Lys Phe
        275                 280                 285
Phe Phe Glu Thr Phe Ile Arg Glu Gly Leu Lys His Ala Ile Asp Ala
    290                 295                 300
Ile Leu Thr Gln Glu Lys Gly Lys Ser Arg Leu Pro Glu Ser Cys Leu
305                 310                 315                 320
Cys Phe Asp Leu Asp Leu Glu Thr Ser Thr Asp Asp Ala Cys Arg Ile
                325                 330                 335
Asn Asn Gly Ala Ile Leu Lys Leu Ala Glu Glu Ile Lys Lys Asn Phe
            340                 345                 350
Leu Val Lys Val Ala Lys Ser Pro His Lys Phe Gly Cys Ala Phe Lys
        355                 360                 365
Ser Ile Lys Glu Phe Phe Ser Arg Leu Asn Cys His Ala Thr Ala Pro
    370                 375                 380
Pro Ala Lys Asp Gln Asp Leu Cys Lys Gln Leu Ser Asp Phe Ser Arg
385                 390                 395                 400
Gln Leu Leu Ser Asp Glu Leu Pro Ser Thr Ser Phe Glu Phe Val
                405                 410                 415
Gln Ser Gly Ser Ile Lys His Leu Ala Gly Tyr Leu Ser Asn Gly Thr
            420                 425                 430
Tyr Phe Asn Ser Asn Leu Arg Asn Cys Gln Asp Leu Ile Gly Glu Leu
        435                 440                 445
Lys Glu Val Lys Ile Arg Leu Gln Lys Phe Thr His Leu Ala Leu Ser
    450                 455                 460
Val Asp Asn Glu Ser Ser Val Lys Pro Leu Ile Leu Val Glu Lys
465                 470                 475                 480
Leu Ile Asp Ala Leu His Val Trp Tyr Asp Ser Phe Pro Val Ile Leu
                485                 490                 495
Ala Asp Glu Gln Cys Thr Arg Glu Ser Thr Met Ile Pro Leu Arg Asp
            500                 505                 510
Ser Gly Thr Glu Glu Pro Met Ser Leu Tyr Ile Lys Phe Ser Arg Ser
        515                 520                 525
Ala Arg Glu Glu Glu Leu Glu Asp Tyr Gly Gly Val Leu Pro Val Asp
    530                 535                 540
Leu Ser Ser Thr Pro Glu Ser Ile Glu Glu Val Leu Leu Pro Glu Ile
545                 550                 555                 560
Cys Lys Arg Thr Gly Asn Glu Thr Ser Tyr Lys Glu Asn Thr Gln Glu
                565                 570                 575
Ala Asn Gly Ser Arg Lys Ser Val Gly Leu Arg Asn Gly Asp Gly His
            580                 585                 590
Lys Phe Ser Arg Leu Lys Phe Ser Tyr Lys Gly Thr Gln Leu Gln Ser
        595                 600                 605
Ser Thr Pro Leu Phe Glu Ser Ile Leu Arg Ser Met His Glu Gly Glu
    610                 615                 620
Thr Asp Leu Gln Ile Asp Pro Ser Phe Trp Asp Lys Glu His Lys Ile
625                 630                 635                 640
Val Tyr Arg Arg Arg Asn Lys Ser Lys Lys Ile Ser Ser His Ser Ser
                645                 650                 655
Tyr Asn Ile Gln Leu Cys Arg Val His Glu Lys Leu Glu Met Ser Leu
            660                 665                 670
```

```
Leu Lys Asp Pro Phe Phe Ser Thr Ile Leu Thr Gly Lys Leu Pro Gly
        675                 680                 685

Asp Leu Asp Glu Ser Asp Pro Ser Tyr Asn Phe Leu Phe Met Leu Lys
690                 695                 700

Val Leu Glu Gly Leu Asn Arg Phe Ser Tyr His Leu Ser Met Asp Asp
705                 710                 715                 720

Lys Leu Cys Lys Phe Ala Glu Gly Cys Leu Gln Glu Phe Asp Asp Leu
                725                 730                 735

Lys Val Ala Ile Cys Pro Ile Pro Arg Asp Gln Phe Val Ser Ser Leu
                740                 745                 750

Leu Thr Asn Lys Leu Glu Gln Gln Met Gln Asp Ser Leu Phe Gly Asp
        755                 760                 765

Gly Leu Ile Pro Ser Trp Cys Ile Tyr Leu Val Glu Thr Cys Pro Phe
        770                 775                 780

Leu Leu Ser Phe Glu Ala Arg Trp Lys Tyr Phe Cys Leu Thr Ala His
785                 790                 795                 800

His Ser Phe Met Thr Asp Glu Ala Ser Ser Ser Thr Glu Thr Lys Lys
                805                 810                 815

Tyr Ser Val Thr Arg Ser Lys Ile Leu Glu Asp Ala Ser Ser Met Leu
                820                 825                 830

Asn Lys His Gly Ser Asp Thr Lys Phe Ile Glu Val Glu Phe Asp Gly
        835                 840                 845

Glu Val Gly Thr Gly Arg Gly Pro Thr Phe Glu Phe Tyr Thr Thr Val
        850                 855                 860

Ser His Glu Leu Gln Arg Val Gly Leu Gly Met Trp Arg Gly Asp Asp
865                 870                 875                 880

Thr Ser Gln Glu Cys Glu Ala Gly Phe Val His Ala Pro Phe Gly Leu
                885                 890                 895

Phe Pro Gln Pro Trp Ser Ser Ala Asn Thr Ser Ser Gln Gly Ile Ser
                900                 905                 910

Leu Ser Asn Val Val Gln Lys Phe Lys Leu Leu Gly His Leu Val Ala
        915                 920                 925

Arg Ala Val Leu Asp Gly Arg Val Leu Asp Ile Pro Leu Ser Lys Ala
        930                 935                 940

Phe Tyr Lys Ile Met Leu Glu Gln Asp Leu Asp Ile Tyr Asp Ile Pro
945                 950                 955                 960

Ser Phe Asp Pro Lys Leu Gly Lys Thr Val Met Glu Phe Gln Ala Leu
                965                 970                 975

Val Lys Arg Lys Lys Phe Leu Glu Glu Arg Ala Ser Asn Pro Ala Ala
                980                 985                 990

Asp Leu Ser Tyr Lys Asn Val Arg Leu Glu Asp Leu Cys Leu Asp Phe
        995                 1000                1005

Thr Leu Pro Gly Asn Pro Glu Tyr Glu Leu Val Pro Gly Gly Ser
        1010                1015                1020

Glu Lys Met Val Thr Leu Asp Asn Leu Glu Glu Tyr Val Ser Ser
        1025                1030                1035

Ile Val Asp Ala Thr Leu Lys Ser Gly Ile Ser Asn Gln Ile Glu
        1040                1045                1050

Ala Phe Lys Ala Gly Ile Asn Lys Val Phe Ala Leu Lys Thr Leu
        1055                1060                1065

Arg Leu Phe Ser Glu Asp Glu Met Glu Arg Ile Leu Cys Gly Glu
        1070                1075                1080
```

-continued

```
Gln Asp Ser Trp Ala Ser Asn Lys Leu Glu Asp His Ile Asn Phe
    1085            1090                1095

Asp Tyr Gly Tyr Asp Ala Asn Ser Ala Ser Val Ile Ser Phe Leu
    1100            1105                1110

Glu Ile Leu Arg Glu Phe Gly Arg Glu Asp Gln Arg Ala Phe Leu
    1115            1120                1125

His Phe Thr Thr Gly Ala Pro Gln Leu Pro Leu Gly Gly Leu Ala
    1130            1135                1140

Ser Leu Asp Pro Lys Leu Thr Val Val Arg Lys Gln Cys Asp Gly
    1145            1150                1155

Lys Val Asp Asn Glu Leu Pro Ser Val Asn Thr Cys Arg His Phe
    1160            1165                1170

Phe Lys Leu Pro Pro Tyr Ser Ser Lys Glu Ile Met Arg Gln Lys
    1175            1180                1185

Leu Lys Tyr Ala Ile Lys Glu Gly Leu Gly Ser Phe Gln Leu Ser
    1190            1195                1200
```

DROUGHT RESISTANCE IN PLANTS: UPL4

CROSS-REFERENCE TO RELATED APPLICATIONS

The present application is a Divisional Application of U.S. patent Ser. No. 14/377,842, filed Aug. 8, 2014, which is a National Stage of International Application No. PCT/NL2013/050100 filed on Feb. 18, 2013, which claims the benefit of U.S. Application No. 61/599,963 filed on Feb. 17, 2012, the entire disclosures of which are incorporated herein by reference.

TECHNICAL FIELD

The present invention relates to a method for increasing drought resistance of a plant. The method encompasses the impairment of the expression of a gene or genes or a protein in said plant. In comparison to a plant not manipulated to impair the expression of said gene(s) or protein(s), the plants display improved drought resistance. Also provided are plants and plant product that can be obtained by the method according to the invention.

BACKGROUND OF THE INVENTION

Abiotic stresses, such as drought, salinity, extreme temperatures, chemical toxicity and oxidative stress are threats to agriculture and it is the primary cause of crop loss worldwide (Wang et al. (2003) Planta 218(1) 1-14).

In the art, several reports are available dealing with the biochemical, molecular and genetic background of abiotic stress (Wang et al. (2003) Planta 218(1) 1-14 or Kilian et al (2007) Plant J 50(2) 347-363). Plant modification to deal with abiotic stress is often based on manipulation of genes that protect and maintain the function and structure of cellular components. However, due to the genetically complex responses to abiotic stress conditions, such plants appear to be more difficult to control and engineer. Wang, (Wang et al. (2003) Planta 218(1) 1-14), inter alia, mentions that one of the strategies of engineering relies on the use of one or several genes that are either involved in signalling and regulatory pathways, or that encode enzymes present in pathways leading to the synthesis of functional and structural protectants, such as osmolytes and antioxidants, or that encode stress-tolerance-conferring proteins.

Although improvements in providing abiotic stress tolerant plants have been reported, the nature of the genetically complex mechanisms underlying it provides a constant need for further improvement in this field. For example, it has been reported that genetically transformed drought tolerant plants generally may exhibit slower growth and reduced biomass (Serrano et al (1999) J Exp Bot 50:1023-1036) due to an imbalance in development and physiology, thus having significant fitness cost in comparison with plants that are not transformed (Kasuga et al. (1999) Nature Biot. Vol. 17; Danby and Gehring (2005) Trends in Biot. Vol. 23 No. 11).

Several biotechnological approaches are proposed in order to obtain plants growing under stress conditions. Plants with increased resistance to salt stress are for example disclosed in WO03/020015. This document discloses transgenic plants that are resistant to salt stress by utilizing 9-cis-epoxycarotenoid dioxygenase nucleic acids and polypeptides.

Plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291). There remains a need for new, alternative and/or additional methodology for increasing resistance to abiotic stress, in particular abiotic stress like drought.

It is an object of the current invention to provide for new methods to increase drought resistance in a plant. With such plant it is, for example, possible to produce more biomass and/or more crop and plant product derived thereof if grown under conditions of low water availability/drought in comparison with plants not subjected to the method according to the invention.

SUMMARY OF THE INVENTION

The present invention provides a method for producing a plant having improved drought resistance compared to a control plant, comprising the step of impairing expression of a UPL protein in a plant, said UPL protein comprising an amino acid sequence comprising at least one Pfam HECT domain according to PF00632 and at least one Superfamily ARM repeat according to model SSF48371, and optionally regenerating said plant.

In another aspect, the present invention provides a method for producing a plant having improved drought resistance compared to a control plant, comprising the step of impairing expression of functional UPL4 protein in a plant, plant cell or plant protoplast, wherein said functional UPL4 protein comprises an amino acid sequence comprising at least 35% identity with the amino acid sequence of SEQ ID NO:2, and optionally regenerating said plant.

Said functional UPL4 protein may comprise an amino acid sequence comprising at least one Pfam HECT domain according to PF00632 and at least one Superfamily ARM repeat according to model SSF48371.

The functional UPL4 protein may be a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed.

The invention is further directed to a method for producing a plant having improved drought resistance compared to a control plant, comprising the step of impairing expression of functional UPL4 protein in a plant, plant cell or plant protoplast, wherein said functional UPL4 protein comprises an amino acid sequence having at least one Pfam HECT domain according to PF00632 and at least one Superfamily ARM repeat according to model SSF48371, and optionally regenerating said plant.

The invention also pertains to a method for producing a plant having improved drought resistance compared to a control plant, comprising the step of impairing expression of functional UPL4 protein, wherein said functional UPL4 protein is encoded by a nucleic acid sequence comprising a nucleic acid sequence having at least 60% identity with the nucleic acid sequence of SEQ ID NO:1, and optionally regenerating said plant.

The functional UPL4 protein may be a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed.

The step of impairing expression of functional UPL4 protein may comprise mutating a nucleic acid sequence encoding said functional UPL4 protein. Mutating said nucleic acid sequence may involve an insertion, a deletion and/or substitution of at least one nucleotide. The step of impairing expression may comprise gene silencing. The step of impairing expression may comprise impairing expression of two or more functional UPL4 proteins in said plant.

The method may further comprise the step of producing a plant or plant product from the plant having improved drought resistance.

The invention also relates to the use of an amino acid sequence having at least 35% identity with the amino acid sequence of SEQ ID NO:2 or a nucleic acid sequence having at least 60% identity with the nucleic acid sequence of SEQ ID NO: 1 in the screening for drought resistance in plants.

The invention is directed to use of an UPL4 amino acid sequence having SEQ ID NO:2 or a UPL4 nucleic acid sequence of SEQ ID NO:1 in the screening for drought resistance in *Arabidopsis thaliana* plants.

The invention is also concerned with use of at least part of a UPL4 nucleic acid sequence of SEQ ID NO:1 or at least part of an UPL4 amino acid sequence of SEQ ID NO:2 as a marker for breeding drought resistant *Arabidopsis thaliana* plants.

The invention further provides use of a functional UPL4 protein as defined herein for modulating, preferably increasing, drought resistance of a plant.

In another aspect, the invention provides use of a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed for growing under drought stress conditions, wherein said drought stress conditions cause a control plant, plant cell or plant product wherein expression of said functional UPL4 protein is not impaired to show signs of drought stress such as wilting signs earlier than the plant, plant cell, or plant product wherein expression of functional UPL4 protein is impaired.

The invention also teaches a *Solanum lycopersicum, Gossypium hirsutum, Glycine max, Triticum* spp., *Hordeum vulgare., Avena sativa, Sorghum bicolor, Secale cereale,* or *Brassica napus* plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell, or plant product may comprise a disrupted endogenous UPL4 gene.

DEFINITIONS

Figure 1:
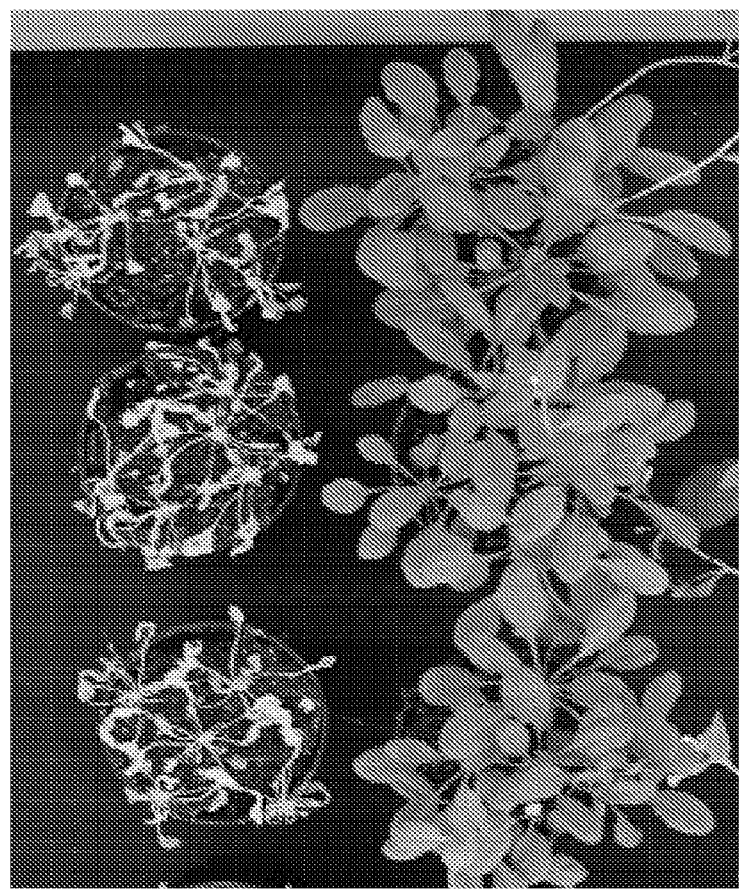
FIG. 1 shows the results of a typical experiment described in the Examples 1 and 2.

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

Aligning and alignment: With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment). "Ectopic expression" refers to expression in a tissue in which the gene is normally not expressed. "Expression of a protein" is used herein interchangeably with the term expression of a gene. It refers to the process in which a DNA region, which is operably linked to appropriate regulatory regions, particularly a promoter, is transcribed into an mRNA and which is subsequently translated into a protein or peptide (or active peptide fragment).

"Functional", in relation to UPL4 proteins (or variants, such as orthologs or mutants, and fragments), refers to the capability of the gene and/or encoded protein to modify the (quantitative and/or qualitative) drought resistance, e.g., by modifying the expression level of the gene (e.g. by overexpression or silencing) in a plant. For example, the functionality of a UPL4 protein obtained from plant species X can be tested by various methods. Preferably, if the protein is functional, silencing of the gene encoding the protein in plant species X, using e.g. gene silencing vectors, will lead to a improved drought resistance as can be tested as explained herein in detail. Also, complementation of a UPL4 knockout with a functional UPL4 protein will be capable of restoring or conferring the characteristic, in this case will restore drought sensitivity. The skilled person will have no difficulties in testing functionality.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sequence sites.

The term "cDNA" means complementary DNA. Complementary DNA is made by reverse transcribing RNA into a complementary DNA sequence. cDNA sequences thus correspond to RNA sequences that are expressed from genes. As mRNA sequences when expressed from the genome can undergo splicing, i.e. introns are spliced out of the mRNA and exons are joined together, before being translated in the cytoplasm into proteins, it is understood that expression of a cDNA means expression of the mRNA that encodes for the cDNA. The cDNA sequence thus may not be identical to the genomic DNA sequence to which it corresponds as cDNA may encode only the complete open reading frame, consisting of the joined exons, for a protein, whereas the genomic DNA encodes and exons interspersed by intron sequences. Genetically modifying a gene which encodes the cDNA may thus not only relate to modifying the sequences corresponding to the cDNA, but may also involve mutating intronic sequences of the genomic DNA and/or other gene regulatory sequences of that gene, as long as it results in the impairment of gene expression.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. Hence, the percentage of identity of a nucleotide sequence to a reference nucleic acid sequence is calculated over the entire length of the reference nucleic acid sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 2 is intended that the amino acid sequence of the polypeptide is identical to the reference sequence except that the polypeptide sequence may include up to five amino acid alterations per each 100 amino acids of the reference amino acid of SEQ ID NO: 2. Hence, the percentage of identity of an amino acid sequence to a reference amino acid sequence is calculated over the entire length of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

A nucleic acid according to the present invention may include any polymer or oligomer of pyrimidine and purine bases, preferably cytosine, thymine, and uracil, and adenine and guanine, respectively (See Albert L. Lehninger, *Principles of Biochemistry*, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked may mean that the DNA sequences being linked are contiguous.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

"Transgenic plant" or "transformed plant" refers herein to a plant or plant cell having been transformed, e.g. by the introduction of a non-silent mutation in an endogenous gene or part there of. Such a plant has been genetically modified to introduce for example one or more mutations, insertions and/or deletions in the gene and/or insertions of a gene silencing construct in the genome. A transgenic plant cell may refer to a plant cell in isolation or in tissue culture, or to a plant cell contained in a plant or in a differentiated organ or tissue, and both possibilities are specifically included herein. Hence, a reference to a plant cell in the description or claims is not meant to refer only to isolated cells or protoplasts in culture, but refers to any plant cell, wherever it may be located or in whatever type of plant tissue or organ it may be present.

Targeted nucleotide exchange (TNE) is a process by which a synthetic oligonucleotide, partially complementary to a site in a chromosomal or an episomal gene directs the reversal of a single nucleotide at a specific site. TNE has been described using a wide variety of oligonucleotides and targets. Some of the reported oligonucleotides are RNA/DNA chimeras, contain terminal modifications to impart nuclease resistance.

As used herein, the term "drought stress" or "drought" refers to a sub-optimal environmental condition associated with limited availability of water to a plant. Limited availability of water may occur when for instance rain is absent or lower and/or when the plants are watered less frequently than required. Limited water availability to a plant may also occur when for instance water is present in soil, but can not efficiently be extracted by the plant. For instance, when soils strongly bind water or when the water has a high salt content, it maybe more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "improved drought resistance" refers to plants which, when provided with improved drought resistance, when subjected to drought or drought stress do not show effects or show alleviated effects as observed in plants not provided with improved drought resistance. A normal plant has some level of drought resistance. It can easily be determined whether a plant has improved drought resistant by comparing a control plant with a plant provided with improved drought resistance under controlled conditions chosen such that in the control plants signs of drought can be observed after a certain period, i.e. when the plants are subjected to drought or drought stress. The plants with improved drought resistance will show less and/or reduced signs of having been subjected to drought, such as wilting, as compared to the control plants. The skilled person knows how to select suitable conditions such as for example the controlled conditions in the examples. When a plant has "improved drought resistance", it is capable of sustaining normal growth and/or normal development when being subjected to drought or drought stress would otherwise would have resulted in reduced growth and/or reduced development of normal plants. Hence, "improved drought resistance" is a relative term determined by comparing plants, whereby the plant most capable of sustaining (normal) growth under drought stress is a plant with "improved drought resistant" plant. The skilled person is well aware how to select appropriate conditions to determine drought resistance of a plant and how to measure signs of droughts, such as described in for example manuals provided by the IRRI, Breeding rice for drought prone environments, Fischer et al., 2003, and by the CIMMYT, Breeding for drought and nitrogen stress tolerance in maize: from theory to practice, Banzinger et al, 2000. Examples of methods determining improved drought resistance in plants are provided in Snow and Tingey, 1985, Plant Physiol, 77, 602-7 and Harb et al., Analysis of drought stress in *Arabidopsis*, A O P 2010, Plant Physiology Review, and as described in the example section below.

DETAILED DESCRIPTION OF THE INVENTION

The current invention relates to the improvement of drought resistance of a plant by impairing the expression of a functional UPL4 protein in said plant. The improvement is relative to a control plant, in which such modification has not been introduced or is not present and in which expression of a functional UPL4 protein is not impaired. In other words, modified plant according to the invention is, in comparison to the control plant, i.e. non-modified plant, better able to grow and survive under conditions of reduced water availability, (temporary) water-deprivation or conditions of drought. It is understood that according to the invention modifying, e.g., impairing, expression of functional UPL4 protein may involve genetic modification, e.g., of UPL4 gene expression, or targeted nucleotide exchange.

Genetic modification includes introducing mutations, insertions, deletions in the nucleic acid sequence of interest and/or insertion of gene silencing constructs into a genome of a plant or plant cell that target the nucleic acid sequence of interest. Genetically modifying a nucleic acid sequence, e.g., a gene, which encodes the mRNA may not only relate to modifying exon sequences corresponding to the mRNA sequence, but may also involve mutating intronic sequences of genomic DNA and/or (other) gene regulatory sequences of that nucleic acid sequence, e.g., gene.

In the context of the present invention, the functional UPL4 protein may be a protein that, when expressed in an *Arabidopsis thaliana* T-DNA insertion line having a disrupted endogenous UPL4 gene, such as an At5g02880 knockout line, e.g., SALK_091246C (http://www.*arabidopsis*.org/servlets/ SeedSearcher?action=detail&stock_number=SALK_091 246C) recited herein, results in a plant with an impaired drought resistance compared to the drought resistance of said *Arabidopsis thaliana* T-DNA insertion line having a disrupted endogenous UPL4 gene, e.g., an At5g02880 knockout line, e.g., SALK_091246C, in which said functional UPL4 protein is not expressed.

The term "disrupted endogenous UPL4 gene" as used herein refers to a UPL4 gene naturally present in the genome of a plant which is disrupted, e.g., interrupted, e.g., by means of a T-DNA insertion into said UPL4 gene. Disruption of said endogenous UPL4 gene may result in the absence of expression of said endogenous UPL4 gene, and thus in the absence of endogenous UPL4 protein (either functional or non-functional).

The term "control plant" as used herein refers to a plant of the same species, preferably of the same variety, preferably of the same genetic background.

The current invention also relates to the modulation of drought resistance of a plant by modifying the expression of functional UPL4 protein in said plant. The modulation is relative to a control plant (preferably of the same species and/or variety, and preferably of the same genetic background) in which such modification has not been introduced or is not present.

In an aspect, the present invention provides a method for producing a plant having improved drought resistance compared to a control plant, comprising the step of impairing expression of a UPL protein in a plant, said UPL protein comprising an amino acid sequence comprising at least one Pfam HECT domain according to PF00632 and at least one Superfamily ARM repeat according to model SSF48371.

In another aspect, the invention is concerned with a method for producing a plant having improved drought resistance compared to a control plant, the method comprising the step of impairing the expression of functional UPL4 protein in said plant.

"Impairing expression of a functional UPL4 protein" as used herein may mean that the expression of the UPL4 gene is impaired, and/or that expression of the UPL4 gene is normal but translation of the resulting mRNA is inhibited or prevented (for example, by RNA interference), and/or that the amino acid sequence of UPL4 protein has been altered such that its ubiquitin protein ligase specific activity is reduced compared to the ubiquitin protein ligase specific activity of the protein as depicted in SEQ ID NO:2, preferably under physiological conditions, particularly identical physiological conditions. Alternatively, a UPL4 protein may become non-functional or less functional by scavenging thereof using UPL4 inhibitors such as an antibody specifically binding to said UPL4 protein, or other UPL4 inhibitors, e.g., proteins that stop, prevent, or reduce the activity of a UPL4 proteins, or chemical inhibitors such as ions, or metals, or scavenging of cofactors. For example, an antibody specifically binding to said UPL4 protein may be expressed simultaneously with said UPL4 protein, thereby reducing its specific activity. The ubiquitin protein ligase specific activity of a UPL4 protein may be considered "reduced" if the ubiquitin protein ligase specific activity of such protein is statistically significantly less than the ubiquitin protein ligase specific activity of the protein as depicted in SEQ ID NO:2. The ubiquitin protein ligase specific activity of a UPL4 protein may, for example, be reduced by at least 5%, 10%, 15%, 20%, 25%, 30%, 35%, 40%, 45%, 50%, or more. Reduced expression of the endogenous UPL4 gene of a plant may be accomplished by altering the promoter sequence, for example, using targeted mutagenesis. The skilled person will be capable of determining ubiquitin protein ligase specific activity based on routine methods.

It is believed by the current inventors that impairing expression (e.g. by reducing, repressing or deleting expression and/or activity) of functional UPL4 protein leads to the absence or a reduced level of functional UPL4 protein, either as a consequence of low expression, e.g. via RNA interference, or as a consequence of decreased activity/functionality of the UPL4 protein, or one or more of the above, and that said absence or reduced level of functional UPL4 protein leads to decreased need for water or improved resistance to drought of said plant.

Ubiquitin Protein Ligase proteins (UPLs) are known to be involved in the selective degradation of regulatory proteins in both yeast and animals (Huibregtse et al. (1995) Proc. Natl. Acad. Sci. USA 92, 2563-2567; Pickart (2001) Annu. Rev. Biochem. 70, 503-533). Proteins committed for degradation are modified with a chain of multiple Ubiquitins and are then recognized by the 26S proteasome. An important class of these Ubiquitin Protein Ligase proteins is formed by the HECT E3s, which comprise a conserved 350-amino acid domain called the HECT domain at the C-terminal end (based on its homology to the C-terminus of human E6-Associated Protein (E6-AP) (Huibregtse et al. (1995) Proc. Natl. Acad. Sci. USA, 92, 2563-2567). The HECT domain includes a highly conserved region surrounding the positionally invariant cystein required to catalyze Ubiquitin transfer.

According to Downes et al. (2003, Plant J 35, 729-742), plants also contain HECT E3s, with seven present in *Arabidopsis*: UPL1, UPL2, UPL3, UPL4, UPL5, UPL6, and UPL7. Downes et al. further describe that UPL1, UPL2, UPL3, UPL4, UPL5, UPL6, and UPL7 can be grouped by structure into four subfamilies based on intron/exon positions of the corresponding genes, protein sequence and length, and the presence of additional protein motifs upstream of the HECT domain: UPL1/2, UPL3/4, UPL5, and UPL6/7. The presence of a variety of domains upstream of the HECT domain suggests that individual members of the UPL1-UPL7 family have distinct sets of targets and functions (see Downes et al. 2003 The Plant Journal, 35, 729-742, in particular FIG. 1 thereof, for more information on the distinct characteristics of the different UPL proteins).

In *Arabidopsis thaliana*, Ubiquitin Protein Ligase 4 can be distinguished from Ubiquitin Protein Ligase 3 for instance by the absence of a 225-residue region 650 amino acids from the C-terminus of Ubiquitin Ligase 4 (Downes et al. (2003) Plant J 35, 729-742).

Ubiquitin Protein Ligase 4 as found in *Arabidopsis thaliana* has been reported to have approximately 54% amino acid sequence identity to Ubiquitin Protein Ligase 3 (Downes et al. (2003) Plant J 35, 729-742). The locus name of the Ubiquitin Protein Ligase 4 is At5g02880, and the ORF name is F9G14 (both according to www.uniprot.org/uniprot/Q9LYZ7).

The UPL4 protein of *Arabidopsis thaliana* is comprised of 1502 amino acids (as depicted in SEQ ID NO:2). The cDNA encoding the UPL4 protein of *Arabidopsis thaliana* comprises 4506 nucleotides (depicted in SEQ ID NO:1). The UPL4 gene of *Arabidopsis thaliana* is also referred to as KLI5 (for Kaktus Like on chromosome 5) based on its similarity with the KAKTUS gene in *Arabidopsis* (see Refy et al. Mol Gen Genomics (2003) 270: 403-414).

A "UPL4 protein" as used herein comprises the protein depicted in SEQ ID NO:2, as well as fragments and variants thereof. Variants of a UPL4 protein include, for example, proteins having at least 40%, 50%, 60%, 70%, 75%, 80%, 85%, 90%, 95%, 96%, 97%, 98%, 99%, or more, such as 100%, amino acid sequence identity, preferably over the entire length, to SEQ ID NO:2. Amino acid sequence identity is determined by pairwise alignment using the Needleman and Wunsch algorithm and GAP default parameters as defined above.

An *Arabidopsis thaliana* plant having a T-DNA insertion in the gene encoding UPL3 is known from Downes et al. ((2003) Plant J. 35, 729-742). This UPL3 mutant shows aberrant trichome development. Downes et al. also describe an *Arabidopsis thaliana* plant having a T-DNA insertion in the gene encoding UPL4. Downes et al describe that, in contrast to the UPL3 mutant, the UPL4 mutant showed no abnormal phenotypes when grown under optimal growth conditions and developed normal trichomes.

In another aspect there is provided for a method for producing a plant having improved drought resistance, the method comprising the step of impairing the expression in said plant of a gene encoding a UPL4 protein.

"Impaired expression" according to the present invention denotes the absence or reduced presence of a functional UPL4 protein and variants thereof comprising an amino acid sequence with more than 40%, 50%, 60%, 70%, 80%, 90%, 95% sequence identity therewith. It also denotes the absence of lowered presence of proteins described herein that comprise at least one Pfam HECT domain, PF00632, and at least one Superfamily ARM repeat, model SSF48371. A skilled person is well aware of the many mechanism available to him in the art to impair the expression of a gene at for example the transcription level or the translation level.

In another aspect there is provided for a method for increasing drought resistance of a plant, the method comprising the step of impairing the expression in said plant of a gene, wherein the amino acid sequence (or protein) encoded by said gene comprises at least one Pfam HECT domain (PF00632) and at least one Superfamily ARM repeat (model SSF48371), as determined as described below. It is understood that the phrase "at least one Superfamily ARM repeat model SSF48371" comprises the four Armadillo repeat sequences from the UPL4 gene of the amino acid sequence of FIG. 3. Thus, the phrase "at least one Superfamily ARM repeat model SSF48371" means to comprise the four Armadillo repeat sequences.

As used herein "Pfam" or "PFAM" refers to a large collection of multiple sequence alignments and hidden Markov models covering many common protein families, and is available from http://pfam.sanger.ac.uk/. The Pfam database contains a large collection of protein families, each represented by multiple alignments. These alignments have been used to build hidden Markov models (HMMs) for each protein domain family. The alignments represent evolutionary conserved structures and the presence of a domain in a protein of interest can be indicative towards its biological function. Profile hidden Markov models (profile HMMs) built from the Pfam alignments are useful for automatically recognizing that a new protein belongs to an existing protein family even if the homology by alignment appears to be low. Other proteins in the same protein family are identified by querying the amino acid sequence of a protein sequence against the Hidden Markov Model using HMMER software. The HMMER software (version 3.0 from http://hmmer.janelia.org/) is able to use this HMM to search for a presence of this domain in new sequences. Potential candidate proteins hits were derived by taking into account only HMMER hits in their sequences that were above the default inclusion threshold.

Pfam version 24.0 (October 2009) contains alignments and models for 11912 protein families (see The Pfam protein families database: R. D. Finn, et al Nucleic Acids Research (2010) Database Issue 38:D211-222). Pfam is based on a sequence database called Pfamseq, which is based on UniProt release 15.6 (Swiss-Prot release 57.6 and SP-TrEMBL release 40.6).

The alignments in the Pfam database represent evolutionary conserved structures that may be relevant for a protein's function. The hidden Markov models (HMMs) built from the Pfam alignments are useful for establishing if a protein belongs to an existing protein family. This is even the case if homology/identity by alignment would be low. Once, for example, a protein which is involved in a certain characteristic (e.g. sensitivity to drought) is recognized, and, for example, impairment of its expression imparts an enhanced trait (e.g. increased resistance to drought), other proteins in the same protein family can be identified by the skilled person by comparing the amino acid sequence of a protein (and encoded by candidate DNA) against the Hidden Markov Model which characterizes the Pfam domain (in the current invention Pfam HECT PF00632 model) using HMMER software (http://hmmer.janelia.org/'version. HMMER version 3.0 was released on Mar. 28, 2010).

After establishment of the presence of a Pfam HECT domain (PF00632) as described above, a candidate protein also has to meet the requirement of comprising at least on Superfamily ARM repeat (HMM model SSF48371; http://supfam.org/SUPERFAMILY/cgi-bin/scop.cgi?ipid=SSF48371, as can be established by, for example using the InterProScan application (http://www.ebi.ac.uk/Tools/pfa/iprscan/; Quevillon et al. (2005) 33(2) W116-W120; E. M. Zdobnov and R. Apweiler (2001) Bioinformatics, 17, 847-848). Quevillon and colleagues describe that the InterProScan is a tool that combines different protein signature recognition methods from the InterPro consortium member databases into one resource, with distinct publicly available databases in the application. Protein as well as DNA sequences can be analyzed. A web-based version is accessible for academic and commercial organizations from the EBI (http://www.ebi.ac.uk/InterProScan/).

The SUPERFAMILY annotation is based on a collection of hidden Markov models, which represent structural protein domains at the SCOP superfamily level. A superfamily groups together domains which have an evolutionary relationship. The annotation is produced by scanning protein sequences from over 1,400 completely sequenced genomes against the hidden Markov models.

All software is applied under default settings.

In summary, a Hidden Markov model for the HECT domain (PF00632 model http://pfam.sanger.ac.uk/family?acc=PF00632) was obtained from the Pfam database (version 24 from http://pfam.sanger.ac.uk/) and placed into a separate file. The HMMER software was used to determine that the amino proteins sequences are characterized by the Pfam HECT domain. In addition, the filtered protein set was further reduced by employing the SuperFamily package (using the SSF48371 model http://supfam.org/SUPERFAMILY/cgi-bin/scop.cgi?ipid=SSF48371) from the InterProScan application (http://www.ebi.ac.uk/Tools/pfa/iprscan/) (Quevillon et al. to mine for ARM repeats. Furthermore, the sequences were aligned using the MUSCLE multiple alignment tool. The phylogenetic tree was inferred using the protpars algorithm from the PHYLIP package. (Plant) Proteins meeting both requirements (having a Pfam HECT PF00632 domain and a SuperFamily SSF48371 model Arm repeat), are proteins according to the invention; and impairment of the expression thereof may be useful in providing improved/increased drought resistance to the plant, and examples of such proteins and cDNA are disclosed herein. The skilled person is well aware on how to determine and test based on the information provided above.

Without being bound by theory, the current inventors speculate that the presence of this combination of domains in the protein according to the invention increases sensitivity of the plants for drought, and that impairment of the expression of such proteins having these domains, improves resistance of a plant to drought.

Impairment at the transcriptional level can be the result of the introduction of one or more mutations in transcription regulation sequences, including promoters, enhancers, initiation, termination or intron splicing sequences. These sequences are generally located 5' of, 3' of, or within the coding sequence of the genes according to the invention. Independently, or at the same time, impairment of expression can also be provided by deletion, substitution, rearrangement or insertion of nucleotides in the coding region of the genes.

For example, in the coding region, nucleotides may be substituted, inserted or deleted leading to the introduction of one, two or more premature stop-codons. Also, insertion, deletion, rearrangement or substitution can lead to modifications in the amino acid sequence encoded, and thereby providing for impaired expression of functional UPL4 protein. Even more, large parts of the genes may be removed, for example, at least 10%, 20%, 30%, 40%, 50%, 60%, 70%, 80%, 90% or even 100% of the (coding region) of the gene is removed from the DNA present in the plant, thereby impairing the expression of functional UPL4 protein.

Alternatively, one, two, three of more nucleotides may be introduced in the gene or genes encoding for a UPL4 protein, either leading to, for example, a frame-shift, or leading to the introduction of a sequence encoding additional amino acids, or the introduction of sequence not encoding amino acids, or the introduction of large inserts, thereby impairing the provision/expression of functional UPL4 protein.

In other words, deletion, substitution or insertion of nucleotide(s) in a nucleotide sequence encoding a UPL4 protein, as described above, may lead to, for example, a frame shift, an introduction of a stop codon, or the introduction of a non-sense codon. In particular the introduction of a stop codon and the introduction of a frame shift mutation are generally accepted as efficient ways to produce a knockout plant, that is, a plant with reduced, repressed or deleted expression and/or activity of a specific protein.

A frame shift mutation (also called a framing error or a reading frame shift) is a genetic mutation caused by indels (insertions or deletions) of a number of nucleotides that is not evenly divisible by three in a nucleotide sequence. Due to the triplet nature of gene expression by codons, the insertion or deletion can change the reading frame (the grouping of the codons), resulting in a completely different translation from the original. The earlier in the sequence the deletion or insertion occurs, the more altered the protein produced is. A frame shift mutation will in general cause the reading of the codons after the mutation to code for different amino acids, but there may be exceptions resulting from the redundancy in the genetic code. Furthermore, the stop codon ("UAA", "UGA" or "UAG") in the original sequence will not be read, and an alternative stop codon may result at an earlier or later stop site. The protein produced may be abnormally short or abnormally long.

The introduction of a stop codon in a nucleotide sequence encoding a UPL4 protein as defined herein may result in a premature stop of transcription, which generally results in a truncated, incomplete, and non-functional UPL4 protein. Preferably, the stop codon is introduced early in the transcription direction. The earlier in the nucleotide sequence the stop codon is introduced, the shorter and the more altered the protein produced is. The introduction of a nonsense codon in a nucleotide sequence encoding a UPL4 protein may result in transcript mRNA wherein e.g. one codon no longer codes for the amino acid as naturally occurring in UPL4, for example a codon that normally codes for an amino acid which is essential for a UPL4 protein to be functional. Hence, such UPL4 protein may not be functional.

In other words, the impairment may comprise mutating one or more nucleotides in the genes disclosed herein resulting either in the presence of less or even in the total absence of protein expression product (i.e. the absence of protein that would be obtained when the genes according to the invention were not modified as described above), or in the presence of non-functional protein.

Therefore, in one embodiment of the method disclosed herein, the impairment is the consequence of one or more mutations in said gene resulting in the presence of less protein expression product or absence of a protein expression product.

The term inhibition/presence of less as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

As will be understood by a skilled person, a mutation may also be introduced in a nucleotide sequence encoding UPL4 as defined herein by the application of mutagenic compounds, such as ethyl methanesulfonate (EMS) or other compounds capable of (randomly) introducing mutations in nucleotide sequences. Said mutagenic compounds or said other compound may be used as a means for creating plants harboring a mutation in a nucleotide sequence encoding a UPL4 protein.

Alternatively, the introduction of a mutation in a nucleotide sequence encoding a (UPL4) protein according to the invention may be effected by the introduction of transfer-DNA (T-DNA) in the nucleotide sequence encoding such protein, for instance T-DNA of the tumor-inducing (Ti) plasmid of some species of bacteria such as *Agrobacterium tumefaciens*. A T-DNA element may be introduced in said nucleotide sequence, leading to either a non-functional protein or to the absence of expression of the protein, consequently decreasing the need for water of a plant obtained by the method according to the invention (see for example Krysan et al. 1999 The Plant Cell, Vol 11. 2283-2290). Likewise advantage can be taken from the use of transposable element insertion (See for Example Kunze et al (1997) Advances in Botanical Research 27 341-370 or Chandlee (1990) Physiologia Planta 79(1) 105-115).

In an embodiment, introducing a mutation in a nucleotide sequence encoding a protein according to the invention is performed by targeted nucleotide exchange (TNE), for instance as described in WO2007073170. By applying TNE, specific nucleotides can be altered in a nucleotide sequence encoding UPL4, whereby, for instance, a stop codon may be introduced which may for instance result in a nucleotide sequence encoding a truncated protein according to the invention with decreased or disappeared activity.

In another embodiment there is provided a method as disclosed above wherein the impairment of expression of functional UPL4 protein is caused by expression of non-functional protein. As explained above, a skilled person has no problem in determining functionality of the genes according to the invention. For example, he may perform complementation studies, by introducing the control gene, without any modifications, into a plant in which the expression of a protein according to the invention has been impaired and study drought resistance.

Alternatively he may perform experiments analogous to those experiments described below in the examples, and determine drought resistance in a plant in which one or more mutations were introduced in the genes according to the invention, by comparison to a suitable control/wild-type plant.

Impairment can also be provided at the translational level, e.g. by introducing a premature stop-codon or by posttranslational modifications influencing, for example, protein folding.

Independent of the mechanism, impairment according to the present invention is indicated by the absence or reduced presence of functional UPL4 protein. In contrast, non-functional UPL4 protein may be present at normal levels.

As explained above the term inhibition of expression or reduced presence as used herein relates to a reduction in protein expression of at least 10%, 20%, 30%, 40%, 50%, 60%, 70%, 80%, 90% or even 99% in comparison to a control plant, in which the expression is not impaired. The term "absence of protein expression" refers to the virtual absence of any expression product, for example less than 5%, 4%, 3%, 2% or even less than 1% in comparison to the control.

According to another embodiment, impairment is caused by gene silencing, for example with RNA interference or RNA silencing.

With the help of molecular biology methods readily available to the skilled person, impairment of the genes can also be accomplished by gene silencing, for example using RNA interference techniques, dsRNA or other expression silencing techniques (see for example, Kusaba et. al (2004) Current Opinion in Biotechnology 15:139-143, or Preuss and Pikaard (2003) in RNA Interference (RNAi)-Nuts & Bolts of siRNA Technology (pp. 23-36), ©2003 by DNA Press, LLC Edited by: David Engelke, Ph.D.) or, as already discussed above, knocking out.

In another preferred embodiment, and as already discussed above, there is provided for a method according to the invention wherein the impairment is caused by insertion, deletion and/or substitution of at least one nucleotide. For example, 1, 2, 3 . . . 10, 40, 50, 100, 200, 300, 1000, or even more nucleotides may be inserted, deleted or substituted in the genes according to the invention. Also anticipated are combinations of insertion, deletion and/or substitution, either in the coding or in the non-coding regions of the gene.

In another embodiment of the method disclosed herein the method comprises the step of impairing the expression in said plant of more than 1, for example 2, 3, 4, 5, or all genes encoding a UPL4 protein.

In this embodiment, the expression of more than one gene as described above, and present in a particular plant is impaired. For example the expression of one, two, three, four, or all of the genes encoding a UPL4 protein, as present in a plant, is impaired. By impairing the expression of more genes as described above at the same time (when present in a plant) even more improved drought resistance can be achieved.

In another embodiment, the plant provided by the method according to the invention can be used for the production of further plants and or plant products derived there from. The term "plant products" refers to those material that can be obtained from the plants grown, and include fruits, leaves, plant organs, plant fats, plant oils, plant starch, plant protein fractions, either crushed, milled or still intact, mixed with other materials, dried, frozen, and so on. In general such plant products can, for example be recognized by the presence of a gene as disclosed herein so modified that the expression of a functional protein is impaired, as detailed above.

Preferably, expression and/or activity of the UPL4 protein according to the invention is impaired (e.g. reduced, repressed or deleted) in a plant belonging to the Brassicaceae family including *Brassica napus* (rape seed), Solanaceae-family, including tomato, or Curcurbitaceae family, including melon and cucumber, or the Poacease family including *Oryza*, including rice, or *Zea mays*, including maize (corn), or the Fabaceae including legume, pea, or bean. Preferably the method according to the invention is applied in tomato, rice, maize, melon, or cucumber, thereby providing a plant with decreased need for water or improved resistance to drought in comparison to a corresponding non-transformed plant. Also provided is a plant cell, plant or plant product obtainable by the method according to the invention, and wherein said plant cell, plant or plant product shows reduced expression of functional UPL4 protein, compared to a control plant not subjected to the method according to the invention.

Also provided is a plant cell, plant or plant product, characterized in that in said plant cell, plant or plant product the expression of at least one, preferably all genes encoding UPL4 protein, such as those wherein the cDNA sequence corresponding to the mRNA transcribed from said at least one gene comprises the sequence shown in SEQ ID NO:1, and those wherein the cDNA sequence corresponding to the mRNA sequence transcribed from said at least one gene comprise at least 40%, 50%, 60%, 70%, 80%, 90%, 95% identity with the nucleotide sequence of SEQ ID NO:1 and/or wherein the amino acid sequence encoded by said at least one gene comprises the sequence shown in SEQ ID NO:2, or wherein the amino acid sequence encoded by said at least one gene comprises at least 40%, 50%, 60%, 70%, 80%, 90%, 95% identity with the amino acid sequence of SEQ ID NO:2 and/or wherein the amino acid sequence encoded by said at least one gene comprises at least one Pfam HECT domain (PF00632) and at least one Superfamily ARM repeat (model SSF48371) as defined above, is impaired. Preferably the plant is not the *Arabidopsis thaliana* mutant as described in the examples below, or a *Brachypodium* T-DNA insertion mutant, or a *Zea mays* T-DNA insertion mutant, or an *Oryza sativa* T-DNA insertion mutant.

Figure 2:
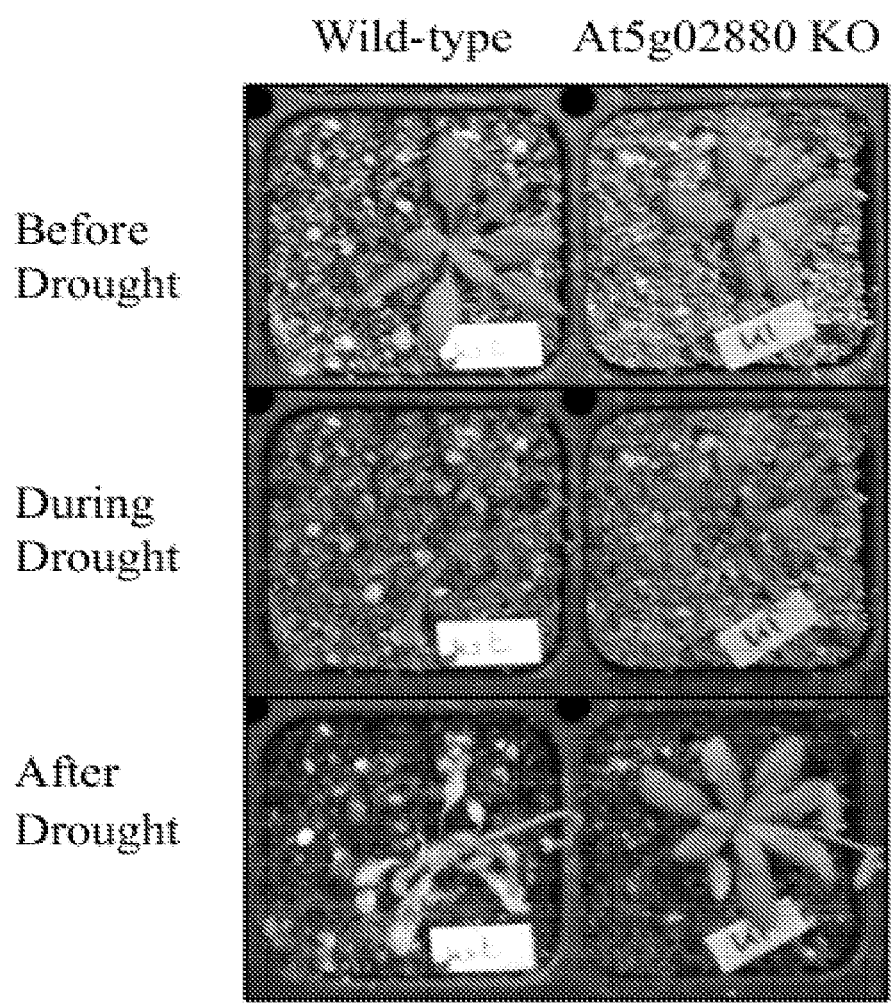
FIG. 2 shows the drought resistant phenotype of the UPL4 knockout (*Arabidopsis* At5g02880 insertion mutant) as compared to the drought sensitive phenotype of a control (wild-type) plant.

In another aspect there the invention is directed to a use of a gene wherein the cDNA sequence corresponding to the mRNA sequence transcribed from said gene comprises the sequence shown in SEQ ID NO: 1 and FIG. 2, and those wherein the cDNA sequence corresponding to the mRNA sequence transcribed from said gene comprises at least 40%, 50%, 60%, 70%, 80%, 90%, 95% identity therewith and/or wherein the amino acid sequence encoded by said gene comprises the sequence shown in SEQ ID NO:2, and amino acid sequence sequences with more than 35%, 40%, 50%, 60%, 70%, 80%, 90%, 95% identity therewith and/or wherein the amino acid sequence encoded by said gene comprises at least one Pfam HECT domain (PF00632) and at least one Superfamily ARM repeat (model SSF48371) as defined above, for providing increased drought resistance to a plant.

In this embodiment, the gene described can be used as a target for improving drought resistance in a plant, in accordance with the disclosure herein, or the gene can be used to identify new proteins involved in drought sensitivity and resistance.

In another embodiment a use is provided of a UPL4 sequence having SEQ ID No.1 or 2 of the *Arabidopsis thaliana* species in the screening for drought resistance in *Arabidopsis thaliana* plants. In addition, a use is provided wherein the UPL4 sequence is an analogous sequence to SEQ ID No.1 or 2 of an other plant species and wherein the screening is in plants of the other plant species. Furthermore, a method is provided for screening plants or plant cells with improved drought resistance comprising the steps of:

providing a heterogenic population of plant cells or plants of the *Arabidopsis thaliana* species;

providing a UPL4 sequence having SEQ ID No.1 or 2;

determining the sequence of at least part of the UPL4 gene of the plants cells or plants;

comparing the determined UPL4 sequences from the plant cells or plants with the provided UPL4 sequence;

identifying plant cells or plants wherein the UPL4 sequence comprises a mutation.

Alternatively, in the method, the plant cells or plants that are provided are of an other species, and wherein the UPL4 gene sequence that is provided is an analogous sequence of the other species.

Hence, by using the UPL4 sequence SEQ ID No.1 or SEQ ID No.2 of the species *Arabidopsis thaliana*, or an analogous sequence thereof from an other species, mutated UPL4 sequences can be identified in the plant species that may provide improved drought resistance. An analogous sequence, in an other species, of the UPL4 sequence SEQ ID No.1 or SEQ ID No.2 of the species *Arabidopsis thaliana* is defined as a sequence having at least 35%, 40%, 50%, 60%, 70%, 75%, 80%, 85%, 90%, 95%, or at least 99%, sequence identity therewith. The analogous UPL4 protein may have substantially the same function as SEQ ID No.1 or SEQ ID No.2.

In the method, a heterogenic population of plant cells or plants of the species is provided. The heterogenic population may for example be provided by subjecting plant cells to a mutagen that introduces random mutations thereby providing a heterogenic population of plant cell. Hence, the heterogenic population may be derived from a single plant variety, which is subjected to random mutagenesis in order to obtain a variety of mutations in the offspring thereby providing a heterogenic population. Many mutagens are known in the art, e.g. ionic radiation, UV-radiation, and mutagenic chemicals such as azides, ethidium bromide or ethyl methanesulfonate (EMS). Hence the skilled person knows how to provide for a heterogenic population of plants or plant cells. Also, the skilled person may also provide a variety of plants as a heterogenic population, i.e. not a single variety from a species. A variety of plants show genetic variety, they are not genetically identical, but because the plants are from the same species they are substantially identical. In any case, a heterogenic population of plant cells or plants may have at least 95%, 96%, 97%, 98%, 98%, 99%, 99.5% or at least 99.9% sequence identity.

By determining at least part of the sequence of the UPL4 gene sequence with the sequence of the plants or plant cells from the heterogenic population, and subsequently comparing these sequences with the provided UPL4 gene sequence (the reference), plant cells or plants can be identified that comprise a mutation in the UPL4 gene sequence. It is understood that such a comparison can be done by alignment of the sequences and that a mutation is a difference in respect of at least one nucleic acid or amino acid position in the analogous (reference) UPL4 sequence of the plant species. In this way, plants or plant cells are identified that have mutations in the UPL4 gene (e.g. insertions, deletions, substitutions) that may provide improved drought resistance.

Preferably, plants are selected that have mutations that would result in an impairment of expression of a functional UPL4 protein, such as already outlined above. Mutations that would impair expression of a functional UPL4 protein may be mutations that would disrupt the open reading frame (introduce a frame shift or a stop codon) or disrupt or otherwise alter the function of the encoded protein by altering nucleotides in codons encoding amino acids that are essential for the proper functioning of the protein, thereby leading to modified (e.g. increased) resistance to draught in comparison to the non-altered protein. The method may also be used for example in the screening and selection of plants that have been subjected to genetic modification which targets the UPL4 sequence as outlined above. Also, the UPL4 sequence may also be used in a screening assay, in which a (heterogenic) population of plants are subjected to drought.

In another embodiment, the use is provided of at least part of UPL4 having SEQ ID No.1 or SEQ ID No.2 of the *Arabidopsis thaliana* species as a marker for breeding drought resistant *Arabidopsis thaliana* plants. Also, the UPL4 sequence may be of an analogous sequence of an other species wherein the marker is for breeding drought resistant plants of the other plant species.

The present invention also relates to use of a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed for growing under drought stress conditions, wherein said drought stress conditions cause a control plant, plant cell, or plant product wherein expression of said functional UPL4 protein is not impaired to show signs of drought stress such as wilting signs earlier than the plant, plant cell, or plant product wherein expression of functional UPL4 protein is impaired.

In an aspect, the present invention pertains to a plant, plant cell or plant product obtainable or obtained by the method taught herein. Additionally, the invention provides a seed derived from such plant.

The invention also relates to a plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell or plant product may, for example, comprise a disrupted endogenous UPL4 gene.

The plant, plant cell or plant product may be any plant or plant cell, or may be derived from any plant, such as monocotyledonous plants or dicotyledonous plants, but most preferably the plant belongs to the family Solanaceae. For example, the plant may belong to the genus *Solanum* (including *lycopersicum*), *Nicotiana*, *Capsicum*, *Petunia* and other genera. The following host species may suitably be used: Tobacco (*Nicotiana* species, e.g. *N. benthamiana*, *N. plumbaginifolia*, *N. tabacum*, etc.), vegetable species, such as tomato (*Solanum lycopersicum*) such as e.g. cherry tomato, var. *cerasiforme* or currant tomato, var. pimpinellifolium) or tree tomato (*S. betaceum*, syn. *Cyphomandra betaceae*), potato (*Solanum tuberosum*), eggplant (*Solanum melongena*), pepino (*Solanum muricatum*), cocona (*Solanum sessiliflorum*) and naranjilla (*Solanum quitoense*), peppers (*Capsicum annuum*, *Capsicum frutescens*, *Capsicum baccatum*), ornamental species (e.g. *Petunia hybrida*, *Petunia axillaries*, *P. integrifolia*).

Alternatively, the plant may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (*Glycine* spp, e.g. *G. max*), cotton (*Gossypium* species, e.g. *G. hirsutum*, *G. barbadense*), *Brassica* spp. (e.g. *B. napus*, *B. juncea*, *B. oleracea*, *B. rapa*, etc), sunflower (*Helianthus annus*), safflower, yam, cassava, alfalfa (*Medicago sativa*), rice (*Oryza* species, e.g. *O. sativa* indica cultivar-group or *japonica* cultivar-group), forage grasses, pearl millet (*Pennisetum* spp. e.g. *P. glaucum*), tree species (*Pinus*, poplar, fir, plantain, etc), tea, *coffea*, oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia*, *Chrysanthemum*, *Lily*, *Gerbera* species), herbs (mint, parsley, basil, thyme, etc.), woody trees (e.g. species of *Populus*, *Salix*, *Quercus*, *Eucalyptus*), fibre species e.g. flax (*Linum usitatissimum*) and hemp (*Cannabis sativa*), or model organisms, such as *Arabidopsis thaliana*.

Preferred hosts are "crop plants", i.e. plant species which is cultivated and bred by humans. A crop plant may be cultivated for food purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork and the like.

Preferably, the plant, plant cell or plant product of the invention is not an *Arabidopsis thaliana* or *Brachypodium* plant, plant cell or plant product.

The plant, plant cell or plant product of the invention may, for example, be a *Solanum lycopersicum* or *Brassica rapa* plant, plant cell or plant product.

Thus, the invention pertains, for example, to a *Solanum lycopersicum, Gossypium hirsutum, Glycine max, Triticum* spp., *Hordeum vulgare., Avena sativa, Sorghum bicolor, Secale cereale,* or *Brassica napus* plant, plant cell, or plant product wherein expression of functional UPL4 protein is impaired, wherein the functional UPL4 protein is a protein that when expressed in an *Arabidopsis thaliana* T-DNA insertion line having a disrupted endogenous UPL4 gene results in a plant with an impaired drought resistance compared to the drought resistance of said *Arabidopsis thaliana* T-DNA insertion line having a disrupted endogenous UPL4 gene in which said functional UPL4 protein is not expressed. Said plant, plant cell, or plant product may comprise a disrupted endogenous UPL4 gene.

All references recited herein are herein incorporated by reference in their entirety.

EXAMPLES

Example 1 Drought Test

*Arabidopsis thaliana* (At) seeds transformed with *Agrobacterium tumefaciens* vector pROK2, leading to the absence of functional UPL4 protein (NASC ID: N655716, AGI code AT5G02880 and SALK_091246C; hereafter referred to a mutant seeds or mutant plants) were obtained from the Nottingham *Arabidopsis* Stock Centre (NASC; School of Biosciences, University of Nottingham, Sutton Bonington Campus, Loughborough, LE12 5RD United Kingdom). As control At Col-0 (Columbia, N60000); hereafter referred to as control seed or plant) were used.
Growth Medium:

A soil mixture comprising one part of sand and vermiculite and two parts of compost was used (sand:vermiculite: compost=1:1:2). This mixture increases the water percolation hence facilitates uniform water uptake by each pot and better water drainage. Before sowing, the seeds were kept at 4° C. for 3 days under dark and humid conditions for stratification.

Both mutant and control seeds were sown in a rectangular tray containing 8×5=40 pots of ~4 cm diameter with density of 5 plants per pot. Nutrient solution (EC=1.5) was supplied to all the plants from the bottom of the pots in the tray 10 days after germination (DAG), and at 15 DAG the plants were subjected to drought (for 15, 16, 17 or 18 days) by transferring the pots to dry trays. Subsequently, plants were rehydrated and observed for recovery after 1 week.

Three pot replicates of each genotype were included in the pre-drought screening. Total time needed for a complete test was approx. 36-39 days.
Drought Assay Examination Once the plants reached the 2 true leaves stage they were thinned to maintain exactly 5 plants per pot. At 10 DAG, plants received nutrition (EC=1.5) and at 15 DAG each pot was moved to a dry tray. From this day onwards the plants did not receive any water. Every day the plants, especially the control (or wild type) (Col-0) were observed for wilting signs. On the 15$^{th}$ day of drought (DOD), Col-0 wilted completely and did not recover upon rehydration. We determined this day as its permanent wilting point (PWP). From this day onwards one replicate from the mutant was rehydrated and observed for recovery signs and pictures were taken. The mutant showed survival for at least 2 days more under drought compared to the control and was subjected for further rigorous screening.

Example 2 Drought Test

Growth Medium:

The same mutant and control plants as in Example 1 were grown in similar tray set-up as described above in the pre-screening test. Plants were stressed by withholding water from 15 DAG until the control reached its PWP. During this period every alternate day pots were shuffled within the trays to reduce the position effects and allow uniform evaporation. On day 15 DOD, control plants reached PWP and did not recover upon rehydration. One pot replicate from the mutant was rehydrated everyday from 15 DOD onwards and checked for drought stress recovery. Pictures were taken and recovery was scored. The mutant showed recovery from drought stress for at least 3 days more after the control reached its PWP.

FIG. 1 shows a photograph comparing mutant and control, demonstrating the superior effect of the mutant with respect to resistance to drought stress.

Example 3 Drought Test

Materials and Methods
Plant Material.

A TDNA insertion line with a disrupted AT5G02880 (UPL4) gene (SALK_091246C) was obtained from the Nottingham *Arabidopsis* Stock Centre (NASC). Complementation lines were produced by stable transformation of *Arabidopsis thaliana* plants using floral dip transformation (Bent et al., 2006. Methods Mol. Biol. Vol. 343:87-103). Homologs of the *Arabidopsis thaliana* (AT5G02880) UPL4 gene were identified from several crop species, including *Brassica rapa* (cabbage), *Solanum lycopersicum* (tomato) and *Oryza sativa* (rice) and the model species *Arabidopsis thaliana* (UPL3; AT4G38600).

TABLE 1

Homologs of *Arabidopsis thaliana* UPL4 gene and UPL4 protein

| Annotation | *Arabidopsis thaliana* | *Brassica rapa* | *Solanum lycopersicum* | *Oryza sativa* |
|---|---|---|---|---|
| UPL4 | AT5G02880 (SEQ ID NO: 1 & 2; UPL4) | Br17038 (SEQ ID NO: 5 & 6) | Slg98247 (SEQ ID NO: 9 & 10) | Os05g03100 (SEQ ID NO: 11 & 12) |
| | AT4G38600 (SEQ ID NO: 3 &4; UPL3) | Br47159 (SEQ ID NO: 7 & 8) | | |

Table 2. Percentage of nucleic acid sequence identity between the *Arabidopsis thaliana* UPL4 cDNA sequence (SEQ ID NO:1) and cDNA sequences of homologues in *Arabidopsis thaliana* (At4g38600 (UPL3); SEQ ID NO:3), *Brassica rapa* (Br17038; SEQ ID NO:5 & Br47159; SEQ ID NO:7), *Solanum lycopersicum* (Sig98247; SEQ ID NO:9), and *Oryza sativa* (Os05g03100; SEQ ID NO: 1)(first column); and percentage of amino acid sequence identity between the *Arabidopsis thaliana* UPL4 protein sequence (SEQ ID NO:2) and protein sequences of homologues in *Arabidopsis thaliana* (At4g38600; SEQ ID NO:4), *Brassica rapa* (Br17038; SEQ ID NO:6 & Br47159; SEQ ID NO:8),

*Solanum lycopersicum* (Slg98247; SEQ ID NO:10), and *Oryza sativa* (Os05g03100; SEQ ID NO:12)(second column).

|  | Nucleotide sequence | Amino acid sequence |
|---|---|---|
| At4g38600 | 62 | 40 |
| Br17038 | 86 | 81 |
| Br47159 | 86 | 80 |
| Slg98247 | 63 | 39 |
| Os05g03100 | 61 | 36 |

Drought Assay.

Wild-type, TDNA knock-out and complementation lines were sown in a replicated blocked design in 50-cell seedlings trays containing a 2:1:1 mix of Metro-Mix 852 soilless medium, fine sand and vermiculite. Planted trays were placed at 4° C. for three days to break dormancy and then transferred to a growth chamber (16 h 22/20° C., 50% rH) for germination and establishment. Complementation lines were sprayed with a glufosinate formulation (20 mg glufosinate, 20 µL Silwet surfactant, 200 mL water) once they had fully expanded cotyledons to assure that only transformed lines were selected. Following this treatment, seedlings in each cell were thinned to a single plant. Once plants reached the 4-6 true leaf stage they were acclimated to greater vapour pressure deficit conditions to promote even drought stress (28/26° C., 25% rH) and unusually small plants were identified for removal prior to drought treatment. Planting trays were soaked with water and then allowed to drain, leaving all cells at pot capacity. Entire trays were watered once half of the wild-type plants in any given tray appeared to be at their permanent wilting point (1.5-2 weeks of drought treatment). Plants were allowed to recover over a few days and survival was recorded, with pre-identified abnormally small plants omitted from further analyses.

Statistical Analysis.

Statistical significance of differing probabilities of survival over this drought treatment was assessed by applying the test of equal or given proportions in the statistical software program, R (http://www.r-project.org/). The function prop.test was used to test the null hypothesis that the proportions of surviving plants between mutant and wild-type (one-tailed), or alternatively, between insertion mutant lines containing or not containing complementing transgenes (two-tailed), were equal.

Results

FIG. 2 shows the drought resistant phenotype of the UPL4 knockout (*Arabidopsis* At5g02880 insertion mutant) as compared to the drought sensitive phenotype of a control (wild-type) plant.

Figure 3:
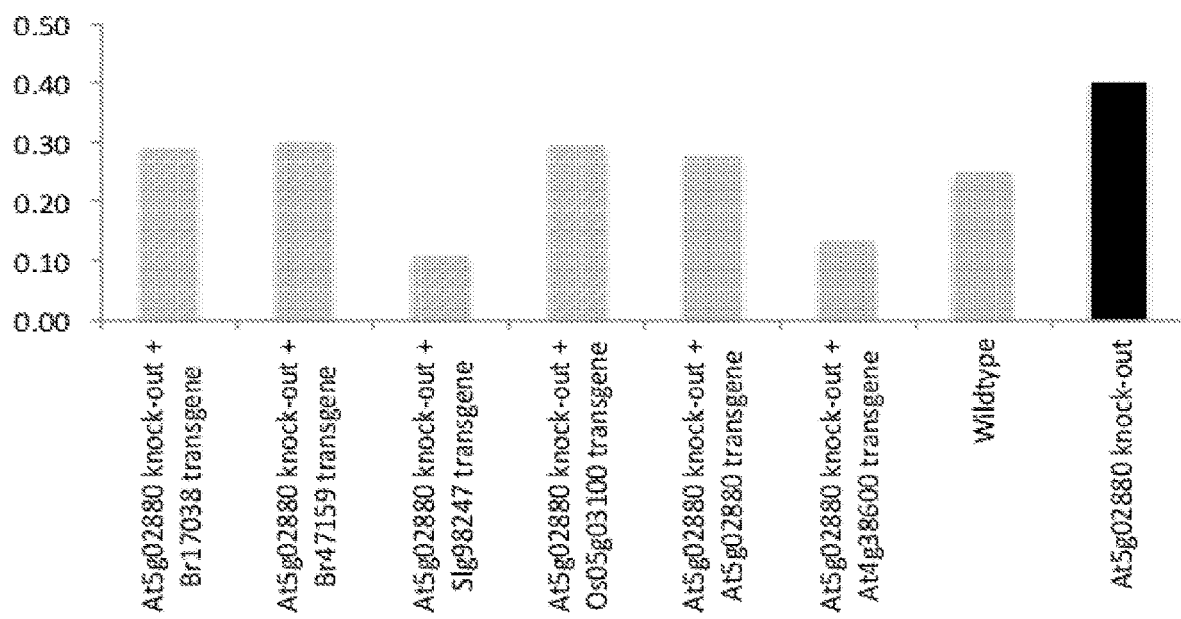
FIG. 3 shows drought survival of At5g02880-insertion mutant (UPL4). The *Arabidopsis thaliana* At5g02880 insertion mutant survived drought significantly better (p<0.05) than wild-type (Col-0) plants or At5g02880 insertion mutants complemented with the coding sequence (CDS) of At5g02880 (SEQ ID NO:1; positive control) and homologs from *Arabidopsis thaliana* (SEQ ID NO:3), *Brassica rapa* (SEQ ID NOs:5 or 7), *Solanum lycopersicum* (SEQ ID NO:9) or *Oryza sativa* (SEQ ID NO:11). This figure demonstrates that an insertion mutation in the UPL4 gene produces a drought resistant phenotype. Moreover, it also indicates that homologs of this gene from monocot and dicot species operate to restore the normal drought-susceptible phenotype. Hence, these homologs perform the same function in drought tolerance in their respective crop species. The observation that both monocot and dicot UPL4 genes can restore drought susceptibility when inserted into the UPL4 insertion mutant of *Arabidopsis* suggests that a reduced activity of the protein encoded by the UPL4 gene renders drought tolerant phenotypes throughout the entire plant kingdom. Hence, prediction of UPL4 (based on homology searches and characteristic domain [HECT] and Armadillo repeat sequences) will allow identification of plant UPL4 homologs in plant species. Subsequently, one can use well-known methods to reduce protein activity of these plant homologs (e.g. mutagenesis, TDNA or transposon insertion, RNAi, etc) to obtain drought resistant plants. Gray bars have significantly lower values (p<0.05) than black bars.

The *Arabidopsis* At5g02880 insertion mutant survived drought significantly better (p<0.05) than wild-type (Col-0) plants or At5g02880 insertion mutants complemented with the coding sequence (CDS) of At5g02880 (SEQ ID NO:1; positive control) and homologs from *Arabidopsis thaliana* (SEQ ID NO:3), *Brassica rapa* (SEQ ID NOs: 5 and 7), *Solanum lycopersicum* (SEQ ID NO:9) or *Oryza sativa* (SEQ ID NO:11). FIG. 3 demonstrates that an insertion mutation in the UPL4 gene produces a drought resistant phenotype. Moreover, it also indicates that homologs of this gene from monocot and dicot species operate to restore the normal drought-susceptible phenotype. Hence, these homologs perform the same function in drought tolerance in their respective crop species. The observation that both monocot and dicot UPL4 genes can restore drought susceptibility when inserted into the UPL4 mutant of *Arabidopsis* suggests that a reduced activity of the protein encoded by the UPL4 gene renders drought tolerant phenotypes throughout the entire plant kingdom. Hence, prediction of UPL4 (based on homology searches and characteristic domain [HECT] and Armadillo repeat sequences) will allow identification of plant UPL4 homologs in plant species. Subsequently, one can use well-known methods to reduce protein activity of these plant homologs (e.g. mutagenesis, TDNA or transposon insertion, RNAi, etc) to obtain drought resistant plants. Grey bars have significantly lower values (p<0.05) than black bars.

Example 4 Drought Resistance in Tomato

Plant material. A novel mutation in the tomato gene Solyc10g055450 (Slg98247; SEQ ID NO:9) was generated through EMS screening. The mutation consisted of an amino acid change of valine (hydrophobic properties) to glutamic acid (negatively charged amino acid) (in position 158 of the protein). A segregating M2 population containing homozygous, heterozygous and wild-type allele were used for all drought experiments.

A second mutation was identified in the same tomato gene, causing an amino acid change of aspartic acid (negatively charged amino acid) to glutamic acid (negative charged amino acid) (in position 114 of the protein). Due to the similarity in biochemical properties, this mutation was unlikely to cause significant changes to the protein properties and was therefore used as a negative control in the drought assays. Sift (Ng and Henikoff, 2003—Nucl. Acids Res. 31: 3812-3814) analysis showed that this mutation is likely to be tolerated. A segregating M2 population containing homozygous, heterozygous and wild-type allele were used for all drought experiments.

Drought assay. Tomato seedlings that were homozygous, heterozygous or wild-type for the described V158E mutation were grown in 2.5 inch plastic pots containing a 2:1:1 mix of Metro-Mix 852 soilless medium, fine sand and vermiculite in a growth chamber (16 h 22/20° C., 50% rH. Upon establishment, seedlings were acclimated to greater vapor pressure deficit conditions to promote even drought stress (28/26° C., 25% rH). Pots were soaked with water and then allowed to drain, leaving all plants at pot capacity. Plants were subjected to a drought stress period of 1 week and then watered and allowed to recover for 24 h, when survival was assessed.

Statistical Analysis.

Statistical significance of differing probabilities of survival over this drought treatment was assessed by apply the test of equal or given proportions in the statistical software program, R (http://www.r-project.org/). The function prop.test was used to test the null hypothesis that the proportions of surviving plants between homozygous and wild-type mutants (one-tailed) were equal.

Results

Figure 4:
FIG. 4 shows the drought phenotype of a tomato (*Solanum lycopersicum*) UPL4-mutant. A segregating M2 population containing homozygous, heterozygous and wild-type allele were used for a drought experiment. The photograph—taken 21 days after initiation of the drought treatment—shows a wild-type tomato plant (right) and a plant carrying the V158E mutation in Sig98247 (left). Drought tolerant phenotype and survival of the drought treatment was significantly better (p<0.1) for the plant carrying the V158E mutation in Sig98247 compared to the wild-type allele, indicating that this alteration of the protein leads to a drought tolerant phenotype in tomato.

Tomato plants, homozygous for the V158E mutation in Sig98247 survived the drought treatment significantly better (p<0.1) compared to the wild-type allele, indicating that this alteration of the protein leads to a drought tolerant phenotype in tomato (FIG. 4). As expected the additional mutation in Sig98247 (D114E) did not show any drought related phenotype (all plants from the segregating M2 population were equally drought susceptible).

The invention claimed is:

1. A *Brassica rapa* or *Oryza sativa* plant, comprising a mutation in an endogenous UPL4 gene resulting in impaired expression of functional UPL4 protein, wherein the functional UPL4 protein has ubiquitin-protein ligase activity, wherein the functional UPL4 protein has at least 95% sequence identity with at least one of SEQ ID NO: 6, 8 and 12, and wherein the plant exhibits improved drought resistance.

2. The plant according to claim 1, which is a *Brassica rapa* plant, wherein the functional UPL4 protein comprises the amino acid sequence of SEQ ID NO: 6 or SEQ ID NO: 8.

3. The plant according to claim 1, which is a *Oryza sativa* plant, wherein the functional UPL4 protein comprises the amino acid sequence of SEQ ID NO: 12.

4. The plant according to claim 1, wherein the plant has been subjected to genetic modification targeting the endogenous UPL4 gene.

5. The plant according to claim 1, wherein the mutation involves an insertion, a deletion and/or substitution of at least one nucleotide in the endogenous UPL4 gene.

6. The plant according to claim 1, wherein the mutation is in an exon sequence, an intron sequence, and/or a regulatory sequence of the endogenous UPL4 gene.

7. A *Brassica rapa* or *Oryza sativa* plant, comprising a gene silencing construct targeting an endogenous UPL4 gene resulting in impaired expression of functional UPL4 protein, wherein the functional UPL4 protein has ubiquitin-protein ligase activity, wherein the functional UPL4 protein has at least 95% sequence identity with at least one of SEQ ID NO: 6, 8 and 12, and wherein the plant exhibits improved drought resistance.

8. The plant according to claim 7, which is a *Brassica rapa* plant, wherein the functional UPL4 protein comprises the amino acid sequence of SEQ ID NO: 6 or SEQ ID No: 8.

9. The plant according to claim 7, which is a *Oryza sativa* plant, wherein the functional UPL4 protein comprises the amino acid sequence of SEQ ID NO: 12.

10. The plant according to claim 7, wherein the gene silencing is RNA interference.

11. The plant according to claim 7, wherein the gene silencing construct is inserted in the genome of the plant.

12. A plant cell obtainable from the plant according to claim 1, wherein the plant cell comprises at least part of a UPL4 gene having a mutation that results in impaired expression of a functional UPL4 protein, wherein the functional UPL4 protein has ubiquitin-protein ligase activity, and wherein the functional UPL4 protein has at least 95% sequence identity with at least one of SEQ ID NO: 6, 8 and 12.

13. A plant product obtainable from the plant according to claim 1, wherein the plant product comprises at least part of a UPL4 gene having a mutation that results in impaired expression of a functional UPL4 protein, wherein the functional UPL4 protein has ubiquitin-protein ligase activity, and wherein the functional UPL4 protein has at least 95% sequence identity with at least one of SEQ ID NO: 6, 8 and 12.

* * * * *